(12) United States Patent
Cripwell et al.

(10) Patent No.: US 10,253,337 B2
(45) Date of Patent: Apr. 9, 2019

(54) RECOMBINANT YEAST AND USE THEREOF

(71) Applicant: Stellenbosch University, Stellenbosch (ZA)

(72) Inventors: Rosemary Anne Cripwell, Stellenbosch (ZA); Willem Heber Van Zyl, Stellenbosch (ZA); Shaunita Hellouise Rose, Somerset West (ZA)

(73) Assignee: Stellenbosch University, Stellenbosch (ZA)

( * ) Notice: Subject to any disclaimer, the term of this patent is extended or adjusted under 35 U.S.C. 154(b) by 0 days.

(21) Appl. No.: 15/830,659

(22) Filed: Dec. 4, 2017

(65) Prior Publication Data

US 2018/0155744 A1 Jun. 7, 2018

(30) Foreign Application Priority Data

Dec. 5, 2016 (GB) .................................. 1620658.3

(51) Int. Cl.
| | |
|---|---|
| *C12P 7/06* | (2006.01) |
| *C12N 9/26* | (2006.01) |
| *C12N 15/10* | (2006.01) |
| *C12N 9/30* | (2006.01) |
| *C12N 9/24* | (2006.01) |
| *C12P 7/16* | (2006.01) |

(52) U.S. Cl.
CPC ................ *C12P 7/06* (2013.01); *C12N 9/242* (2013.01); *C12N 9/2405* (2013.01); *C12P 7/16* (2013.01); *C12Y 302/01* (2013.01); *C12Y 302/01001* (2013.01)

(58) Field of Classification Search
CPC ... C12P 19/04; C12P 7/06; A01H 5/00; C12N 9/2411; C12N 9/2414; C12N 15/10
See application file for complete search history.

(56) References Cited

U.S. PATENT DOCUMENTS

2007/0082385 A1* 4/2007 Smith ...................... C12P 7/06
435/161

FOREIGN PATENT DOCUMENTS

| | | |
|---|---|---|
| DE | 44 25 058 A1 | 1/1996 |
| EP | 0 257 115 A1 | 8/1986 |
| EP | 3 091 070 A1 | 11/2016 |
| WO | 99/28448 A1 | 6/1999 |
| WO | 2006/066579 A1 | 6/2006 |
| WO | 2007/057018 A2 | 5/2007 |
| WO | 108941 * | 9/2009 |
| WO | 03/016524 A1 | 2/2013 |
| WO | 2014/058572 A1 | 4/2014 |

OTHER PUBLICATIONS

Van Zyl et al., Applied Microbiology and Biotechnology, Sep. 2012, 95(6), 1377-1388.*

* cited by examiner

*Primary Examiner* — Maryam Monshipouri
(74) *Attorney, Agent, or Firm* — McNeill Baur PLLC

(57) ABSTRACT

A recombinant yeast that expresses both an α-amylase (SEQ ID NO: 1) and a glucoamylase (SEQ ID NO: 2) from *Talaromyces emersonii* (recently re-named as *Rasamsonia emersonii*) is provided. The use of the recombinant yeast in a process for producing an alcohol, in particular a biofuel, from starch or sugars is also described.

19 Claims, 20 Drawing Sheets

Specification includes a Sequence Listing.

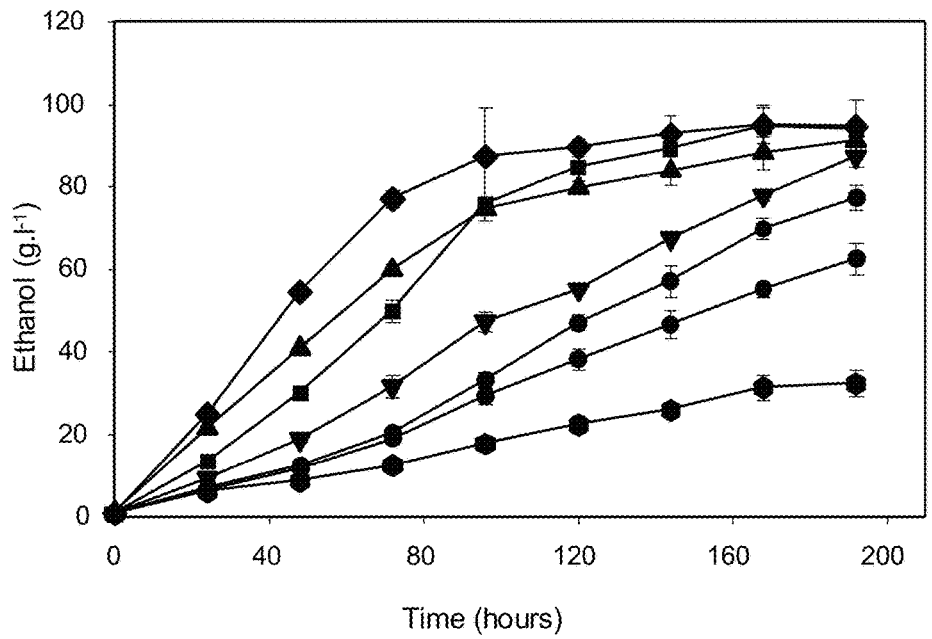

Fig. 15

MTPFVLTAVLFLLGNAVLALTPAEWRKQSIYFLLTDRFGRADNSTTAACDVTERIYCGGSWQGIINHLDY
IQGMGFTAIWISPVTEQLPQNTGEGEAYHGYWQQEIYTVNSNFGTSDDLLALSKALHDRGMYLMVDVVAN
HMGYDGDGDSVDYSVFNPFNSSSYFHPYCLITDYSNQTDVEDCWLGDTTVSLPDLNTTETVVRTIWYDWV
ADLVSNYSIDGLRIDTVKHVEKSFWPGYNSAAGVYCVGEVLDGDPSYTCPYQDYLDGVLNYPIYYQLLYA
FESSSGSISNLYNMINSVASECSDPTLLGNFIENHDNPRFASYTSDYSLAKNVIAFIFFSDGIPIVYAGQ
EQHYNGGNDPYNREATWLSGYSTTAELYTFIATTNAIRSLAISVDSEYLTYKNDPFYYDSNTLAMRKGSD
GLQVITVLSNLGADGSSYTLTLSGSGYSSGTELVEAYTCTTVTVDSNGDIPVPMESGLPRVFLPASSFSG
SSLCSSSPSPTTTTSTSTSTTSTACTTATAVAVLFEELVTTTYGENVYLSGSISQLGDWNTDDAVALSAA
NYTSSNPLWYVTVTLPVGTSFEYKFIKKEENGDVEWESDPNRSYTVPTACTGATETIVDTWR

Fig. 16

MASLVAGALCILGLTPAAFARAPVAARATGSLDSFLATETPIALQGVLNNIGPNGADVAGASAGIVVASP
SRSDPNYFYSWTRDAALTAKYLVDAFIAGNKDLEQTIQQYISAQAKVQTISNPSGDLSTGGLGEPKFNVN
ETAFTGPWGRPQRDGPALRATALIAYANYLIDNGEASTADEIIWPIVQNDLSYITQYWNSSTFDLWEEVE
GSSFFTTAVQHRALVEGNALATRLNHTCSNCVSQAPQVLCFLQSYWTGSYVLANFGGSGRSGKDVNSILG
SIHTFDPAGGCDDSTFQPCSARALANHKVVTDSFRSIYAINSGIAEGSAVAVGRYPEDVYQGGNPWYLAT
AAAAEQLYDAIYQWKKIGSISITDVSLPFFQDIYPSAAVGTYNSGSTTFNDIISAVQTYGDGYLSIVEKY
TPSDGSLTEQFSRTDGTPLSASALTWSYASLLTASARRQSVVPASWGESSASSVPAVCSATSATGPYSTA
TNTVWPSSGSGSSTTTSSAPCTTPTSVAVTFDEIVSTSYGETIYLAGSIPELGNWSTASAIPLRADAYTN
SNPLWYVTVNLPPGTSFEYKFFKNQTDGTIVWEDDPNRSYTVPAYCGQTTAILDDSWQ

Fig. 17

<u>ATGACGCCTTTCGTCCTCACGGCCGTGCTGTTCTTGCTGGGGAATGCCGTGTTGGCC</u>TTGACCCCGGCCGA
ATGGCGCAAACAATCTATCTACTTTCTCCTCACGGACCGCTTTGGCAGGGCAGATAACTCGACCACTGCTG
CCTGCGATGTCACTGAGAGGATCTACTGTGGCGGGAGTTGGCAAGGAATCATCAACCATCTCGACTATATC
CAAGGCATGGGGTTCACGGCCATCTGGATTTCACCGGTGACCGAGCAGCTGCCGCAAAATACGGGTGAGGG
AGAAGCCTATCATGGGTATTGGCAGCAGGAAATATACACGGTCAACTCCAACTTTGGGACATCAGACGATC
TCTTAGCCCTGTCAAAGGCGCTCCATGACCGTGGCATGTACCTCATGGTCGATGTGGTTGCGAATCACATG
GGATACGATGGAGATGGCGACTCCGTTGATTACAGCGTCTTCAATCCATTTAATTCCTC<u>T</u>AGTTATTTCCA
TCCCTATTGCCTGATTACAGACTACAGCAATCAGACCGATGTGGAAGACTGTTGGCTGGGCGATACGACTG
TCTCGTTGCCCGATCTCAACACCACGGAGACTGTTGTGAGGACTATATGGTATGACTGGGTGGCGGATCTC
GTCTCCAATTACTCTATTGATGGGCTTCGCATCGACACGGTGAAACACGTAGAAAAGTCATTCTGGCCTGG
TTACAACAGTGCTGCGGGTGTCTACTGTGTTGGCGAGGTCCTCGATGGAGATCCGTCTTACACTTGTCCCT
ACCAGGATTATCTGGACGGTGTATTAAACTATCCAATATACTATCAACTACTGTATGCGTTTGAATCCTCT
AGCGGCAGCATCAGCAATCTTTACAACATGATCAACTCTGTCGCCTCTGAATGTTCCGATCCCACTCTGTT
GGGCAACTTTATCGAGAACCATGACAACCCTAGATTTGCCTCCTATACAAGTGATTATTCTCTTGCTAAAA
ATGTGATTGCTTTCATCTTCTTCTCTGACGGCATCCCTATCGTCTATGCCGGTCAGGAGCAGCATTACAAC
GGGGGAAATGACCCCTACAACCGCGAGGCCACCTGGCTGTCAGGATACTCGACGACGGCCGAACTGTACAC
GTTCATTGCGACCACCAACGCGATCCGTAGCTTGGCGATCTCCGTCGACTCGGAGTATTTGACGTACAAGA
ATGACCCATTCTACTACGACAGCAATACCCTCGCTATGCGCAAGGGTTCGGATGGCCTGCAGGTCATCACT
GTTCTGTCCAATCTGGGCGCCGATGGTAGCTCGTACACGTTGACTCTGAGTGGCAGTGGCTATTCGTCAGG
CACGGAGCTGGTGGAAGCTTACACCTGCACAACGGTCACTGTTGACTCTAATGGCGATATTCCAGTTCCCA
TGGAGTCCGGACTGCCGCGCGTTTTCCTACCAGCATCCTCATTCAGTGGTAGCAGTCTATGCAGTTCTTCT
CCTAGCCCTACTACTACAACATCGACATCGACATCGACAACGTCGACGGCCTGCACCACCGCCACCGCTGT
GGCGGTCCTCTTCGAAGAGTTGGTGACAACGACCTACGGTGAAAATGTCTACCTCAGCGGATCGATCAGCC
AACTCGGGGACTGGAACACGGACGACGCCGTGGCCCTGTCCGCAGCTAATTACACTTCTTCGAATCCCCTG
TGGTATGTGACAGTCACATTGCCGGTTGGGACGTCCTTTGAGTACAAGTTCATCAAGAAGGAAGACAACGG
CGATGTCGAGTGGGAGAGCGATCCCAATCGGTCGTATACTGTGCCGACGGCCTGCACGGGAGCGACGGAGA
CGATTGTCGACACATGGAGATAG

Fig. 18

ATGGCCTCCTTAGTCGCAGGTGCCTTATGTATTTTAGGTTTGACCCCAGCAGCCTTCGCAAGAGCCCCAGT
CGCAGCCAGAGCAACAGGTTCATTGGATTCATTTTTGGCTACAGAAACTCCAATCGCATTGCAAGGTGTTT
TGAACAACATCGGTCCAAACGGTGCTGATGTTGCTGGTGCATCTGCTGGTATTGTTGTTGCATCTCCATCT
AGATCAGATCCAAACTACTTCTACTCTTGGACTAGAGATGCTGCATTGACTGCTAAGTATTTGGTTGATGC
TTTTATTGCAGGTAATAAGGATTTGGAACAAACTATCCAACAATACATCTCTGCACAAGCTAAGGTTCAAA
CTATCTCAAACCCATCTGGTGACTTGTCTACAGGTGGTTTGGGTGAACCAAAGTTTAATGTTAACGAAACT
GCTTTTACAGGTCCATGGGGTAGACCACAAAGAGATGGTCCAGCATTGAGAGCAACTGCTTTGATCGCATA
CGCTAACTACTTGATCGATAACGGTGAAGCTTCTACAGCAGATGAAATCATCTGGCCAATCGTTCAAAACG
ATTTGTCATACATCACTCAATACTGGAACTCTTCTACATTTGATTTGTGGGAAGAAGTTGAAGGTTCTTCT
TTCTTTACTACAGCTGTTCAACATAGAGCATTAGTTGAGGGTAATGCATTGGCTACTAGATTGAACCATAC
ATGTTCAAACTGTGTTTCTCAAGCTCCACAAGTCTTGTGTTTCTTGCAATCATATTGGACTGGTTCTTACG
TTTTGGCTAATTTTGGTGGTTCAGGTAGATCAGGTAAAGATGTTAATTCAATCTTGGGTTCTATTCATACT
TTTGATCCAGCTGGTGGTTGTGATGATTCTACATTTCAACCATGTTCAGCAAGAGCTTTGGCAAACCATAA
GGTTGTTACTGATTCTTTTAGATCAATCTATGCTATTAATTCTGGTATTGCAGAAGGTTCAGCTGTTGCAG
TTGGTAGATATCCAGAAGATGTTTACCAAGGTGGTAATCCATGGTACTTGGCTACTGCTGCAGCTGCAGAA
CAATTGTACGATGCAATCTATCAATGGAAGAAAATTGGTTCAATCTCTATCACAGATGTTTCTTTGCCATT
TTTCCAAGATATCTATCCATCAGCTGCAGTTGGTACTTACAACTCAGGTTCTACTACTTTTAATGATATCA
TTTCTGCTGTTCAAACATATGGTGACGGTTACTTGTCAATCGTTGAAAAGTACACTCCATCAGATGGTTCT
TTGACAGAACAATTTTCTAGAACTGATGGTACACCATTGTCAGCTTCTGCATTAACTTGGTCATACGCTTC
TTTGTTAACAGCTTCAGCAAGAAGACAATCTGTTGTTCCAGCATCATGGGGTGAATCTTCAGCTTCTTCAG
TTCCAGCAGTTTGTTCAGCTACTTCTGCAACAGGTCCATATTCTACAGCTACTAATACAGTTTGGCCATCT
TCAGGTTCAGGTTCTTCAACTACAACTTCTTCAGCTCCATGTACAACTCCAACTTCTGTTGCAGTTACATT
CGATGAAATCGTTTCAACTTCTTACGGTGAAACAATATATTTGGCTGGTTCTATTCCAGAATTGGGTAATT
GGTCAACTGCTTCTGCAATTCCATTGAGAGCTGATGCATACACAAATTCTAATCCATTGTGGTATGTTACT
GTTAATTTGCCACCAGGTACATCATTCGAATACAAGTTTTTCAAGAATCAAACTGATGGTACAATTGTTTG
GGAAGATGATCCAAATAGATCCTACACCGTTCCTGCTTACTGTGGTCAAACTACCGCAATCTTGGACGACT
CTTGGCAA

Fig. 19

```
ATGGCGTCCCTCGTTGCTGGCGCTCTCTGCATCCTGGGCCTGACGCCTGCTGCATTTGCACGAGCGCCCGT
TGCAGCGCGAGCCACCGGTTCCCTGGACTCCTTTCTCGCAACCGAAACTCCAATTGCCCTCCAAGGCGTGC
TGAACAACATCGGGCCCAATGGTGCTGATGTGGCAGGAGCAAGCGCCGGCATTGTGGTTGCCAGTCCGAGC
AGGAGCGACCCAAATTATTTCTACTCCTGGACACGTGACGCAGCGCTCACGGCCAAATACCTCGTTGACGC
CTTCATCGCGGGCAACAAGGACCTAGAGCAGACCATCCAGCAGTACATCAGCGCGCAGGCGAAGGTGCAAA
CTATCTCCAATCCGTCCGGAGATTTATCCACCGGTGGCTTAGGTGAGCCCAAGTTCAATGTGAATGAGACG
GCTTTTACCGGGCCCTGGGGTCGTCCACAGAGGGACGGACCAGCGTTGAGAGCGACGGCCCTCATTGCGTA
TGCGAACTATCTCATCGACAACGGCGAGGCTTCGACTGCCGATGAGATCATCTGGCCGATTGTCCAGAATG
ATCTGTCCTACATCACCCAATACTGGAACTCATCCACCTTCGACCTCTGGGAAGAAGTAGAAGGTTCCTCA
TTCTTCACAACCGCCGTGCAACACCGCGCCCTGGTCGAAGGCAATGCACTGGCAACAAGGCTGAACCACAC
GTGCTCCAACTGCGTCTCTCAGGCCCCTCAGGTCCTGTGTTTCCTGCAGTCATACTGGACCGGATCGTATG
TTCTGGCCAACTTTGGTGGCAGCGGTCGTTCCGGCAAGGACGTGAACTCGATTCTGGGCAGCATCCACACC
TTTGATCCCGCCGGAGGCTGTGACGACTCGACCTTCCAGCCGTGTTCGGCCCGTGCCTTGGCAAATCACAA
GGTGGTCACCGACTCGTTCCGGAGTATCTATGCGATCAACTCAGGCATCGCAGAGGGATCTGCCGTGGCAG
TCGGCCGCTACCCTGAGGATGTCTACCAGGGCGGGAACCCCTGGTACCTGGCCACAGCAGCGGCTGCAGAG
CAGCTTTACGACGCCATCTACCAGTGGAAGAAGATCGGCTCGATAAGTATCACGGACGTTAGTCTGCCATT
TTTCCAGGATATCTACCCTTCTGCCGCGGTGGGCACCTATAACTCTGGCTCCACGACTTTCAACGACATCA
TCTCGGCCGTCCAGACGTATGGTGATGGATATCTGAGTATTGTCGAGAAATATACTCCCTCAGACGGCTCT
CTTACCGAACAATTCTCCCGTACAGACGGCACTCCGCTTTCTGCCTCTGCCCTGACTTGGTCGTACGCTTC
TCTCCTAACCGCTTCGGCCCGCAGACAGTCCGTCGTCCCTGCTTCCTGGGGCGAAAGCTCCGCAAGCAGCG
TCCCTGCCGTCTGCTCTGCCACCTCTGCCACGGGCCCATACAGCACGGCTACCAACACCGTCTGGCCAAGC
TCTGGCTCTGGCAGCTCAACAACCACCAGTAGCGCCCCATGCACCACTCCTACCTCTGTGGCTGTGACCTT
CGACGAAATCGTCAGCACCAGTTACGGGGAGACAATCTACCTGGCCGGCTCGATCCCCGAGCTGGGCAACT
GGTCCACGGCCAGCGCGATCCCCCTCCGCGCGGATGCTTACACCAACAGCAACCCGCTCTGGTACGTGACC
GTCAATCTGCCCCCTGGCACCAGCTTCGAGTACAAGTTCTTCAAGAACCAGACGGACGGGACCATCGTCTG
GGAAGACGACCCGAACCGGTCGTACACGGTCCCAGCGTACTGTGGGCAGACTACCGCCATTCTTGACGATA
GTTGGCAGTGA
```

Fig. 20

```
   1 atgacgcctt tcgtcctcac ggccgtgctg ttcttgctgg ggaatgccgt gttggccttg
  61 acccggccg aatggcgcaa acaatctatc tactttctcc tcacggaccg ctttggcagg
 121 gcagataact cgaccactgc tgcctgcgat gtcactgaga ggatctactg tggcgggagt
 181 tggcaaggaa tcatcaacca tctcgactat atccaaggca tggggttcac ggccatctgg
 241 atttcaccgg tgaccgagca gctgccgcaa atacgggtg agggagaagc ctatcatggg
 301 tattggcagc aggaaatata cacggtcaac tccaactttg ggacatcaga cgatctctta
 361 gccctgtcaa aggcgctcca tgaccgtggc atgtacctca tggtcgatgt ggttgcgaat
 421 cacatgggat acgatggaga tggcgactcc gttgattaca gcgtcttcaa tccatttaat
 481 tcctcgagtt atttccatcc ctattgcctg attacagact acagcaatca gaccgatgtg
 541 gaagactgtt ggctgggcga tacgactgtc tcgttgcccg atctcaacac cacggagact
 601 gttgtgagga ctatatggta tgactgggtg gcggatctcg tctccaatta ctctattgat
 661 gggcttcgca tcgacacggt gaaacacgta gaaaagtcat tctggcctgg ttacaacagt
 721 gctgcgggtg tctactgtgt tggcgaggtc ctcgatggag atccgtctta cacttgtccc
 781 taccaggatt atctggacgg tgtattaaac tatccaatat actatcaact actgtatgcg
 841 tttgaatcct ctagcggcag catcagcaat ctttacaaca tgatcaactc tgtcgcctct
 901 gaatgttccg atcccactct gttgggcaac tttatcgaga accatgacaa ccctagattt
 961 gcctcctata caagtgatta ttctcttgct aaaaatgtga ttgctttcat cttcttctct
1021 gacggcatcc ctatcgtcta tgccggtcag gagcagcatt acaacggggg aaatgacccc
1081 tacaaccgcg aggccacctg gctgtcagga tactcgacga cggccgaact gtacacgttc
1141 attgcgacca ccaacgcgat ccgtagcttg gcgatctccg tcgactcgga gtatttgacg
1201 tacaagaatg acccattcta ctacgacagc aatacccctcg ctatgcgcaa gggttcggat
1261 ggcctgcagg tcatcactgt tctgtccaat ctgggcgccg atggtagctc gtacacgttg
1321 actctgagtg gcagtggcta ttcgtcaggc acggagctgg tggaagtccgg cacctgcaca
1381 acggtcactg ttgactctaa tggcgatatt ccagttccca tggagtccgg actgccgcgc
1441 gttttcctac cagcatcctc attcagtggt agcagtctat gcagttcttc tcctagccct
1501 actactacaa catcgacatc gacatcgaca acgtcgacgg cctgcaccac cgccaccgct
1561 gtggcggtcc tcttcgaaga gttggtgaca acgacctacg gtgaaaatgt ctacctcagc
1621 ggatcgatca gccaactcgg ggactggaac acggacgacg ccgtggccct gtccgcagct
1681 aattacactt cttcgaatcc cctgtggtat gtgacagtca cattgccggt tgggacgtcc
1741 tttgagtaca agttcatcaa gaaggaagag aacggcgatg tcgagtggga gagcgatccc
1801 aatcggtcgt atactgtgcc gacggcctgc acggagcga cggagacgat tgtcgacaca
1861 tggagatag
```

Fig. 21

```
   1 acgagatgtg tatatactgt gaaccaaact agatgatgtc agttatgctg gtctgagaac
  61 tcatagaagc ccttgaaaat accccaagct agcactccaa ccctaactct gttgctctac
 121 tagatcaaga cgagtactct gattgagctg caggcttgga atatatgatt agcagaaaaa
 181 gggttaaaac ttgtatgaca atcagtttgt cagtactccg tagtgatgcc atgtctatag
 241 agtcgacact aaggcagcat gtgaatgagt cggaaatgac aggaagcaga ttccttaaca
 301 gtcatgttct ccgtgcctgc atccccacgt cacctgcaaa gatgcgacgc tactccacac
 361 cggcgccttg atgtctgctg ttcctggcct agtggagccc atgcgctgc tagctcgtgg
 421 tcttcgaata aatcagaata aaaaacggag taattaattg cgcccgcaac aaactaagca
 481 atgtaactca atgccaagct tccgctgatg ctcttgacat ctccgtagtg gcttctttcg
 541 taatttcaga cgtatatata gtagtaatgc ccagcaggcc gggataatga tgggatttc
 601 tgaactctca gcttccgtac gctgaacagt ttgcttgcgt tgtcaaccat ggcgtccctc
 661 gttgctggcg ctctctgcat cctgggcctg acgcctgctg catttgcacg agcgccgtt
 721 gcagcgcgag ccaccggttc cctggactcc tttctcgcaa ccgaaactcc aattgccctc
 781 caaggcgtgc tgaacaacat cgggcccaat ggtgctgatg tggcaggagc aagcgccggc
 841 attgtggttg ccagtccgag caggagcgac ccaaattgta ggttctttcc caccagaaat
 901 tacttattta aatcagccct ctgacaggtt gaagatttct actcctggac acgtgacgca
 961 gcgctcacgg ccaaatacct cgtcgacgcc ttcatcgcgg caacaaggaa cctagagcag
1021 accatccagc agtacatcag cgcgcaggcg aaggtgcaaa ctatctccaa tccgtccgga
1081 gatttatcca ccggtggctt aggtgagccc aagttcaatg tgaatgagac ggcttttacc
1141 gggccctggg gtcgtccaca gagggacgga ccagcgttga gagcgacggc cctcattgcg
1201 tatgcgaact atctcatcgt aagcttctgc tcgctgccct tctctctgct cgtatgctaa
1261 gtagtcctgt caggacaacg gcgaggcttc gactgccgat gagatcatct ggccgattgt
1321 ccagaatgat ctgtcctaca tcacccaata ctggaactca tccaccttcg gtaggcaaat
1381 gaatattccc gacacagcgt ggtactaatt tgattcagac ctctgggaag aagtagaagg
1441 atcctcattc ttcacaaccg ccgtgcaaca ccgcgccctg gtcgaaggca atgcactggc
1501 aacaaggctg aaccacacgt gctccaactg cgtctctcag gcccctcagg tcctgtgttt
1561 cctgcagtca tactggaccg gatcgtatgt tctggccaac tttggtggca gcggtcgttc
1621 cggcaaggac gtgaattcga ttctgggcag catccacacc tttgatcccg ccggaggctg
1681 tgacgactcg accttccagc cgtgttcggc ccgtgccttg caaatcaca aggtggtcac
1741 cgactcgttc cggagtatct atgcgatcaa ctcaggcatc gcagagggat ctgccgtggc
1801 agtcggccgc taccctgagg atgtctacca gggcgggaac ccctggtacc tggccacagc
1861 agcggctgca gagcagcttt acgacgccat ctaccagtgg aagaagatcg gctcgataag
1921 tatcacggac gttagtctgc cattttccca ggatatctac ccttctgccg cggtgggcac
1981 ctataactct ggctccacga ctttcaacga catcatctcg gccgtccaga cgtatggtga
2041 tggatatctg agtattgtcg tacgttttgc cttagattct caggtgtaaa gaaaaaaatg
2101 gaactaactc agttctagga gaaatatact ccctcagacg gctctcttac cgaacaattc
2161 tcccgtacag acggcactcc gctttctgcc tctgccctga cttggtcgta cgcttctctc
2221 ctaaccgctt cggcccgcag acagtccgtc gtccctgctt cctggggcga agctccgca
2281 agcagcgtcc ctgccgtctg ctctgccacc tctgccacgg gccatacag cacggctacc
2341 aacaccgtct ggccaagctc tggctctggc agtcaacaa ccaccagtag cgcccatgc
2401 accactccta cctctgtggc tgtgaccttc gacgaaatcg tcagcaccag ttacggggag
2461 acaatctacc tggccggctc gatccccgag ctgggcaact ggtccacggc cagcgcgatc
2521 cccctccgcg cggatgctta caccaacagc aaccgctct ggtacgtgac cgtcaatctg
2581 cccctggca ccagcttcga gtacaagttc ttcaagaacc agacggacgg gaccatcgtc
2641 tgggaagacg acccgaaccg gtcgtacacg gtcccagcgt actgtgggca gactaccgcc
2701 attcttgacg atagttggca gtgagataac atccacccct ctgtttta
```

Fig. 22

SEQUENCE LISTING

```
<160> NUMBER OF SEQ ID NOS: 50

<210> SEQ ID NO 1
<211> LENGTH: 622
<212> TYPE: PRT
<213> ORGANISM: Rasamsonia emersonii

<400> SEQUENCE: 1

Met Thr Pro Phe Val Leu Thr Ala Val Leu Phe Leu Leu Gly Asn Ala
1               5                   10                  15

Val Leu Ala Leu Thr Pro Ala Glu Trp Arg Lys Gln Ser Ile Tyr Phe
            20                  25                  30

Leu Leu Thr Asp Arg Phe Gly Arg Ala Asp Asn Ser Thr Thr Ala Ala
        35                  40                  45
```

-continued

```
Cys Asp Val Thr Glu Arg Ile Tyr Cys Gly Gly Ser Trp Gln Gly Ile
         50                  55                  60

Ile Asn His Leu Asp Tyr Ile Gln Gly Met Gly Phe Thr Ala Ile Trp
 65                  70                  75                  80

Ile Ser Pro Val Thr Glu Gln Leu Pro Gln Asn Thr Gly Glu Gly Glu
                 85                  90                  95

Ala Tyr His Gly Tyr Trp Gln Gln Glu Ile Tyr Thr Val Asn Ser Asn
                100                 105                 110

Phe Gly Thr Ser Asp Asp Leu Leu Ala Leu Ser Lys Ala Leu His Asp
            115                 120                 125

Arg Gly Met Tyr Leu Met Val Asp Val Val Ala Asn His Met Gly Tyr
        130                 135                 140

Asp Gly Asp Gly Asp Ser Val Asp Tyr Ser Val Phe Asn Pro Phe Asn
145                 150                 155                 160

Ser Ser Ser Tyr Phe His Pro Tyr Cys Leu Ile Thr Asp Tyr Ser Asn
                165                 170                 175

Gln Thr Asp Val Glu Asp Cys Trp Leu Gly Asp Thr Thr Val Ser Leu
            180                 185                 190

Pro Asp Leu Asn Thr Thr Glu Thr Val Arg Thr Ile Trp Tyr Asp
        195                 200                 205

Trp Val Ala Asp Leu Val Ser Asn Tyr Ser Ile Asp Gly Leu Arg Ile
    210                 215                 220

Asp Thr Val Lys His Val Glu Lys Ser Phe Trp Pro Gly Tyr Asn Ser
225                 230                 235                 240

Ala Ala Gly Val Tyr Cys Val Gly Glu Val Leu Asp Gly Asp Pro Ser
                245                 250                 255

Tyr Thr Cys Pro Tyr Gln Asp Tyr Leu Asp Gly Val Leu Asn Tyr Pro
            260                 265                 270

Ile Tyr Tyr Gln Leu Leu Tyr Ala Phe Glu Ser Ser Ser Gly Ser Ile
        275                 280                 285

Ser Asn Leu Tyr Asn Met Ile Asn Ser Val Ala Ser Glu Cys Ser Asp
    290                 295                 300

Pro Thr Leu Leu Gly Asn Phe Ile Glu Asn His Asp Asn Pro Arg Phe
305                 310                 315                 320

Ala Ser Tyr Thr Ser Asp Tyr Ser Leu Ala Lys Asn Val Ile Ala Phe
                325                 330                 335

Ile Phe Phe Ser Asp Gly Ile Pro Ile Val Tyr Ala Gly Gln Glu Gln
            340                 345                 350

His Tyr Asn Gly Gly Asn Asp Pro Tyr Asn Arg Glu Ala Thr Trp Leu
        355                 360                 365

Ser Gly Tyr Ser Thr Thr Ala Glu Leu Tyr Thr Phe Ile Ala Thr Thr
    370                 375                 380

Asn Ala Ile Arg Ser Leu Ala Ile Ser Val Asp Ser Glu Tyr Leu Thr
385                 390                 395                 400

Tyr Lys Asn Asp Pro Phe Tyr Tyr Asp Ser Asn Thr Leu Ala Met Arg
                405                 410                 415

Lys Gly Ser Asp Gly Leu Gln Val Ile Thr Val Leu Ser Asn Leu Gly
            420                 425                 430

Ala Asp Gly Ser Ser Tyr Thr Leu Thr Leu Ser Gly Ser Gly Tyr Ser
        435                 440                 445

Ser Gly Thr Glu Leu Val Glu Ala Tyr Thr Cys Thr Thr Val Thr Val
    450                 455                 460
```

```
Asp Ser Asn Gly Asp Ile Pro Val Pro Met Glu Ser Gly Leu Pro Arg
465                 470                 475                 480

Val Phe Leu Pro Ala Ser Ser Phe Ser Gly Ser Ser Leu Cys Ser Ser
                485                 490                 495

Ser Pro Ser Pro Thr Thr Thr Thr Ser Thr Ser Thr Ser Thr Thr Ser
            500                 505                 510

Thr Ala Cys Thr Thr Ala Thr Ala Val Ala Val Leu Phe Glu Glu Leu
        515                 520                 525

Val Thr Thr Thr Tyr Gly Glu Asn Val Tyr Leu Ser Gly Ser Ile Ser
    530                 535                 540

Gln Leu Gly Asp Trp Asn Thr Asp Asp Ala Val Ala Leu Ser Ala Ala
545                 550                 555                 560

Asn Tyr Thr Ser Asn Pro Leu Trp Tyr Val Thr Val Thr Leu Pro
                565                 570                 575

Val Gly Thr Ser Phe Glu Tyr Lys Phe Ile Lys Lys Glu Glu Asn Gly
            580                 585                 590

Asp Val Glu Trp Glu Ser Asp Pro Asn Arg Ser Tyr Thr Val Pro Thr
                595                 600                 605

Ala Cys Thr Gly Ala Thr Glu Thr Ile Val Asp Thr Trp Arg
610                 615                 620
```

```
<210> SEQ ID NO 2
<211> LENGTH: 618
<212> TYPE: PRT
<213> ORGANISM: Rasamsonia emersonii

<400> SEQUENCE: 2

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
    130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
    210                 215                 220
```

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
            245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
            275                 280                 285

Gly Gly Cys Asp Asp Ser Thr Phe Gln Pro Cys Ser Ala Arg Ala Leu
        290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro
                325                 330                 335

Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
        435                 440                 445

Ala Ser Leu Leu Thr Ala Ser Ala Arg Arg Gln Ser Val Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 3
<211> LENGTH: 1869

<212> TYPE: DNA
<213> ORGANISM: Artificial Sequence
<220> FEATURE:
<223> OTHER INFORMATION: Synthetic DNA sequence coding for Rasamsonia
      emersonii alpha-amylase

<400> SEQUENCE: 3

| | | | | | |
|---|---|---|---|---|---|
| atgacgcctt | tcgtcctcac | ggccgtgctg | ttcttgctgg | ggaatgccgt | gttggccttg | 60 |
| accccggccg | aatggcgcaa | acaatctatc | tactttctcc | tcacggaccg | ctttggcagg | 120 |
| gcagataact | cgaccactgc | tgcctgcgat | gtcactgaga | ggatctactg | tggcgggagt | 180 |
| tggcaaggaa | tcatcaacca | tctcgactat | atccaaggca | tggggttcac | ggccatctgg | 240 |
| atttcaccgg | tgaccgagca | gctgccgcaa | aatacgggtg | agggagaagc | ctatcatggg | 300 |
| tattggcagc | aggaaatata | cacggtcaac | tccaactttg | gacatcaga | cgatctctta | 360 |
| gccctgtcaa | aggcgctcca | tgaccgtggc | atgtacctca | tggtcgatgt | ggttgcgaat | 420 |
| cacatgggat | acgatggaga | tggcgactcc | gttgattaca | gcgtcttcaa | tccatttaat | 480 |
| tcctctagtt | atttccatcc | ctattgcctg | attacagact | acagcaatca | gaccgatgtg | 540 |
| gaagactgtt | ggctgggcga | tacgactgtc | tcgttgcccg | atctcaacac | cacggagact | 600 |
| gttgtgagga | ctatatggta | tgactgggtg | gcggatctcg | tctccaatta | ctctattgat | 660 |
| gggcttcgca | tcgacacggt | gaaacacgta | gaaaagtcat | tctggcctgg | ttacaacagt | 720 |
| gctgcgggtg | tctactgtgt | tggcgaggtc | ctcgatggaa | tccgtctta | cacttgtccc | 780 |
| taccaggatt | atctggacgg | tgtattaaac | tatccaatat | actatcaact | actgtatgcg | 840 |
| tttgaatcct | ctagcggcag | catcagcaat | ctttacaaca | tgatcaactc | tgtcgcctct | 900 |
| gaatgttccg | atcccactct | gttgggcaac | tttatcgaga | accatgacaa | ccctagattt | 960 |
| gcctcctata | caagtgatta | ttctcttgct | aaaaatgtga | ttgctttcat | cttcttctct | 1020 |
| gacggcatcc | ctatcgtcta | tgccggtcag | gagcagcatt | acaacggggg | aaatgacccc | 1080 |
| tacaaccgcg | aggccacctg | gctgtcagga | tactcgacga | cggccgaact | gtacacgttc | 1140 |
| attgcgacca | ccaacgcgat | ccgtagcttg | gcgatctccg | tcgactcgga | gtatttgacg | 1200 |
| tacaagaatg | acccattcta | ctacgacagc | aataccctcg | ctatgcgcaa | gggttcggat | 1260 |
| ggcctgcagg | tcatcactgt | tctgtccaat | ctgggcgccg | atggtagctc | gtacacgttg | 1320 |
| actctgagtg | gcagtggcta | ttcgtcaggc | acggagctgg | tggaagctta | cacctgcaca | 1380 |
| acggtcactg | ttgactctaa | tggcgatatt | ccagttccca | tggagtccgg | actgccgcgc | 1440 |
| gttttcctac | cagcatcctc | attcagtggt | agcagtctat | gcagttcttc | tcctagccct | 1500 |
| actactacaa | catcgacatc | gacatcgaca | acgtcgacgg | cctgcaccac | cgccaccgct | 1560 |
| gtggcggtcc | tcttcgaaga | gttggtgaca | acgacctacg | tgaaaatgt | ctacctcagc | 1620 |
| ggatcgatca | gccaactcgg | ggactggaac | acggacgacg | ccgtggccct | gtccgcagct | 1680 |
| aattacactt | cttcgaatcc | cctgtggtat | gtgacagtca | cattgccggt | tgggacgtcc | 1740 |
| tttgagtaca | agttcatcaa | gaaggaagag | aacggcgatg | tcgagtggga | gagcgatccc | 1800 |
| aatcggtcgt | atactgtgcc | gacggcctgc | acgggagcga | cggagacgat | tgtcgacaca | 1860 |
| tggagatag | | | | | | 1869 |

<210> SEQ ID NO 4
<211> LENGTH: 1854
<212> TYPE: DNA
<213> ORGANISM: Artificial Sequence
<220> FEATURE:
<223> OTHER INFORMATION: Optimised DNA sequence coding for the Rasamsonia emersonii glucoamylase

<400> SEQUENCE: 4

```
atggcctcct tagtcgcagg tgccttatgt attttaggtt tgaccccagc agccttcgca      60
agagccccag tcgcagccag agcaacaggt tcattggatt cattttggc tacagaaact     120
ccaatcgcat tgcaaggtgt tttgaacaac atcggtccaa acggtgctga tgttgctggt     180
gcatctgctg gtattgttgt tgcatctcca tctagatcag atccaaacta cttctactct     240
tggactagag atgctgcatt gactgctaag tatttggttg atgcttttat tgcaggtaat     300
aaggatttgg aacaaactat ccaacaatac atctctgcac aagctaaggt tcaaactatc     360
tcaaacccat ctggtgactt gtctacaggt ggtttgggtg aaccaaagtt taatgttaac     420
gaaactgctt ttacaggtcc atggggtaga ccacaaagag atggtccagc attgagagca     480
actgctttga tcgcatacgc taactacttg atcgataacg gtgaagcttc tacagcagat     540
gaaatcatct ggccaatcgt tcaaaacgat ttgtcataca tcactcaata ctggaactct     600
tctacatttg atttgtggga agaagttgaa ggttcttctt tctttactac agctgttcaa     660
catagagcat tagttgaggg taatgcattg gctactagat tgaaccatac atgttcaaac     720
tgtgtttctc aagctccaca agtcttgtgt ttcttgcaat catattggac tggttcttac     780
gttttggcta attttggtgg ttcaggtaga tcaggtaaag atgttaattc aatcttgggt     840
tctattcata cttttgatcc agctggtggt tgtgatgatt ctacatttca accatgttca     900
gcaagagctt tggcaaacca taaggttgtt actgattctt tagatcaat ctatgctatt     960
aattctggta ttgcagaagg ttcagctgtt gcagttggta gatatccaga agatgtttac    1020
caaggtggta atccatggta cttggctact gctgcagctg cagaacaatt gtacgatgca    1080
atctatcaat ggaagaaaat tggttcaatc tctatcacag atgtttcttt gccatttttc    1140
caagatatct atccatcagc tgcagttggt acttacaact caggttctac tactttaat    1200
gatatcattt ctgctgttca aacatatggt gacggttact tgtcaatcgt tgaaaagtac    1260
actccatcag atggttctttt gacagaacaa ttttctagaa ctgatggtac accattgtca    1320
gcttctgcat taacttggtc atacgcttct ttgttaacag cttcagcaag aagacaatct    1380
gttgttccag catcatgggg tgaatcttca gcttcttcag ttccagcagt tgttcagct    1440
acttctgcaa caggtccata ttctacagct actaatacag tttggccatc ttcaggttca    1500
ggttcttcaa ctacaacttc ttcagctcca tgtacaactc caacttctgt tgcagttaca    1560
ttcgatgaaa tcgtttcaac ttcttacggt gaaacaatat atttggctgg ttctattcca    1620
gaattgggta ttggtcaac tgcttctgca attccattga gagctgatgc atacacaaat    1680
tctaatccat tgtggtatgt tactgttaat ttgccaccag tacatcatt cgaatacaag    1740
ttttcaaga atcaaactga tggtacaatt gtttgggaag atgatccaaa tagatcctac    1800
accgttcctg cttactgtgg tcaaactacc gcaatcttgg acgactcttg gcaa          1854
```

<210> SEQ ID NO 5
<211> LENGTH: 1857
<212> TYPE: DNA
<213> ORGANISM: Artificial Sequence
<220> FEATURE:
<223> OTHER INFORMATION: Adapted native DNA sequence coding for
      Rasamsonia emersonii glucoamylase

<400> SEQUENCE: 5

```
atggcgtccc tcgttgctgg cgctctctgc atcctgggcc tgacgcctgc tgcatttgca      60
```

```
cgagcgcccg ttgcagcgcg agccaccggt tccctggact cctttctcgc aaccgaaact     120
ccaattgccc tccaaggcgt gctgaacaac atcgggccca atggtgctga tgtggcagga     180
gcaagcgccg gcattgtggt tgccagtccg agcaggagcg acccaaatta tttctactcc     240
tggacacgtg acgcagcgct cacggccaaa tacctcgttg acgccttcat cgcgggcaac     300
aaggacctag agcagaccat ccagcagtac atcagcgcgc aggcgaaggt gcaaactatc     360
tccaatccgt ccggagattt atccaccggt ggcttaggtg agcccaagtt caatgtgaat     420
gagacggctt ttaccgggcc ctggggtcgt ccacagaggg acggaccagc gttgagagcg     480
acggccctca ttgcgtatgc gaactatctc atcgacaacg gcgaggcttc gactgccgat     540
gagatcatct ggccgattgt ccagaatgat ctgtcctaca tcacccaata ctggaactca     600
tccaccttcg acctctggga agaagtagaa ggttcctcat tcttcacaac cgccgtgcaa     660
caccgcgccc tggtcgaagg caatgcactg gcaacaaggc tgaaccacac gtgctccaac     720
tgcgtctctc aggcccctca ggtcctgtgt ttcctgcagt catactggac cggatcgtat     780
gttctggcca actttggtgg cagcggtcgt tccggcaagg acgtgaactc gattctgggc     840
agcatccaca cctttgatcc cgccggaggc tgtgacgact cgaccttcca gccgtgttcg     900
gcccgtgcct tggcaaatca aaggtggtc accgactcgt tccggagtat ctatgcgatc     960
aactcaggca tcgcagaggg atctgccgtg gcagtcggcc gctaccctga ggatgtctac    1020
cagggcggga ccccctggta cctggccaca gcagcggctg cagagcagct ttacgacgcc    1080
atctaccagt ggaagaagat cggctcgata agtatcacgg acgttagtct gccatttttc    1140
caggatatct acccttctgc cgcggtgggc acctataact ctggctccac gacttcaac     1200 gacatcatct cggccgtcca gacgtatggt gatggatatc tgagtattgt cgagaaatat    1260
actccctcag acggctctct taccgaacaa ttctcccgta cagacggcac tccgctttct    1320
gcctctgccc tgacttggtc gtacgcttct ctcctaaccg cttcggcccg cagacagtcc    1380
gtcgtccctg cttcctgggg cgaaagctcc gcaagcagcg tccctgccgt ctgctctgcc    1440
acctctgcca cgggcccata cagcacggct accaacaccg tctggccaag ctctggctct    1500
ggcagctcaa caaccaccag tagcgcccca tgcaccactc ctacctctgt ggctgtgacc    1560
ttcgacgaaa tcgtcagcac cagttacggg gagacaatct acctggccgg ctcgatcccc    1620
gagctgggca ctggtccac ggccagcgcg atcccctcc gcgcggatgc ttacaccaac      1680
agcaacccgc tctggtacgt gaccgtcaat ctgcccctg caccagctt cgagtacaag      1740 ttcttcaaga accagacgga cgggaccatc gtctgggaag acgacccgaa ccggtcgtac    1800
acggtcccag cgtactgtgg gcagactacc gccattcttg acgatagttg gcagtga       1857

<210> SEQ ID NO 6
<211> LENGTH: 1869
<212> TYPE: DNA
<213> ORGANISM: Rasamsonia emersonii

<400> SEQUENCE: 6
atgacgcctt tcgtcctcac ggccgtgctg ttcttgctgg ggaatgccgt gttggccttg     60
accccggccg aatggcgcaa acaatctatc tactttctcc tcacggaccg ctttggcagg    120
gcagataact cgaccactgc tgcctgcgat gtcactgaga ggatctactg tggcgggagt    180
tggcaaggaa tcatcaacca tctcgactat atccaaggca tggggttcac ggccatctgg    240
atttcaccgg tgaccgagca gctgccgcaa atacgggtg agggagaagc ctatcatggg    300
tattggcagc aggaaatata cacggtcaac tccaactttg ggacatcaga cgatctctta    360
```

-continued

```
gccctgtcaa aggcgctcca tgaccgtggc atgtacctca tggtcgatgt ggttgcgaat      420
cacatgggat acgatggaga tggcgactcc gttgattaca gcgtcttcaa tccatttaat      480
tcctcgagtt atttccatcc ctattgcctg attacagact acagcaatca gaccgatgtg      540
gaagactgtt ggctgggcga tacgactgtc tcgttgcccg atctcaacac cacgagact       600 gttgtgagga ctatatggta tgactgggtg gcggatctcg tctccaatta ctctattgat      660
gggcttcgca tcgacacggt gaaacacgta gaaaagtcat tctggcctgg ttacaacagt      720
gctgcgggtg tctactgtgt tggcgaggtc tcgatggag atccgtctta cacttgtccc       780
taccaggatt atctggacgg tgtattaaac tatccaatat actatcaact actgtatgcg      840
tttgaatcct ctagcggcag catcagcaat ctttacaaca tgatcaactc tgtcgcctct      900
gaatgttccg atcccactct gttgggcaac tttatcgaga accatgacaa ccctagattt      960
gcctcctata caagtgatta ttctcttgct aaaaatgtga ttgctttcat cttcttctct     1020
gacggcatcc ctatcgtcta tgccggtcag gagcagcatt acaacggggg aaatgacccc     1080
tacaaccgcg aggccacctg gctgtcagga tactcgacga cggccgaact gtacacgttc     1140
attgcgacca ccaacgcgat ccgtagcttg gcgatctccg tcgactcgga gtatttgacg     1200
tacaagaatg acccattcta ctacgacagc aatacccctcg ctatgcgcaa gggttcggat     1260
ggcctgcagg tcatcactgt tctgtccaat ctgggcgccg atggtagctc gtacacgttg     1320
actctgagtg gcagtggcta ttcgtcaggc acggagctgg tggaagctta cacctgcaca     1380
acggtcactg ttgactctaa tggcgatatt ccagttccca tggagtccgg actgccgcgc     1440
gttttcctac cagcatcctc attcagtggt agcagtctat gcagttcttc tcctagccct     1500
actactacaa catcgacatc gacatcgaca acgtcgacgg cctgcaccac cgccaccgct     1560
gtggcggtcc tcttcgaaga gttggtgaca acgacctacg gtgaaaatgt ctacctcagc     1620
ggatcgatca gccaactcgg ggactggaac acggacgacg ccgtggccct gtccgcagct     1680
aattacactt cttcgaatcc cctgtggtat gtgacagtca cattgccggt tgggacgtcc     1740
tttgagtaca agttcatcaa gaaggaagag aacggcgatg tcgagtggga gagcgatccc     1800
aatcggtcgt atactgtgcc gacggcctgc acgggagcga cggagacgat tgtcgacaca     1860
tggagatag                                                            1869
```

<210> SEQ ID NO 7
<211> LENGTH: 2748
<212> TYPE: DNA
<213> ORGANISM: Talaromyces emersonii

<400> SEQUENCE: 7

```
acgagatgtg tatatactgt gaaccaaact agatgatgtc agttatgctg gtctgagaac       60
tcatagaagc ccttgaaaat accccaagct agcactccaa ccctaactct gttgctctac      120
tagatcaaga cgagtactct gattgagctg caggcttgga atatatgatt agcagaaaaa      180
gggttaaaac ttgtatgaca atcagtttgt cagtactccg tagtgatgcc atgtctatag      240
agtcgacact aaggcagcat gtgaatgagt cggaaatgac aggaagcaga ttccttaaca      300
gtcatgttct ccgtgcctgc atccccacgt cacctgcaaa gatgcgacgc tactccacac      360
cggcgccttg atgtctgctg ttcctggcct agtggagccc catgcgctgc tagctcgtgg      420
tcttcgaata aatcagaata aaaaacggag taattaattg cgcccgcaac aaactaagca      480
atgtaactca atgccaagct tccgctgatg ctcttgacat ctccgtagtg gcttctttcg      540
```

```
taatttcaga cgtatatata gtagtaatgc ccagcaggcc gggataatga tggggatttc    600
tgaactctca gcttccgtac gctgaacagt ttgcttgcgt tgtcaaccat ggcgtccctc    660
gttgctggcg ctctctgcat cctgggcctg acgcctgctg catttgcacg agcgcccgtt    720
gcagcgcgag ccaccggttc cctggactcc tttctcgcaa ccgaaactcc aattgccctc    780
caaggcgtgc tgaacaacat cgggcccaat ggtgctgatg tggcaggagc aagcgccggc    840
attgtggttg ccagtccgag caggagcgac ccaaattgta ggttctttcc caccagaaat    900
tacttattta aatcagccct ctgacaggtt gaagatttct actcctggac acgtgacgca    960
gcgctcacgg ccaaatacct cgtcgacgcc ttcatcgcgg caacaagga cctagagcag   1020 accatccagc agtacatcag cgcgcaggcg aaggtgcaaa ctatctccaa tccgtccgga   1080
gatttatcca ccggtggctt aggtgagccc aagttcaatg tgaatgagac ggcttttacc   1140
gggccctggg gtcgtccaca gagggacgga ccagcgttga gagcgacggc cctcattgcg   1200
tatgcgaact atctcatcgt aagcttctgc tcgctgccct tctctctgct cgtatgctaa   1260
gtagtcctgt caggacaacg gcgaggcttc gactgccgat gagatcatct ggccgattgt   1320
ccagaatgat ctgtcctaca tcacccaata ctggaactca tccaccttcg gtaggcaaat   1380
gaatattccc gacacagcgt ggtactaatt tgattcagac ctctgggaag aagtagaagg   1440
atcctcattc ttcacaaccg ccgtgcaaca ccgcgccctg gtcgaaggca atgcactggc   1500
aacaaggcta aaccacacgt gctccaactg cgtctctcag gcccctcagg tcctgtgttt   1560
cctgcagtca tactggaccg gatcgtatgt tctggccaac tttggtggca gcggtcgttc   1620
cggcaaggac gtgaattcga ttctgggcag catccacacc tttgatcccg ccggaggctg   1680
tgacgactcg accttccagc cgtgttcggc ccgtgccttg gcaaatcaca aggtggtcac   1740
cgactcgttc cggagtatct atgcgatcaa ctcaggcatc gcagagggat ctgccgtggc   1800
agtcggccgc taccctgagg atgtctacca gggcgggaac ccctggtacc tggccacagc   1860
agcggctgca gagcagcttt acgacgccat ctaccagtgg aagaagatcg gctcgataag   1920
tatcacggac gttagtctgc cattttttcca ggatatctac ccttctgccg cggtgggcac   1980
ctataactct ggctccacga ctttcaacga catcatctcg gccgtccaga cgtatggtga   2040
tggatatctg agtattgtcg tacgttttgc cttagattct caggtgtaaa gaaaaaaatg   2100
gaactaactc agttctagga gaaatatact ccctcagacg gctctcttac cgaacaattc   2160
tcccgtacag acggcactcc gctttctgcc tctgccctga cttggtcgta cgcttctctc   2220
ctaaccgctt cggcccgcag acagtccgtc gtccctgctt cctggggcga agctccgca    2280 agcagcgtcc ctgccgtctg ctctgccacc tctgccacgg gcccatacag cacggctacc   2340
aacaccgtct ggccaagctc tggctctggc agctcaacaa ccaccagtag cgccccatgc   2400
accactccta cctctgtggc tgtgaccttc gacgaaatcg tcagcaccag ttacggggag   2460
acaatctacc tggccggctc gatccccgag ctgggcaact ggtccacggc cagcgcgatc   2520
cccctccgcg cggatgctta caccaacagc aacccgctct ggtacgtgac cgtcaatctg   2580 cccccctggca ccagcttcga gtacaagttc ttcaagaacc agacggacgg gaccatcgtc   2640
tgggaagacg acccgaaccg gtcgtacacg gtccagcgt actgtgggca gactaccgcc    2700
attcttgacg atagttggca gtgagataac atccacccct ctgtttta                2748

<210> SEQ ID NO 8
<211> LENGTH: 66
<212> TYPE: DNA
<213> ORGANISM: Artificial Sequence
```

```
<220> FEATURE:
<223> OTHER INFORMATION: PCR oligo-primer for ApuA_Nat-L

<400> SEQUENCE: 8
tgcttatcaa cacacaaaca ctaaatcaaa gaattcatgg cagccaacta cgtttctcga      60
ttgttg                                                                 66

<210> SEQ ID NO 9
<211> LENGTH: 60
<212> TYPE: DNA
<213> ORGANISM: Artificial Sequence
<220> FEATURE:
<223> OTHER INFORMATION: PCR oligo-primer for ApuA_N-R

<400> SEQUENCE: 9
gactagaagg cttaatcaaa agctctcgag tcacccctgc caagtattgc tgaccgatgc      60

<210> SEQ ID NO 10
<211> LENGTH: 60
<212> TYPE: DNA
<213> ORGANISM: Artificial Sequence
<220> FEATURE:
<223> OTHER INFORMATION: PCR oligo-primer for ApuA_Opt-NatSS-L

<400> SEQUENCE: 10
tctctacttg accgggttgg tgcagtgttt gactccagct caatggagaa gtcaatctat      60

<210> SEQ ID NO 11
<211> LENGTH: 60
<212> TYPE: DNA
<213> ORGANISM: Artificial Sequence
<220> FEATURE:
<223> OTHER INFORMATION: PCR oligo-primer for ApuA_Opt-R

<400> SEQUENCE: 11
ggactagaag gcttaatcaa aagctctcga gctaaccttg ccatgtattg gagactgagg      60

<210> SEQ ID NO 12
<211> LENGTH: 55
<212> TYPE: DNA
<213> ORGANISM: Artificial Sequence
<220> FEATURE:
<223> OTHER INFORMATION: PCR oligo-primer for ApuA_optXynSec-L

<400> SEQUENCE: 12
gaacccgtgg ctgtggagaa gcgctcgcga ttgactccag ctcaatggag aagtc           55

<210> SEQ ID NO 13
<211> LENGTH: 60
<212> TYPE: DNA
<213> ORGANISM: Artificial Sequence
<220> FEATURE:
<223> OTHER INFORMATION: PCR oligo-primer for ApuA_Opt-R

<400> SEQUENCE: 13
ggactagaag gcttaatcaa aagctctcga gctaaccttg ccatgtattg gagactgagg      60

<210> SEQ ID NO 14
<211> LENGTH: 66
<212> TYPE: DNA
<213> ORGANISM: Artificial Sequence
<220> FEATURE:
<223> OTHER INFORMATION: PCR oligo-primer for AteA_Nat-L

<400> SEQUENCE: 14
```

```
tgcttatcaa cacacaaaca ctaaatcaaa gaattcatga agtggacctc ctcgctcctc      60
ctctta                                                                66

<210> SEQ ID NO 15
<211> LENGTH: 60
<212> TYPE: DNA
<213> ORGANISM: Artificial Sequence
<220> FEATURE:
<223> OTHER INFORMATION: PCR oligo-primer for AteA_Nat-R

<400> SEQUENCE: 15
gactagaagg cttaatcaaa agctctcgag tcacctccaa gtatcagcaa ctgtcaccgt      60

<210> SEQ ID NO 16
<211> LENGTH: 60
<212> TYPE: DNA
<213> ORGANISM: Artificial Sequence
<220> FEATURE:
<223> OTHER INFORMATION: PCR oligo-primer for TemA_Nat-L

<400> SEQUENCE: 16
tgcttatcaa cacacaaaca ctaaatcaaa gaattcatga cgcctttcgt cctcacggcc      60

<210> SEQ ID NO 17
<211> LENGTH: 60
<212> TYPE: DNA
<213> ORGANISM: Artificial Sequence
<220> FEATURE:
<223> OTHER INFORMATION: PCR oligo-primer for TemA_Nat-R

<400> SEQUENCE: 17
ggactagaag gcttaatcaa aagctctcga gctatctcca tgtgtcgaca atcgtctccg      60

<210> SEQ ID NO 18
<211> LENGTH: 60
<212> TYPE: DNA
<213> ORGANISM: Artificial Sequence
<220> FEATURE:
<223> OTHER INFORMATION: PCR oligo-primer for TemA_Opt-NatOptSS-L

<400> SEQUENCE: 18
tgcttatcaa cacacaaaca ctaaatcaaa gaattcatga ccccttttgt tttgacagcc      60

<210> SEQ ID NO 19
<211> LENGTH: 60
<212> TYPE: DNA
<213> ORGANISM: Artificial Sequence
<220> FEATURE:
<223> OTHER INFORMATION: PCR oligo-primer for TemA_Opt-R

<400> SEQUENCE: 19
ggactagaag gcttaatcaa aagctctcga gctatctcca agtgtcaaca atagtttcag      60

<210> SEQ ID NO 20
<211> LENGTH: 58
<212> TYPE: DNA
<213> ORGANISM: Artificial Sequence
<220> FEATURE:
<223> OTHER INFORMATION: PCR oligo-primer for TemA_Nat-xynsecSS-L

<400> SEQUENCE: 20
gaacccgtgg ctgtggagaa gcgctcgcga ttgaccccgg ccgaatggcg caaacaat        58

<210> SEQ ID NO 21
<211> LENGTH: 59
```

```
<212> TYPE: DNA
<213> ORGANISM: Artificial Sequence
<220> FEATURE:
<223> OTHER INFORMATION: PCR oligo-primer for TemA_Opt-xynsecSS-L

<400> SEQUENCE: 21
gaacccgtgg ctgtggagaa gcgctcgcga ttgacaccag ccgaatggag aaagcaatc       59

<210> SEQ ID NO 22
<211> LENGTH: 51
<212> TYPE: DNA
<213> ORGANISM: Artificial Sequence
<220> FEATURE:
<223> OTHER INFORMATION: PCR oligo-primer for TemA_Opt-NatSS-L

<400> SEQUENCE: 22
tcttgctggg gaatgccgtg ttggccttga caccagccga atggagaaag c               51

<210> SEQ ID NO 23
<211> LENGTH: 66
<212> TYPE: DNA
<213> ORGANISM: Artificial Sequence
<220> FEATURE:
<223> OTHER INFORMATION: PCR oligo-primer for AteG_Nat-L

<400> SEQUENCE: 23
tgcttatcaa cacacaaaca ctaaatcaaa gaattcatga cgcgcattct caccctcgcc      60
cttcat                                                                 66

<210> SEQ ID NO 24
<211> LENGTH: 61
<212> TYPE: DNA
<213> ORGANISM: Artificial Sequence
<220> FEATURE:
<223> OTHER INFORMATION: PCR oligo-primer for AteG_Nat-R

<400> SEQUENCE: 24
ggactagaag gcttaatcaa aagctctcga gctagcgcca agtggtgttc accaccgcgg      60
t                                                                      61

<210> SEQ ID NO 25
<211> LENGTH: 60
<212> TYPE: DNA
<213> ORGANISM: Artificial Sequence
<220> FEATURE:
<223> OTHER INFORMATION: PCR oligo-primer for AteG_Opt-NatSS-L

<400> SEQUENCE: 25
gggctggctc ttgtccaaag tgttgttggg gcaccacaat tggctcctag agcaactaca      60

<210> SEQ ID NO 26
<211> LENGTH: 60
<212> TYPE: DNA
<213> ORGANISM: Artificial Sequence
<220> FEATURE:
<223> OTHER INFORMATION: PCR oligo-primer for AteG_Opt-R

<400> SEQUENCE: 26
tggactagaa ggcttaatca aaagctctcg agctatctcc aggttgtgtt gacaacggcg      60

<210> SEQ ID NO 27
<211> LENGTH: 60
<212> TYPE: DNA
<213> ORGANISM: Artificial Sequence
<220> FEATURE:
```

<223> OTHER INFORMATION: PCR oligo-primer for AteG_Nat-xynSS-L

<400> SEQUENCE: 27
gaacccgtgg ctgtggagaa gcgctcgcga gctccccaat tggcccccag agcgacaacc     60

<210> SEQ ID NO 28
<211> LENGTH: 66
<212> TYPE: DNA
<213> ORGANISM: Artificial Sequence
<220> FEATURE:
<223> OTHER INFORMATION: PCR oligo-primer for TemG_Nat-L

<400> SEQUENCE: 28
tgcttatcaa cacacaaaca ctaaatcaaa gaattcatgg cgtccctcgt tgctggcgct     60
ctctgc                                                                66

<210> SEQ ID NO 29
<211> LENGTH: 61
<212> TYPE: DNA
<213> ORGANISM: Artificial Sequence
<220> FEATURE:
<223> OTHER INFORMATION: PCR oligo-primer for TemG_Nat-R

<400> SEQUENCE: 29
ggactagaag gcttaatcaa aagctctcga gtcactgcca actatcgtca agaatggcgg     60
t                                                                     61

<210> SEQ ID NO 30
<211> LENGTH: 60
<212> TYPE: DNA
<213> ORGANISM: Artificial Sequence
<220> FEATURE:
<223> OTHER INFORMATION: PCR oligo-primer for TemG_Nat-xynsecSS-L

<400> SEQUENCE: 30
gaacccgtgg ctgtggagaa gcgctcgcga cgagcgcccg ttgcagcgcg agccaccggt     60

<210> SEQ ID NO 31
<211> LENGTH: 60
<212> TYPE: DNA
<213> ORGANISM: Artificial Sequence
<220> FEATURE:
<223> OTHER INFORMATION: PCR oligo-primer for TemG_Opt-xynsecSS-L

<400> SEQUENCE: 31
gaacccgtgg ctgtggagaa gcgctcgcga agagccccag tcgcagccag agcaacaggt     60

<210> SEQ ID NO 32
<211> LENGTH: 60
<212> TYPE: DNA
<213> ORGANISM: Artificial Sequence
<220> FEATURE:
<223> OTHER INFORMATION: PCR oligo-primer for TemG_Opt-R

<400> SEQUENCE: 32
gactagaagg cttaatcaaa agctctcgag tcattgccaa gagtcgtcca agattgcggt     60

<210> SEQ ID NO 33
<211> LENGTH: 60
<212> TYPE: DNA
<213> ORGANISM: Artificial Sequence
<220> FEATURE:
<223> OTHER INFORMATION: PCR oligo-primer for TemG_Opt-NatOptSS-L

<400> SEQUENCE: 33
ttatcaacac acaaacacta aatcaaagaa ttcatggcct ccttagtcgc aggtgcctta    60

<210> SEQ ID NO 34
<211> LENGTH: 60
<212> TYPE: DNA
<213> ORGANISM: Artificial Sequence
<220> FEATURE:
<223> OTHER INFORMATION: PCR oligo-primer for TemG_Opt-NatSS-L

<400> SEQUENCE: 34
atcctgggcc tgacgcctgc tgcatttgca agagccccag tcgcagccag agcaacaggt    60

<210> SEQ ID NO 35
<211> LENGTH: 58
<212> TYPE: DNA
<213> ORGANISM: Artificial Sequence
<220> FEATURE:
<223> OTHER INFORMATION: PCR oligo-primer ENOCASS-L

<400> SEQUENCE: 35
gtgcggtatt tcacaccgca taggagatcg atcccaatta atgtgagtta cctcactc      58

<210> SEQ ID NO 36
<211> LENGTH: 35
<212> TYPE: DNA
<213> ORGANISM: Artificial Sequence
<220> FEATURE:
<223> OTHER INFORMATION: PCR oligo-primer ENOCASS-R

<400> SEQUENCE: 36
cgggcctctt cgctattacg ccagagctta gatct                               35

<210> SEQ ID NO 37
<211> LENGTH: 62
<212> TYPE: DNA
<213> ORGANISM: Artificial Sequence
<220> FEATURE:
<223> OTHER INFORMATION: PCR primer amdSYMCas-L

<400> SEQUENCE: 37
ccgcgcgttg gccgattcat taatccagga tccacatgga ggcccagaat accctccttg    60
ac                                                                   62

<210> SEQ ID NO 38
<211> LENGTH: 64
<212> TYPE: DNA
<213> ORGANISM: Artificial Sequence
<220> FEATURE:
<223> OTHER INFORMATION: PCR primer amdSYMCas-R

<400> SEQUENCE: 38
gggcctcttc gctattacgc cagagcttag atctcagtat agcgaccagc attcacatac    60
ttaa                                                                 64

<210> SEQ ID NO 39
<211> LENGTH: 128
<212> TYPE: DNA
<213> ORGANISM: Artificial Sequence
<220> FEATURE:
<223> OTHER INFORMATION: PCR primer Delta-ENO1p-L

<400> SEQUENCE: 39
tggaataaaa atccactatc gtctatcaac taatagttat attatcaata tattatcata    60

```
tacggtgtta agatgatgac ataagttatg agaagctgtc ggatcccaat taatgtgagt    120
tacctcac                                                              128

<210> SEQ ID NO 40
<211> LENGTH: 128
<212> TYPE: DNA
<213> ORGANISM: Artificial Sequence
<220> FEATURE:
<223> OTHER INFORMATION: PCR primer Delta-ENO1t-R

<400> SEQUENCE: 40
tgagatatat gtgggtaatt agataattgt tgggattcca ttgttgataa aggctataat    60
attaggtata cagaatatac tagaagttct cctcgaggat agatctccta tgcggtgtga    120
aataccgc                                                              128

<210> SEQ ID NO 41
<211> LENGTH: 60
<212> TYPE: DNA
<213> ORGANISM: Artificial Sequence
<220> FEATURE:
<223> OTHER INFORMATION: PCR primer TemG_Opt-L

<400> SEQUENCE: 41
ttatcaacac acaaacacta aatcaaagaa ttcatggcct ccttagtcgc aggtgcctta    60

<210> SEQ ID NO 42
<211> LENGTH: 60
<212> TYPE: DNA
<213> ORGANISM: Artificial Sequence
<220> FEATURE:
<223> OTHER INFORMATION: PCR primer TemG_Opt-R

<400> SEQUENCE: 42
gactagaagg cttaatcaaa agctctcgag tcattgccaa gagtcgtcca agattgcggt    60

<210> SEQ ID NO 43
<211> LENGTH: 60
<212> TYPE: DNA
<213> ORGANISM: Artificial Sequence
<220> FEATURE:
<223> OTHER INFORMATION: PCR primer TemA_Nat-L

<400> SEQUENCE: 43
tgcttatcaa cacacaaaca ctaaatcaaa gaattcatga cgcctttcgt cctcacggcc    60

<210> SEQ ID NO 44
<211> LENGTH: 60
<212> TYPE: DNA
<213> ORGANISM: Artificial Sequence
<220> FEATURE:
<223> OTHER INFORMATION: PCR primer TemA_Nat-R

<400> SEQUENCE: 44
ggactagaag gcttaatcaa aagctctcga gctatctcca tgtgtcgaca atcgtctccg    60

<210> SEQ ID NO 45
<211> LENGTH: 21
<212> TYPE: DNA
<213> ORGANISM: Artificial Sequence
<220> FEATURE:
<223> OTHER INFORMATION: PCR primer URA3-L

<400> SEQUENCE: 45
cgtggatgat gtggtctcta c                                               21
```

```
<210> SEQ ID NO 46
<211> LENGTH: 22
<212> TYPE: DNA
<213> ORGANISM: Artificial Sequence
<220> FEATURE:
<223> OTHER INFORMATION: PCR primer URA3-R

<400> SEQUENCE: 46
gttcaccctc taccttagca tc                                            22

<210> SEQ ID NO 47
<211> LENGTH: 22
<212> TYPE: DNA
<213> ORGANISM: Artificial Sequence
<220> FEATURE:
<223> OTHER INFORMATION: PCR primer temA_Nat-L

<400> SEQUENCE: 47
gcgatgtcac tgagaggatc ta                                            22

<210> SEQ ID NO 48
<211> LENGTH: 20
<212> TYPE: DNA
<213> ORGANISM: Artificial Sequence
<220> FEATURE:
<223> OTHER INFORMATION: temA_Nat-R

<400> SEQUENCE: 48
gaaatccaga tggccgtgaa                                               20

<210> SEQ ID NO 49
<211> LENGTH: 20
<212> TYPE: DNA
<213> ORGANISM: Artificial Sequence
<220> FEATURE:
<223> OTHER INFORMATION: PCR primer temG_Opt-L

<400> SEQUENCE: 49
tacaggtggt ttgggtgaac                                               20

<210> SEQ ID NO 50
<211> LENGTH: 21
<212> TYPE: DNA
<213> ORGANISM: Artificial Sequence
<220> FEATURE:
<223> OTHER INFORMATION: PCR primer temG_Opt-R

<400> SEQUENCE: 50
ctctcaatgc tggaccatct c                                             21
```

RECOMBINANT YEAST AND USE THEREOF

CROSS-REFERENCE TO RELATED APPLICATION

This application claims the benefit of priority of United Kingdom Application No. GB 1 620 658.3, filed Dec. 5, 2016, which is incorporated by reference herein in its entirety for any purpose.

SEQUENCE LISTING

The present application is filed with a Sequence Listing in electronic format. The Sequence Listing is provided as a file entitled "2017-12-04_01204-0001-00US_P3338US_ST25.txt" created on Nov. 27, 2017, which is 34,663 bytes in size. The information in the electronic format of the sequence listing is incorporated herein by reference in its entirety.

FIELD OF THE INVENTION

The invention relates to a recombinant yeast for converting raw and soluble starch to an alcohol such as ethanol, particularly for use as a biofuel.

BACKGROUND TO THE INVENTION

Cost effective, renewable and sustainable energy is a global concern, which has increased investigations into alternative fuel sources. Starch-rich biomass together with sugarcane represents the main substrates for bioethanol production (Bai et al., 2008). It is produced by plants as an energy store and consists of α-1,4 linked glucose units with α-1,6 branching points. The amylose and amylopectin polymers are densely packed in starch granules forming a semi-crystalline structure with inter- and intra-molecular bonds.

A combination of α-amylases and glucoamylases is required for the complete hydrolysis of starch. Starch granules are insoluble in cold water and are often resistant to enzymatic hydrolysis (Uthumporn et al., 2010). The conventional process for the conversion of starch to ethanol requires a heat intensive liquefaction step to gelatinise the starch and thermostable α-amylases, followed by saccharification with glucoamylases. The high temperatures required for the initial processes usually account for approximately 30-40% of the total energy required for ethanol production (Szymanowska-Powalowska et al., 2012).

An alternative to this is a cold hydrolysis process at temperatures below the onset of starch gelatinization (65° C. for corn) (Robertson et al., 2006). Benefits of this process include reduced energy requirements and a higher nutritional content for the dried distillers' grains with solubles (DDGS) (Nkomba et al., 2016). DDGS are produced in large quantities during bioethanol production and represent a valuable ingredient for livestock feed (Brehmer et al., 2008).

Consolidated bioprocessing (CBP) combines enzyme production, hydrolysis and fermentation into a one-step process for bioethanol production at low temperatures. This technology represents a promising alternative for the economic production of biofuel from lignocellulosic and starchy feedstocks. CBP could simplify operational processes (e.g. number of control steps and reaction vessels) and therefore reduce maintenance and production costs. CBP systems use a single organism that is able to produce the enzymes required for hydrolysis of starch at low temperatures, i.e. cold hydrolysis, as well as convert the resultant sugars to ethanol. The cold process requires amylases that have the ability to digest raw starch efficiently at fermentation conditions. A few raw starch hydrolyzing amylases have been reported to date (Mamo and Gessesse, 1999; Robertson et al., 2006; Celińska et al., 2015). These amylases differ from conventional amylases in their affinity and interaction with the microcrystalline structures of starch granules. A starch binding domain (SBD) is a key characteristic of these enzymes and enables them to bind effectively to the surface of raw starch granules.

A comprehensive review on consolidated bioprocessing systems by Salehi Jouzani and Taherzadeh (2015) highlighted different CBP strategies, diversity in substrate types and the organisms involved in fermenting the sugars. One of the main challenges remains the simultaneous production of the amylases with high substrate affinities and specific activity (den Haan et al., 2013). In addition, fermentation requirements are ethanol concentrations in excess of 10-12% ($w \cdot v^{-1}$) within 48 to 72 hours (Bothast and Schlicher, 2005). For example, raw starch amylase encoding genes from *Lipomyces kononenkoae* and *Saccharomycopsis fibuligera* (Eksteen et al., 2003; Knox et al., 2004), *Rhizopus arrhizus* (Yang et al., 2011), *Aspergillus tubingensis* (Viktor et al., 2013) and *Thermomyces lanuginoses* and *S. fibuligera* or *L. kononenkoae* (LKA1) protein (U.S. Pat. No. 9,243,256) have been expressed in *Saccharomyces cerevisiae*, a yeast which is an efficient ethanol producer but which on its own lacks the ability to degrade starch.

However, none of these transformed yeasts produce sufficient amounts of amylase to support efficient conversion of raw starch to ethanol in a single step at commercial scale. Although a bioengineered *S. cerevisiae* strain that secretes a glucoamylase is commercially available (TransFerm® from Lallemand (www.ethanoltech.com/transferm)), it lacks the required α-amylase enzymes for starch liquefaction (den Haan et al., 2015) and is therefore only a semi-CBP yeast. The TransFerm® yeast strain is thus only suitable for the conventional (warm) process, as it only consolidates the saccharification and fermentation processes after starch liquefaction. CBP has therefore not yet been implemented on a commercial level, with the main challenge being the availability of a microorganism that can express suitable enzymes and have a high fermentation capacity.

Other cold simultaneous saccharification and fermentation (SSF) processes have been developed for ethanol production from starchy substrates (Balcerek and Pielech-Przybylska, 2013; Szymanowska-Powalowska et al., 2014; Nkomba et al., 2016). In these processes, granular starch hydrolyzing enzyme (GSHE) cocktails are added to the feedstock in addition to the yeast. Genencor's STARGEN 001™ and STARGEN 002™ cocktails (Dupont-Danisco, Itasca, Itasca) hydrolyse raw starch at low temperatures (48° C. recommended for SSF), while POET (Sioux Falls, South Dakota, USA) uses a patented blend of Novozymes enzymes (POET BPX technology) in an SSF process (Görgens et al., 2015). However, these cold starch hydrolysis processes require high enzyme loadings and the cost of the commercial enzymes, e.g. STARGEN™ (Genencor International, California, USA), is high.

There thus remains a need for a yeast which can be used in a CBP process for producing ethanol from raw starch, without requiring the addition of amylases from a source other than the yeast.

SUMMARY OF THE INVENTION

According to a first embodiment of the invention, there is provided a recombinant yeast which has been transformed with:

a) a first heterologous gene which encodes an α-amylase comprising an amino acid sequence which is at least 70% identical to SEQ ID NO: 1, wherein the nucleic acid sequence of the first gene is not codon-optimized; and
b) a second heterologous gene which encodes a glucoamylase comprising an amino acid sequence which is at least 70% identical to SEQ ID NO: 2, wherein the nucleic acid sequence of the second gene is optionally codon-optimized.

The amino acid sequence of the α-amylase may be at least 80% identical to SEQ ID NO: 1; the amino acid sequence of the α-amylase may be at least 90% identical to SEQ ID NO: 1; or the amino acid sequence of the α-amylase may be identical to SEQ ID NO: 1.

The amino acid sequence of the glucoamylase may be at least 80% identical to SEQ ID NO: 2; the amino acid sequence of the glucoamylase may be at least 90% identical to SEQ ID NO: 2; or the amino acid sequence of the glucoamylase may be identical to SEQ ID NO: 2.

The nucleic acid sequence of the first heterologous gene may be at least 70% identical to SEQ ID NO: 3, at least 80% identical to SEQ ID NO: 3, at least 90% identical to SEQ ID NO: 3, or may be identical to SEQ ID NO: 3.

The nucleic acid sequence of the second heterologous gene may be at least 70% identical to either of SEQ ID NOS: 4 and 5, depending on whether the sequence has been codon-optimized or not; and may be at least 80% identical to either of SEQ ID NOS: 4 and 5, at least 90% identical to either of SEQ ID NOS: 4 and 5, or may be identical to either of SEQ ID NOS: 4 and 5.

The yeast may be a *Saccharomyces* species, such as *Saccharomyces cerevisiae*.

The yeast may be a yeast which is capable of converting sugars such as glucose to alcohol.

The alcohol may be butanol or ethanol, and in particular is ethanol.

The recombinant yeast may be capable of hydrolyzing raw starch in the absence of enzymes from a source other than the recombinant yeast. The raw starch may be hydrolysed at a temperature of about 40° C. or lower.

According to a second embodiment of the invention, there is provided a process for producing an alcohol from sugars, the process comprising the step of using a recombinant yeast as described above to convert the sugars to alcohol.

The sugars may comprise glucose.

The alcohol may be ethanol or butanol, and is typically ethanol.

According to a third embodiment of the invention, there is provided a process for producing an alcohol from starch, the process comprising the step of using a recombinant yeast as described above to convert the starch to alcohol.

The recombinant yeast may be added to a composition comprising starch or sugars, and may be allowed to express and secrete (i) an α-amylase comprising an amino acid sequence which is at least 70% identical to SEQ ID NO: 1 and (ii) a glucoamylase comprising an amino acid sequence which is at least 70% identical to SEQ ID NO: 2, so that saccharification and/or fermentation of the starch and/or sugars occurs so as to produce an alcohol.

The starch may be a grain starch.

The starch may be raw (granular) starch or may be soluble (cooked) starch.

The raw starch may be hydrolysed by the recombinant yeast without requiring cooking of the starch. For example, the raw starch may be hydrolysed by the recombinant yeast at a temperature of about 40° C. or lower.

The alcohol may be ethanol or butanol, and is typically ethanol.

The process may be a Consolidated Bioprocessing (CBP) process for producing a biofuel.

Enzymes exogenous to the recombinant yeast may also be added to the composition. The exogenous enzymes may be added in an amount which is at least 50% less than the amount of enzymes added to cold hydrolysis processes which do not use the recombinant yeast of the invention.

According to a further embodiment of the invention, there is provided the use of a recombinant yeast as described above in a method of producing an alcohol from starch or sugars.

The alcohol may be a biofuel.

BRIEF DESCRIPTION OF THE FIGURES

FIG. 15 Ethanol concentrations produced by S. cerevisiae Ethanol Red™ strains with different enzyme ratios at a fermentation temperature of 30° C. (total inoculum volume was 10% (v·v$^{-1}$)). Untransformed Ethanol Red™+28 μl STARGEN™ (-▲-), Ethanol Red™ TemA_Nat+28 μl STARGEN™ (-◆-), Ethanol Red™ TemA_Nat+5 μl (-●-), 10 μl (-▼-) and 20 μl (-■-) commercial glucoamylase, respectively, untransformed Ethanol Red™+10 μl commercial glucoamylase (-●-) and 10 ml Ethanol Red™ T12 (-○-).

FIG. 16 SEQ ID NO: 1:—TemA protein. Protein sequence of Rasamsonia emersonii alpha-amylase. [Rasamsonia emersonii CBS 393.64] Sequence ID: GenBank no. XP_013324946.

FIG. 17 SEQ ID NO: 2:—TemG protein. Protein sequence of Rasamsonia emersoni glucoamylase (secretion signal underlined). Sequence ID: CAC28076.1.

FIG. 18 SEQ ID NO: 3:—temA_Nat gene. Synthetic DNA sequence coding for the Rasamsonia emersoni alpha-amylase (putative secretion signal underlined) used to produce TemA_Nat. This is 99% identical to Rasamsonia emersonii CBS 393.64 alpha-amylase mRNA NCBI Reference Sequence: Genbank no. XM_013469492 (1 nucleotide was changed, compared to the original GenBank sequence, without affecting the protein sequence).

FIG. 19 SEQ ID NO: 4: temG_Opt. DNA sequence coding for the Rasamsonia emersonii glucoamylase (putative secretion signal underlined), optimized for expression in S. cerevisiae (by GenScript, USA).

FIG. 20 SEQ ID NO: 5: temG_Nat gene. Adapted native DNA sequence coding for the Rasamsonia emersonii glucoamylase (TemG_Nat). This sequence contained 3 nucleotide changes (bold and underlined) compared to the original GenBank sequence (introns removed) and the protein sequence is TemG.

FIG. 21 SEQ ID NO: 6 temA—original Genbank sequence for native Rasamsonia emersonii CBS 393.64 Alpha-amylase mRNA NCBI Reference Sequence: XM_013469492.1

FIG. 22 SEQ ID NO: 7: temG—original Talaromyces emersonii ga gene for glucoamylase, exons 1-5 (Genbank sequence including introns; GenBank: AJ304803.1).

DETAILED DESCRIPTION OF THE INVENTION

Figure 1:
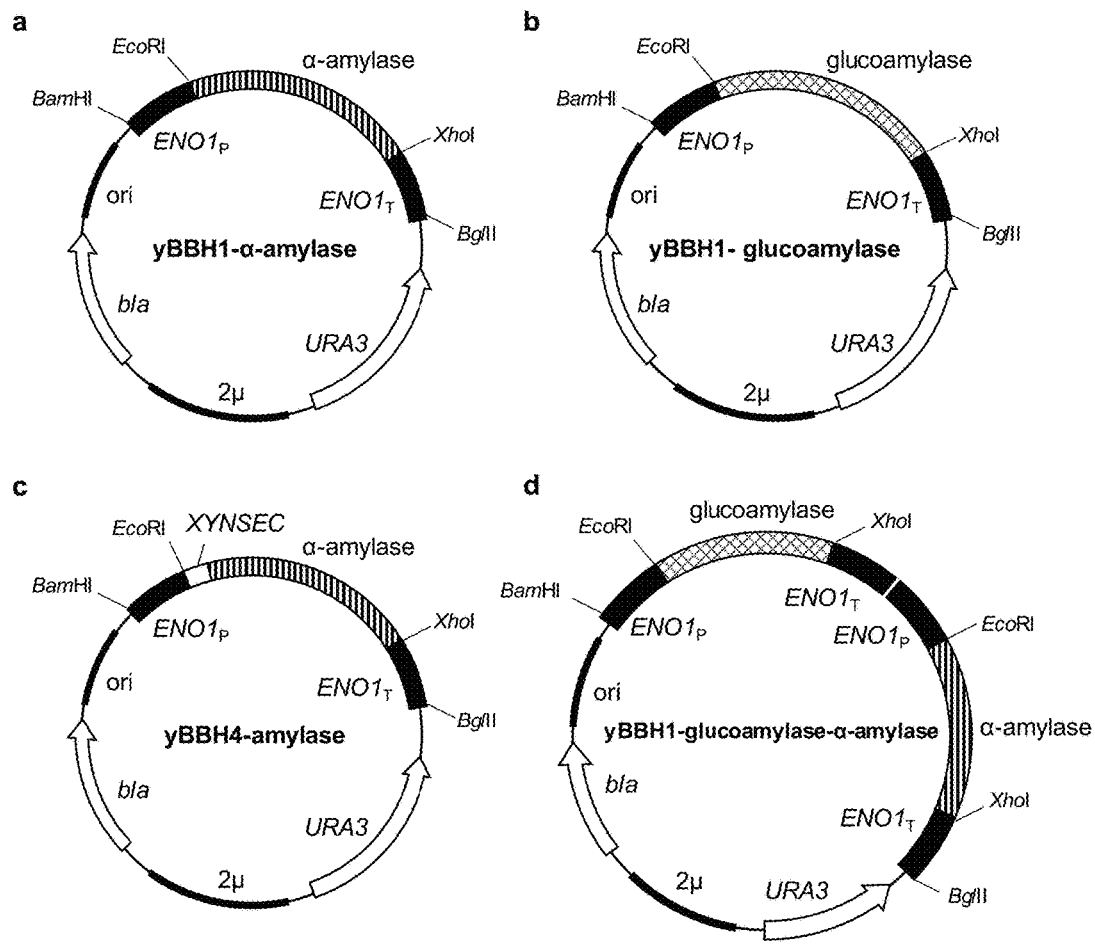
FIG. 1 Schematic representation of the vector constructs used in example 1. Amylase encoding genes were amplified using PCR and respectively cloned onto the yBBH1 and yBBH4 vectors (a, b and c). The ENO1$_P$-α-amylases-ENO1$_T$ cassettes were cloned onto the yBBH1-glucoamylase plasmids (d), to enable co-expression of the genes. BamHI and BglII restriction enzyme sites were used for yeast mediated ligation (YML).

A recombinant yeast that expresses both an α-amylase and a glucoamylase from Talaromyces emersonii (recently re-named as Rasamsonia emersonii) is provided. The α-amylase comprising an amino acid sequence which is at least 70% identical to SEQ ID NO: 1 and the glucoamylase comprises an amino acid sequence which is at least 70% identical to SEQ ID NO: 2. The recombinant yeast can be used for converting starches and sugars to an alcohol, in particular for use as a biofuel.

The amino acid sequence of the α-amylase can be at least 80% identical to SEQ ID NO: 1. The amino acid sequence of the α-amylase can also at least 90% identical to SEQ ID NO: 1; or the amino acid sequence of the α-amylase can also be identical to SEQ ID NO: 1.

The amino acid sequence of the glucoamylase can be at least 80% identical to SEQ ID NO: 2; the amino acid sequence of the glucoamylase can be at least 90% identical to SEQ ID NO: 2; or the amino acid sequence of the glucoamylase can be identical to SEQ ID NO: 2.

The yeast can be transformed with the native genes for both of these enzymes or with a codon-optimized gene for the glucoamylase. Nucleotide changes may also be made to the native gene so as to disrupt restriction sites for cloning purposes, but without altering the protein sequence (for example, as shown in FIGS. 19 and 20).

The nucleic acid sequence of the first heterologous gene can be at least 70% identical to SEQ ID NO: 3, at least 80% identical to SEQ ID NO: 3, at least 90% identical to SEQ ID NO: 3, or can be identical to SEQ ID NO: 3.

In one embodiment, the yeast is transformed with a codon-optimized gene for the glucoamylase, which has 69% identity to the native sequence. In this embodiment, the yeast is transformed with a glucoamylase which comprises a nucleic acid sequence which is at least 68% similar to, at least 70% similar to, at least 80% similar to, at least 90% similar to, or identical to SEQ ID NO: 4.

In another embodiment, instead of the yeast being transformed with the codon-optimized glucoamylase, it can be transformed with a non-codon-optimized glucoamylase comprising a nucleic acid sequence which is at least 70% similar to, at least 80% similar to, at least 90% similar to, or identical to SEQ ID NO: 5.

The host yeast can be selected from those yeasts which are capable of converting sugars to alcohol. Such sugars could be derived from hydrolysed starch or other abundant hexose sugar-rich feedstocks.

Exemplary yeasts for the present invention are *Pichia* (*Hansenula*) spp. (e.g. *P. anomala, P. capsulate* and *P. angusta* (formerly *H. polymorpha*)), *Saccharomyces* spp. (e.g. *S. cerevisiae, S. italicus* and *S. rouxii*), *Yarrowia* (e.g. *Y. lipolytica*), *Kluyveromyces* spp. (e.g. *K. fragilis* and *K. lactis*), *Candida* spp. (e.g. *C. tropicales*), *Torulopsis* spp., *Torulaspora* spp., *Schizosaccharomyces* spp. (e.g *S. pombe*), *Citeromyces* spp., *Pachysolen* spp., *Debaromyces* spp., *Metschunikowia* spp., *Rhodosporidium* spp., *Leucosporidium* spp., *Botryoascus* spp., *Sporidiobolus* spp., *Endomycopsis* spp., *Schwanniomyces* spp. (e.g. *S. occidentalis*) and the like.

In one embodiment, the yeast is a *Saccharomyces* species, and in particular, *Saccharomyces cerevisiae*.

The yeast can be an industrial yeast, i.e. one that has been developed for the industrial ethanol industry. Such yeasts typically have one or more of the following properties: high ethanol tolerance, fast acting, high alcohol yields, high cell viability during fermentation, activity under a wide range of fermentation conditions, etc. One example of such a yeast is Ethanol Red™ from Fermentis (www.fermentis.com). Another example is the *S. cerevisiae* M2n strain, which is a South African distillery yeast. However, it will be apparent to a person skilled in the art that other industrial yeasts could also be used.

The yeast is typically transformed without integration of any antibiotic resistance gene (i.e. markerless integration).

Optionally, multiple copies of the α-amylase or glucoamylase can be integrated into the genome of the yeast, e.g. the yeast can be transformed with two or three copies of the α-amylase and/or two or three copies of the glucoamylase. In one particular embodiment, the recombinant strain contains one copy of the gene encoding the α-amylase and two copies of the gene encoding the glucoamylase.

The recombinant yeast can hydrolyse raw starch without requiring the use of additional enzymes (e.g. exogenous amylase). The raw starch can be hydrolysed at a temperature of about 40° C. or lower, such as from ambient temperature to about 40° C.

The recombinant yeast can be used in a single-step process for producing an alcohol from a starch. This process can be for producing a biofuel, but it can also be a process for manufacturing an alcoholic beverage, such as a beer. The alcohol can be butanol or ethanol. In one embodiment, the alcohol is ethanol.

As raw starch can be hydrolysed by the recombinant yeast, this can be used as the substrate without the need for an initial liquefaction step. However, soluble (or cooked) starch could also be used as the initial substrate.

The recombinant yeast can also be used in a process for producing an alcohol from sugars. The sugars can be derived from hydrolysed starch, from other abundant hexose sugar-rich feedstocks (e.g. sugarcane) or from cellulose-derived sugar streams (i.e. with the addition of cellulase enzymes). The sugars may comprise glucose.

Although the recombinant yeast of the invention is capable of hydrolyzing raw starch in the absence of an exogenous amylase, in some embodiments additional enzymes can be added to the fermentation process so as to reduce the fermentation time and/or increase the carbon conversion. These enzymes can be a glucoamylase, an amyloglucosidase (E.C. 3.2.1.3), an α-amylase, or a mixture thereof which can hydrolyse raw starch. For example, a cocktail of enzymes (*Aspergillus kawachii* α-amylase expressed in *Trichoderma reesei* and a glucoamylase from *T. reesei*) is available under the brand name STARGEN™ from Genencor International. As the recombinant yeast is able to continually replenish the enzymes in the fermentation broth, when exogenous enzymes are added to a cold fermentation process using the recombinant yeast of the invention, they can be added in a reduced amount compared to the dosage that would be required if a different yeast was being used (e.g. the Transferm™ yeast from Lallemand). For example, the exogenous enzymes can be added in an amount which is about 50% to about 95% less than the dosage which is used in commercial cold fermentation processes. In particular, the applicant has found that the addition of exogenous enzymes in combination with the recombinant amylolytic yeast of the invention allowed for a 90% reduction in the enzyme dosage, compared to the conventional simultaneous saccharification (SSF) process with untransformed host strains.

The single step saccharification and fermentation process may be performed at temperatures ranging from ambient (room) temperature to about 40° C. More particularly, the temperature can be from about 30° C. to about 37° C.

Alpha-amylases and glucoamylases from *Aspergillus terreus, Aureobasidium pullulans, Chaetomium thermophilum, Humicola grisea, Neosartorya fischeri, Rhizomucor pusillus, Talaromyces emersonii, Talaromyces stipitatus* and *Thermomyces lanuginosus* were screened for activity on starch and compared to the *S. cerevisiae* Y294[AmyA] and Y294[GlaA] benchmark strains, respectively (Viktor et al., 2013). Thereafter, several different amylolytic *S. cerevisiae* Y294 strains (ATCC 201160) were constructed and compared to the *S. cerevisiae* Y294[AmyA-GlaA] benchmark strain (Viktor et al., 2013) for their ability to hydrolyse raw corn starch and ferment the resulting glucose to ethanol at a high substrate loading (200 g·l$^{-1}$ raw corn starch).

A combination of a glucoamylase from *T. emersonii* (TemG (SEQ ID NO: 2)) and an α-amylase from *T. emersonii* (TemA (SEQ ID NO: 1)) was found to be the most efficient at hydrolyzing raw corn starch at fermentation conditions. *T. emersonii* is a thermophilic fungus that is industrially important and well recognised for its production of glycoside hydrolases (GHs) with special enzymatic properties, especially cellulases (Amore and Faraco, 2012; Wang et al., 2014). However, few studies have investigated its starch hydrolyzing enzymes. *T. emersonii* amylases have also not previously been expressed in *S. cerevisiae*.

Further investigations showed that when these enzymes were expressed in yeast, a combination of the codon-optimized glucoamylase gene (temG_Opt (SEQ ID NO: 4)) and native α-amylase gene (temA_Nat (SEQ ID NO: 3)) provided even better results than when the native glucoamylase gene (temG_Nat (SEQ ID NO: 5)) was used or when both genes had been codon optimized. For example, the recombinant *S. cerevisiae* Y294[TemG_Opt-TemA_Nat] strain expressing the codon-optimized glucoamylase and native α-amylase from *T. emersonii* produced 51.7 g·l$^{-1}$ ethanol from raw starch after 120 hours of fermentation compared to 33.1 g·l$^{-1}$ produced by the *S. cerevisiae* Y294 [AmyA-GlaA] benchmark strain. The *S. cerevisiae* Y294 [TemG_Opt-TemA_Nat] strain displayed an 85% carbon conversion after 192 hours, compared to the 54% by the benchmark strain.

The codon-optimized *T. emersonii* glucoamylase gene (temG_Opt (SEQ ID NO: 4)) and native *T. emersonii* α-amylase gene (temA_Nat (SEQ ID NO: 3)) were then transformed into two commercially available industrial *S. cerevisiae* strains, namely Ethanol Red™ and the M2n (MH-1000) distillery yeast (Favaro et al., 2015). Ethanol Red™ is one of the most widely used yeast strains for first generation bioethanol production (Stovicek et al., 2015). Few studies have engineered *S. cerevisiae* Ethanol Red™ for the expression of gene cassettes or adapted it for desired characteristics. Demeke et al. (2013b) developed a D-xylose fermenting strain, Wallace-Salinas and Gorwa-Grauslund (2013) developed a strain capable of growing and fermenting spruce hydrolysate and Stovicek et al. (2015b) introduced a xylose consumption pathway into Ethanol Red™. To the applicant's knowledge, this study is the first to engineer *S. cerevisiae* Ethanol Red™ for the expression of both an α-amylase and glucoamylase for efficient raw starch conversion.

Two δ-integration gene cassettes were constructed to allow for the simultaneous multiple integration of the codon-optimized *T. emersonii* glucoamylase gene (temG_Opt) and the native *T. emersonii* α-amylase gene (temA_Nat) into the genomes of the yeasts. The *T. emersonii* amylases were both constitutively expressed under the control of the ENO1 promoter, using the δ-integration DNA transformation system. The amylolytic industrial strains were evaluated at high solids loadings and were able to ferment starch to ethanol in a single step with ethanol yields close to the theoretical maximum yield. After 192 hours at 30° C., the *S. cerevisiae* Ethanol Red™ T12 and M2n T1 strains (containing integrated temA_Nat and temG_Opt gene cassettes) produced 86.45 g·l$^{-1}$ and 99.40 g·l$^{-1}$ ethanol, respectively, corresponding to a carbon conversion of 83.98% and 95.56%, respectively. In a 5-liter bioreactor, the *S. cerevisiae* Ethanol Red™ T12 strain produced 82.6 g·l$^{-1}$ ethanol at 37° C. after 192 hours, which corresponded to 79% of the theoretical ethanol yield.

The recombinant yeasts described herein can achieve a carbon conversion of greater than 70% (w/w), preferably of greater than 80%, and even more preferably of 90% or greater. Theoretical ethanol yields are greater than 90%. Importantly, it was also shown that transforming the host yeast with the α-amylase and glucoamylase genes does not impede the robustness of the host strain.

Thus, the recombinant yeasts of the invention are better and more efficient than known benchmark strains for producing alcohol from raw starch, and are also robust and thermotolerant. The recombinant yeasts are therefore promising candidates for use in simultaneous saccharification and fermentation (SSF) or consolidated bioprocessing (CBP) processes. They represent a novel alternative for reducing or avoiding the enzyme dosage required for raw starch hydrolysis, as well as being able to provide continuous amylolytic activity for a continuous cold fermentations process. It is therefore envisaged that the recombinant yeast strain of the invention could be used in commercial hot (cooked starch) and cold fermentation processes that are currently used by ethanol producers (i.e. as a "drop in candidate").

It is also envisaged that the use of recombinant yeasts of the present invention will yield more cost-effective ethanol production from starchy feedstocks.

Glossary of Terms

As used herein, the singular forms "a", "an" and "the" include the plural references unless the content clearly dictates otherwise. Thus for example, reference to a composition containing "a compound" includes a reference to a mixture of two or more compounds. It should be noted that the term "or" is generally employed in the sense including "and/or" unless the context dictates otherwise.

The term "about" as used in relation to a numerical value means, for example, within 50% (±50%) of the numerical value, preferably ±30%, +20%, +15%, +10%, +7%, +5%, or +1%. Where necessary, the word "about" may be omitted from the definition of the invention.

The term "comprising" means "including". Thus, for example, a composition or polypeptide "comprising" X may consist exclusively of X or may include one or more additional components. In some embodiments, "comprising" means "including principally, but not necessarily solely".

As used herein, "heterologous" in reference to a nucleic acid or protein includes a molecule that has been manipulated by human intervention so that it is located in a place other than the place in which it is naturally found. For example, a nucleic acid sequence from one organism (e.g. from one strain or species) may be introduced into the genome of another organism (e.g. of another strain or species). A heterologous protein includes, for example, a protein expressed from a heterologous coding sequence or a protein expressed from a recombinant gene in a cell that would not naturally express the protein.

The terms "polypeptide" and "protein" are used interchangeably.

The term "alpha-amylase" refers to the EC 3.2.1.1 class of enzymes (1,4-alpha-D-glucan glucanohydrolase) which catalyse the hydrolysis of alpha-1,4-glucosidic linkages. The enzymes are endo-hydrolases, employ a retaining mechanism for hydrolysis (Enzyme Nomenclature, 1992) and belong to the glycoside hydrolase (GH) Family 13 and clan GH-H (MacGregor et al., 2001). They hydrolyse the 1,4-alpha-D-glucosidic linkages in polysaccharides containing three or more 1,4-alpha-linked D-glucose units. Hydrolysis reduces the molecular size of starch and therefore the viscosity of the starch solution. The alpha-amylases have considerably low sequence similarity.

Glucoamylases (glucan α-1,4-glucosidase, EC 3.2.1.3) belong to GH Family 15. Glucoamylases are exo-acting enzymes which catalyse the hydrolysis of α-1,4- and α-1,6-glucosidic linkages, thereby releasing the inverted β-d-glucose from the non-reducing ends of starch.

Further information of the structure and function of glucoamylases and alpha-amylases may be found in Christiansen et al. FEBS Journal 276 (2009) 5006-5029.

The phrases "percent identity", "% identity," "protein identity", "sequence identity" etc. as applied to polypeptide sequences, refer to the percentage of identical residue matches between at least two polypeptide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity may be determined using one or more computer algorithms or programs known in the art. For example, the UWGCG Package provides the BESTFIT program which can be used to calculate sequence identity (for example used on its default settings) (Devereux et al. (1984) Nucleic Acids Research 12, p 387-395). The PILEUP and BLAST (Basic Local Alignment Search Tool) algorithms can be used to calculate sequence identity or line up sequences (typically on their default settings), for example as described in Altschul S. F. (1993) J Mol Evol 36:290-300 and in Altschul, S, F et al. (1990) J Mol Biol 215:403. Software for performing BLAST analyses is available from several sources, including the National Center for Biotechnology Information (NCBI), Bethesda, Md., and on the internet at, for example, "www.ncbi.nlm.nih.gov/". Preferably, the default settings of the aforementioned algorithms/programs are used.

Whether an amino acid can be substituted at all (or deleted), or whether it can only be substituted by a conserved amino acid can be determined by comparing the amino acid sequence of one or more members of the protein family. Amino acids that are identical in all the members of a protein family often cannot be substituted. Amino acids which are conserved can usually be substituted by other conserved amino acids without significantly affecting the protein's function. Amino acids which are not conserved within a family can usually be freely substituted. Guidance in determining which amino acid residues may be substituted, inserted, or deleted without abolishing biological activity may also be found using computer programs well known in the art, for example, LASERGENE software (DNASTAR). Guidance concerning how to make phenotypically silent amino acid substitutions is provided, for example, in J. U. Bowie et al., "Deciphering the Message in Protein Sequences: Tolerance to Amino Acid Substitutions," Science 247:1306-1310 (1990). Also, it will be recognized by those skilled in the art that there may be critical areas on the protein which determine activity, such as the starch binding domain (SBD) and catalytic domain. The skilled person will appreciate that it may be desirable to take into account these areas when determining what changes to the amino acid sequence can be made. A detailed overview of SBDs may be found in Machovič and Janeč, 2006. Amino acid residues essential to activity of the polypeptide, and therefore preferably not subject to alteration e.g. by substitution or deletion (or if substituted only substituted by conservative substitutions), may be identified according to procedures known in the art, such as site-directed mutagenesis or alanine-scanning mutagenesis (see, e.g., Cunningham and Wells, 1989, Science 244: 1081-1085). Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64). Amino acid deletions, substitutions or additions remote from an active or binding site of a protein are generally more easily tolerated. In general, it is often possible to replace residues which form the tertiary structure, provided that residues performing a similar function are used. In other instances, the type of residue may be completely unimportant if the alteration occurs at a non-critical region of the protein.

"Codon-optimization" refers to a well-known technique used to improve heterologous protein secretion by increasing the translational efficiency of the gene of interest. The redundancy of the genetic code allows for numerous possibilities of DNA sequences that can encode for the same protein. Foreign proteins are often produced at low levels because wild-type foreign genes have not evolved for optimum expression in alternative expression hosts. The GC content and codon usage of genes are the two main sequence features recognised to influence gene expression. In order to efficiently express recombinant genes and secrete protein in higher quantities, rare codons in the native gene are replaced with codons that are more abundant in the genes of the host organism, without changing the amino acid sequence of the protein itself. Codon optimization techniques alter the codon usage pattern, which may result in increased expression levels. Codon usage tables are available, either to purchase or freely available (e.g. www.kazusa.or.jp/codon and www.kazusa.or.jp/codon).

The term "starch" refers to any material comprised of the complex polysaccharide carbohydrates of plant, comprised of amylose and amylopectin with the formula $(C6H10O5)x$, wherein X can be any number. In some embodiments, the starch-containing material may comprise xylan. Examples of "starch-containing" material include plant-based substrates (which may be fractionated plant material, for example a cereal grain such as corn, which is fractionated into components such as fiber, germ, protein and starch (endosperm)), tubers, roots, stems, whole grains, grains, corms, cobs, tall grasses, wheat, barley, rye, triticale, milo, sago, tapioca, rice peas, beans, arrow root, cassava, sweet potatoes, cereals, sugar-containing raw materials (e.g. molasses, fruit materials, sugar cane or sugar beet), potatoes, cellulose-containing materials (e.g. wood, wood residues, lignocelluloses, plant residues), wastes from agriculture (e.g. corn stover, rice straw, cereal, bran, damaged cereals, damaged potatoes, potato peel), non-cellulosic feed stocks such as sorghum, municipal waste (e.g. newspaper, waste paper), manure biomass, and agricultural residues etc.

The term "raw starch" refers to granular (unmodified) uncooked starch that has not been subjected to gelatinization. At about 25° C., starch granules start absorbing water, and as the temperature increases, the granules start to vibrate vigorously. Crystallinity decreases, and when the starch and water suspension is heated above a critical point, designated the pasting or gelatinization temperature, the granules disintegrate to make a paste.

The term "hydrolysis of starch" refers to the chemical breakdown of glycosidic bonds with the addition of water molecules.

The terms "liquefaction," "liquefy," "liquefact," and variations thereof refer to the process or product of converting starch to soluble dextrinized substrates (e.g. smaller polysaccharides). Liquefact can also be referred to as "mash".

The term "gelatinization" refers to the alteration of the starch granule from ordered, semi-crystalline granules to an amorphous state and occurs in the presence of water. This is generally done by heating the treated starch (typically treated with alpha amylase) to temperatures up to 100° C. The exact temperature of gelatinization depends on the specific starch, and can readily be determined by the skilled person.

The term "gelatinization temperature" refers to the lowest temperature at which gelatinization of a starch containing substrate begins.

The term "soluble starch" refers to starch resulting from the hydrolysis of insoluble starch (e.g. granular/raw starch).

The terms "granular starch hydrolyzing (GSH) enzyme" and "enzymes having granular starch hydrolyzing (GSH) activity" refer to enzymes that are able to hydrolyse uncooked/granular starch.

The terms "saccharifying enzyme" and "starch hydrolyzing enzyme" refer to any enzyme that is capable of converting starch to mono- or oligosaccharides (e.g. a hexose or pentose).

The phrase "consolidated bioprocessing" refers to a one-step process involving the use of a single organism that is able to achieve liquefaction, hydrolysis and fermentation of starch in a single fermentation vessel.

The phrase "simultaneous saccharification and fermentation (SSF)" refers to a process in the production of end products in which a fermenting organism, such as an ethanol producing microorganism and at least one enzyme, such as a saccharifying enzyme, are combined in the same process step in the same vessel.

"Exogenous enzymes" refers to enzymes which have not been expressed by the recombinant yeast of the present invention.

Yeasts do not form an exact taxonomic or phylogenetic grouping, but rather it is the colloquial name for single-celled members of the fungal divisions Ascomycota and Basidiomycota. The budding yeasts ("true yeasts") are classified in the order Saccharomycetales. Most reproduce asexually by budding, although a few do so by binary fission. Yeasts are unicellular, although some species with yeast forms may become multicellular through the formation of a string of connected budding cells known as pseudohyphae, or false hyphae as seen in most molds.

The invention will now be described in more detail by way of the following non-limiting examples.

Example 1: Evaluation of α-Amylases and Glucoamylases and Combinations Thereof for Raw Starch Hydrolysis Materials and Methods
Media and Cultivation Conditions All chemicals were of analytical grade and were obtained from Merck (Darmstadt, Germany), unless otherwise stated. *Escherichia coli* DH5α (Takara Bio Inc.) was used for vector propagation. The *E. coli* transformants were selected for on Luria Bertani agar (Sigma-Aldrich, Germany), containing 100 µg·ml$^{-1}$ ampicillin and cultivated at 37° C. in Terrific Broth (12 g·l$^{-1}$ tryptone, 24 g·l$^{-1}$ yeast extract, 4 ml·l$^{-1}$ glycerol, 0.1 M potassium phosphate buffer) containing 100 µg·ml$^{-1}$ ampicillin for selective pressure (Sambrook et al., 1989).

The *S. cerevisiae* Y294 strain was maintained on YPD plates (10 g·l$^{-1}$ yeast extract, 20 g·l$^{-1}$ peptone and 20 g·l$^{-1}$ glucose and 15 g·l$^{-1}$ agar) and amylolytic transformants were selected and maintained on SC$^{-URA}$ plates (containing 6.7 g·l$^{-1}$ yeast nitrogen base without amino acids (BD-Diagnostic Systems, Sparks, Md.), 20 g·l$^{-1}$ glucose, 1.5 g·l$^{-1}$ yeast synthetic drop-out medium supplements (Sigma-Aldrich, Germany), 2% corn starch (Sigma-Aldrich, Germany) and 15 g·l$^{-1}$ agar). The *S. cerevisiae* strains were aerobically cultivated on a rotary shaker (200 rpm) at 30° C., in 125 ml Erlenmeyer flasks containing 20 ml double strength SC$^{-URA}$ medium (2×SC$^{-URA}$ containing 13.4 g·l$^{-1}$ yeast nitrogen base without amino acids (BD-Diagnostic Systems, Sparks, Md.), 20 g·l$^{-1}$ glucose and 3 g·l$^{-1}$ yeast synthetic drop-out medium supplements (Sigma-Aldrich, Germany). All cultures were inoculated to a concentration of 1×10$^6$ cells·ml$^{-1}$.

Strains and Plasmids

The genotypes of the bacterial and fungal strains, as well as the plasmids used in this example, are summarised in Table 1.

TABLE 1

Strains and plasmids used in this study

| Strains and plasmids | Genotype | Reference |
|---|---|---|
| *E. coli* DH5α | supE44 ΔlacU169 (φ80lacZΔM15) hsdR17 recA1 endA1 gyrA96 thi-1 relA1 | Sambrook et al. (1989) |
| *S. cerevisiae* strains | | |
| Y294 | α leu2-3, 112 ura3-52 his3 trp1-289 | ATCC 201160 |
| Y294[BBH1] | URA3 ENO1$_P$-ENO1$_T$ | Viktor et al. (2013) |
| Y294[AmyA]$^1$ | URA3 ENO1$_P$-amyA-ENO1$_T$ | Viktor et al. (2013) |
| Y294[GlaA]$^1$ | URA3 ENO1$_P$-glaA-ENO1$_T$ | Viktor et al. (2013) |
| Y294[AmyA-GlaA]$^1$ | URA3 ENO1$_P$-amyA-ENO1$_T$; ENO1$_P$-glaA-ENO1$_T$ | Viktor et al. (2013) |
| Y294[ApuA_Nat]$^1$ | URA3 ENO1$_P$-apuA_Nat-ENO1$_T$ | This study |
| Y294[ApuA_Opt-NatSS]$^1$ | URA3 ENO1$_P$-NatSS-apuA_Opt-ENO1$_T$ | This study |
| Y294[ApuA_Nat-XYNSEC] | URA3 ENO1$_P$-XYNSEC-apuA_Nat-ENO1$_T$ | This laboratory |
| Y294[ApuA_Opt-XYNSEC] | URA3 ENO1$_P$-XYNSEC-apuA_Opt-ENO1$_T$ | This study |

TABLE 1-continued

Strains and plasmids used in this study

| Strains and plasmids | Genotype | Reference |
|---|---|---|
| Y294[ApuA_Opt-OptXYNSEC] | URA3 ENO1$_P$-OptXYNSEC-apuA_Opt-ENO1$_T$ | This study |
| Y294[AteA_Nat][1] | URA3 ENO1$_P$-ateA_Nat-ENO1$_T$ | This study |
| Y294[TemA_Nat][1] | URA3 ENO1$_P$-temA_Nat-ENO1$_T$ | This study |
| Y294[TemA_Opt] | URA3 ENO1$_P$-temA_Opt-ENO1$_T$ | This study |
| Y294[TemA_Opt-XYNSEC] | URA3 ENO1$_P$-XYNSEC-temA_Opt-ENO1$_T$ | This study |
| Y294[TemA_Nat- XYNSEC] | URA3 ENO1$_P$-XYNSEC-temA_Nat-ENO1$_T$ | This study |
| Y294[TemA_Opt-NatSS][1] | URA3 ENO1$_P$-NatSS-temA_Opt-ENO1$_T$ | This study |
| Y294[AteG_Nat][1] | URA3 ENO1$_P$-ateG_Nat-ENO1$_T$ | This study |
| Y294[AteG_Nat-XYNSEC] | URA3 ENO1$_P$-XYNSEC-ateG_Nat-ENO1$_T$ | This study |
| Y294[AteG_Opt-XYNSEC] | URA3 ENO1$_P$-XYNSEC-ateG_Opt-ENO1$_T$ | This study |
| Y294[AteG_Opt-NatSS] | URA3 ENO1$_P$-NatSS-ateG_opt-ENO1$_T$ | This study |
| Y294[TemG_Nat][1] | URA3 ENO1$_P$-temG_Nat-ENO1$_T$ | This study |
| Y294[TemG_Opt] | URA3 ENO1$_P$-temG_Opt-ENO1$_T$ | This study |
| Y294[TemG_Opt-XYNSEC][1] | URA3 ENO1$_P$-XYNSEC-temG_Opt-ENO1$_T$ | This study |
| Y294[TemG_Nat-XYNSEC][1] | URA3 ENO1$_P$-XYNSEC-temG_Nat-ENO1$_T$ | This study |
| Y294[TemG_Opt-NatSS][1] | URA3 ENO1$_P$-NatSS-temG_Opt-ENO1$_T$ | This study |
| Y294[TemG_Opt-AmyA] | URA3 ENO1$_P$-temG_Opt-ENO1$_T$; ENO1$_P$-amyA-ENO1$_T$ | This study |
| Y294[TemG_Opt-TemA_Nat] | URA3 ENO1$_P$-temG_Opt-ENO1$_T$; ENO1$_P$-temA_Nat-ENO1$_T$ | This study |
| Y294[TemG_Opt-TemA_Opt] | URA3 ENO1$_P$-temG_Opt-ENO1$_T$; ENO1$_P$-temA_Opt-ENO1$_T$ | This study |
| Y294[TemG_Opt-AteA_Nat] | URA3 ENO1$_P$-temG_Opt-ENO1$_T$; ENO1$_P$-ateA_Nat-ENO1$_T$ | This study |
| Y294[TemG_Opt-ApuA_Nat] | URA3 ENO1$_P$-temG_Opt-ENO1$_T$; ENO1$_P$-apuA_Nat-ENO1$_T$ | This study |
| Y294[GlaA_Nat-TemA_Nat] | URA3 ENO1$_P$-glaA-ENO1$_T$; ENO1$_P$-temA_Nat-ENO1$_T$ | This study |
| Y294[TemG_Nat-AmyA] | URA3 ENO1$_P$-temG_Nat-ENO1$_T$; ENO1$_P$-amyA-ENO1$_T$ | This study |
| Y294[TemG_Nat-AteA_Nat] | URA3 ENO1$_P$-temG_Nat-ENO1$_T$; ENO1$_P$-ateA_Nat-ENO1$_T$ | This study |
| Y294[TemG_Nat-ApuA_Nat] | URA3 ENO1$_P$-temG_Nat-ENO1$_T$; ENO1$_P$-apuA_Nat-ENO1$_T$ | This study |
| Y294[AteG_Nat-XYNSEC-AmyA] | URA3 ENO1$_P$-ateG_Nat-ENO1$_T$; ENO1$_P$-amyA-ENO1$_T$ | This study |
| Plasmids | | |
| yBBH1 | bla URA3 ENO1$_P$-ENO1$_T$ | Njokweni et al. (2012) |
| yBBH4 | bla URA3 ENO1$_P$-XYNSEC-ENO1$_T$ | Njokweni et al. (2012) |
| yBBH1-AmyA | bla URA3 ENO1$_P$-amyA-ENO1$_T$ | Viktor et al. (2013) |
| yBBH1-GlaA | bla URA3 ENO1$_P$-glaA-ENO1$_T$ | Viktor et al. (2013) |
| yBBH1-AteA_Nat | bla URA3 ENO1$_P$-ateA_Nat-ENO1$_T$ | This study |
| yBBH1-ApuA_Nat | bla URA3 ENO1$_P$-apuA_Nat-ENO1$_T$ | This study |
| yBBH1-TemA_Nat | bla URA3 ENO1$_P$-temA_Nat-ENO1$_T$ | This study |
| yBBH1-TemA_Opt | bla URA3 ENO1$_P$-temA_Opt-ENO1$_T$ | This study |
| yBBH1-AteG_Nat-XYNSEC | bla URA3 ENO1$_P$-ateG_Nat-ENO1$_T$ | This study |
| yBBH1-TemG_Nat | bla URA3 ENO1$_P$-temG_Nat-ENO1$_T$ | This study |
| yBBH1-TemG_Opt | bla URA3 ENO1$_P$-temG_Opt-ENO1$_T$ | This study |
| yBBH1-TemG_Nat-ApuA_Nat | bla URA3 ENO1$_P$-temG_Nat-ENO1$_T$; ENO1$_P$-apuA_Nat-ENO1$_T$ | This study |
| yBBH1-TemG_Nat-AmyA | bla URA3 ENO1$_P$-temG_Nat-ENO1$_T$; ENO1$_P$-amyA-ENO1$_T$ | This study |
| yBBH1-TemG_Nat-AteA_Nat | bla URA3 ENO1$_P$-temG_Nat-ENO1$_T$; ENO1$_P$-ateA_Nat-ENO1$_T$ | This study |
| yBBH1-TemG_Opt-ApuA_Nat | bla URA3 ENO1$_P$-temG_Opt-ENO1$_T$; ENO1$_P$-apuA_Nat-ENO1$_T$ | This study |
| yBBH1-TemG_Opt-AmyA | bla URA3 ENO1$_P$-temG_Opt-ENO1$_T$; ENO1$_P$-amyA-ENO1$_T$ | This study |
| yBBH1-TemG_Opt-AteA_Nat | bla URA3 ENO1$_P$-temG_Opt-ENO1$_T$; ENO1$_P$-ateA-ENO1$_T$ | This study |
| yBBH1-TemG_Opt-TemA_Nat | bla URA3 ENO1$_P$-temG_Opt-ENO1$_T$; ENO1$_P$-temA_Nat-ENO1$_T$ | This study |
| yBBH1-TemG_Opt-TemA_Opt | bla URA3 ENO1$_P$-temG_Opt-ENO1$_T$; ENO1$_P$-temA_Opt-ENO1$_T$ | This study |

TABLE 1-continued

Strains and plasmids used in this study

| Strains and plasmids | Genotype | Reference |
|---|---|---|
| yBBH1-GlaA-TemA_Nat | bla URA3 ENO1$_P$-glaA-ENO1$_T$; ENO1$_P$-temA_Nat-ENO1$_T$ | This study |
| yBBH4-AteG_Nat-XYNSEC-AmyA | bla URA3 ENO1$_P$-XYNSEC-ateG_Nat-ENO1$_T$; ENO1$_P$-amyA-ENO1$_T$ | This study |

[1]native secretion signal
_Nat: native coding sequence;
_Opt: codon-optimized coding sequences (GenScript);
-NatSS: native secretion signal;
-XYNSEC: native secretion signal from *Trichoderma reesei* Xyn2 gene,
-OptXYNSEC: codon optimized-XYNSEC secretion signal

DNA Manipulations

Standard protocols were followed for all DNA manipulations and *E. coli* transformations (Sambrook et al., 1989). All genes were synthesised by GenScript (Piscataway, N.J., USA), based on the nucleotide accession numbers listed below. The internal EcoRI, XhoI, BamHI and BglII restriction sites were avoided, but the amino acid sequence remained unaffected. The polymerase chain reaction (PCR) was performed using a Perkin Elmer Gene Amp® PCR System 2400 and TaKaRa Ex Taq™ (Takara Bio Inc, Japan) as per the manufacturer's recommendations. The amylase genes were amplified using primers (Inqaba Biotec, South Africa) (Table 2) designed for yeast mediated ligation (YML) and visualised on a 0.8% agarose gel. DNA was eluted from agarose gels with the Zymoclean™ Gel Recovery Kit (Zymo Research, USA).

The amylase genes were subcloned individually onto the yBBH1 or yBBH4 plasmid (FIGS. 1a, b and c) in order to construct the expression vectors listed in Table 1. The yBBH4 vector (FIG. 1c) contained the sequence encoding for the XYNSEC secretion signal of the *Trichoderma reesei* xyn2 (Den Haan et al., 2007) for directing the secretion of the amylases. The ENO1$_P$-α-amylase-ENO1$_T$ cassettes were amplified from the yBBH1-α-amylase vectors using YML cassette primers: ENOCASS-L: gtgcggtatttcacaccgcatagga-gatcgatcccaattaatgtgagttacctcactc (SEQ ID NO: 35) and ENOCASS-R: cgggcctcttcgctattacgccagagcttagatct (SEQ ID NO: 36) and cloned on the BglII site of yBBH1-glucoamylase or yBBH4-glucoamylase vectors (FIGS. 1c and d). Sequence verification of the final vector constructs was performed by the dideoxy chain termination method, with an ABI PRISM™ 3100 Genetic Analyser (CAF, Stellenbosch University).

TABLE 2

PCR oligo-primers used in this study with the relevant restriction sites underlined
(EcoRI = gaattc; NruI = tcgcga; XhoI = ctcgag)

| Gene name (host organism) | | Sequence (5'-3') | SEQ ID NO: | Signal peptide[1] |
|---|---|---|---|---|
| apuA (*A. pullulans*) | ApuA_Nat-L: | tgcttatcaacacacaaacactaaatcaaa<u>gaattc</u>atggcagccaactacgtttctcgattgttg | 8 | 22 |
| | ApuA_N-R: | gactagaaggcttaatcaaaagct<u>ctcgag</u>tcaccccctgccaagtattgctgaccgatgc | 9 | |
| | ApuA_Opt-NatSS-L: | tctctacttgaccgggttggtgcagtgtttgactccagctcaatggagaagtcaatctat | 10 | |
| | ApuA_Opt-R: | ggactagaaggcttaatcaaaagct<u>ctcgag</u>ctaaccttgccatgtattggagactgagg | 11 | |
| | ApuA_optXynSec-L: | gaacccgtggctgtggagaagcgc<u>tcgcga</u>ttgactccagctcaatggagaagtc | 12 | |
| | ApuA_Opt-R: | ggactagaaggcttaatcaaaagct<u>ctcgag</u>ctaaccttgccatgtattggagactgagg | 13 | |
| ateA (*A. terreus*) | AteA_Nat-L: | tgcttatcaacacacaaacactaaatcaaa<u>gaattc</u>atgaagtggacctcctcgctcctcctctta | 14 | 20 |
| | AteA_Nat-R: | gactagaaggcttaatcaaaagct<u>ctcgag</u>tcacctccaagtatcagcaactgtcaccgt | 15 | |
| temA (*T. emersonii*) | TemA_Nat-L: | tgcttatcaacacacaaacactaaatcaaa<u>gaattc</u>atgacgcctttcgtcctcacggcc | 16 | 19 |
| | TemA_Nat-R | ggactagaaggcttaatcaaaagct<u>ctcgag</u>ctatctccatgtgtcgacaatcgtctccg | 17 | |
| | TemA_Opt-NatOptSS-L: | tgcttatcaacacacaaacactaaatcaaa<u>gaattc</u>atgacccdtttgttttgacagcc | 18 | |
| | TemA_Opt-R: | ggactagaaggcttaatcaaaagct<u>ctcgag</u>ctatctccaagtgtcaacaatagtttcag | 19 | |
| | TemA_Nat-xynsecSS-L: | gaacccgtggctgtggagaagcgc<u>tcgcga</u>ttgaccccggccgaatggcgcaaacaat | 20 | |
| | TemA_Opt-xynsecSS-L | gaacccgtggctgtggagaagcgc<u>tcgcga</u>ttgacaccagccgaatggagaaagcaatc | 21 | |
| | TemA_Opt-NatSS-L: | tcttgctggggaatgccgtgttggccttgacaccagccgaatggagaaagc | 22 | |
| ateG (*A. terreus*) | AteG_Nat-L: | tgcttatcaacacacaaacactaaatcaaa<u>gaattc</u>atgacgcgcattctcaccctcgcccttcat | 23 | 20 |
| | AteG_Nat-R: | ggactagaaggcttaatcaaaagct<u>ctcgag</u>ctagcgccaagtggtgttcaccaccgcggt | 24 | |
| | AteG_Opt-NatSS-L: | gggctggctcttgtccaaagtgttgttggggcaccacaattggctcctagagcaactaca | 25 | |
| | AteG_Opt-R: | tggactagaaggcttaatcaaaagct<u>ctcgag</u>ctatctccaggttgtgttgacaacggcg | 26 | |
| | AteG_Nat-xynSS-L: | gaacccgtggctgtggagaagcgc<u>tcgcga</u>gctcccccaattggccccagagcgacaacc | 27 | |

TABLE 2 -continued

PCR oligo-primers used in this study with the relevant restriction sites underlined
(EcoRI = gaattc; NruI = tcgcga; XhoI = ctcgag)

| Gene name (host organism) | Sequence (5'-3') | SEQ ID NO: | Signal peptide[1] |
|---|---|---|---|
| temG (T. emersonii) | TemG_Nat-L: tgcttatcaacacacaaacactaaatcaaagaattcatggcgtccctcgttgctggcgctctctgc | 28 | 20 |
|  | TemG_Nat-R: ggactagaaggcttaatcaaaagctctcgagtcactgccaactatcgtcaagaatggcggt | 29 |  |
|  | TemG_Nat-xynsecSS-L: gaaccegtggctgtggagaagcgctcgcgacgagcgcccgttgcagcgcgagccaccggt | 30 |  |
|  | TemG_Opt-xynsecSS-L: gaaccegtggctgtggagaagcgctcgcgaagagccccagtcgcagccagagcaacaggt | 31 |  |
|  | TemG_Opt-R: gactagaaggcttaatcaaaagctctcgagtcattgccaagagtcgtccaagattgcggt | 32 |  |
|  | TemG_Opt-NatOptSS-L: ttatcaacacacaaacactaaatcaaagaattcatggcctccttagtcgcaggtgcctta | 33 |  |
|  | TemG_Opt-NatSS-L: atcctgggcctgacgcctgctgcatttgcaagagcccagtcgcagccagagcaacaggt | 34 |  |

[1]The length (amino acids) of putative signal peptides was analysed using SignalP 4.1 (www.cbs.dtu.dk/services/SignalP).

Amylase Genes and GenBank Accession Numbers

The following amylases were cloned and expressed in *S. cerevisiae* Y294. The native glucoamylases from *A. pullulans* (Accession no. HM246718), *A. terreus* (Accession no. XP_001213553), *H. grisea* (Accession no. M89475), *T. emersonii* (Accession no. AJ304803) and *T. lanuginosus* (Accession no. EF545003), as well as the native α-amylases from *A. pullulans* (Accession no. AEH03024), *A. terreus* (Accession no. XM_001209405), *N. fischeri* (Accession no. XP_001265628), *R. pusillus* (Accession no. AGJ52081) and *T. emersonii* (Accession no. XM_013469492). Coding sequences for the glucoamylases from *C. thermophilum* (Accession no. ABD96025), *T. stipitatus* (Accession no. XP_002484948), *A. terreus* and *T. emersonii*, as well for α-amylases from *A. pullulans* and *T. emersonii* were codon-optimized for expression in *S. cerevisiae* (GenScript, Piscataway, N.J., USA). *T. emersonii* has recently been classified as *Rasamsonia emersonii* (Houbraken et al., 2012).

Yeast Transformations

The *S. cerevisiae* Y294 strain was grown overnight in 5 ml YPD broth and prepared according to Cho et al. (1999). After electroporation, 1 ml of YPDS was immediately added to the cuvette. Cultures were incubated at 30° C. for 1 hour prior to plating out onto $SC^{-URA}$ plates containing 2% starch. Plates were incubated at 30° C. for 2-3 days and then transferred to 4° C. for 24 hours to allow the starch to precipitate.

Activity Assays

For quantitative assays, yeast transformants were cultured in 20 ml $2 \times SC^{-URA}$ medium in 125 ml Erlenmeyer flasks with agitation at 200 rpm and sampling at 24 hour intervals. The supernatant was harvested and extracellular enzymatic activity levels were assessed colourimetrically (xMark™ Microplate Spectrophotometer, Bio-Rad, San Francisco, USA) using the reducing sugar assay with glucose as standard (Miller 1959). The α-amylase activities were determined after a 5 minute incubation with 0.2% soluble corn starch in 0.05 M citrate-acid buffer (pH 5) at 37° C.

Glucoamylase activity was determined by incubating 50 µl supernatant with 450 µl of 0.2% soluble corn starch in 0.05 M citrate-acid buffer (pH 5) at 37° C. for 15 minutes. The glucose concentration was determined using the D-Glucose Assay Kit (Megazyme, Ireland) with absorbance measured at 510 nm (xMark™ Microplate Spectrophotometer, Bio-Rad, San Francisco, USA). Enzymatic activities were expressed as nano-katals per ml ($nkat \cdot ml^{-1}$), with nkat defined as the enzyme activity needed to produce 1 nmol of glucose per second under the described assay conditions.

Protein Analysis

Recombinant *S. cerevisiae* Y294 strains were cultivated in 125 ml Erlenmeyer flasks containing 20 ml $2 \times SC^{-URA}$ medium for 3 days. Twenty microliters of supernatant was added to protein loading buffer and the samples boiled for 3 minutes to denature the proteins. The recombinant proteins were separated on an 8% SDS-polyacrylamide gel using a 5% stacking gel and Tris-glycine buffer (Sambrook et al., 1989). Electrophoresis was carried out at 100 V for ±90 minutes at ambient temperature and protein species were visualised using the silver staining method (O'Connell and Stults, 1997). The broad-range Page Ruler Prestained SM0671 Protein Ladder (Fermentas, China) was used as a molecular mass marker.

Raw Starch Fermentations

Precultures were cultured in 60 ml $2 \times SC^{-URA}$ media in 250 ml Erlenmeyer flasks and incubated at 30° C. with agitation of 200 rpm. Fermentations were performed with $2 \times SC^{-URA}$ media containing 200 $g \cdot l^{-1}$ raw corn starch and 5 $g \cdot l^{-1}$ glucose and inoculated with a 10% ($v \cdot v^{-1}$) inoculum. Ampicillin (100 $\mu g \cdot ml^{-1}$) and streptomycin (50 $\mu g \cdot ml^{-1}$) were added to inhibit bacterial contamination. Agitation and incubation were performed on a magnetic multi-stirrer at 30° C., with daily sampling through a syringe needle pierced through the rubber stopper.

For bioreactor experiments with laboratory strains, precultures were cultivated in 120 ml $2 \times SC^{-URA}$ media in 500 ml Erlenmeyer flasks at 30° C. with agitation at 200 rpm. Bioreactor fermentations were performed in a 2 liter MultiGen Bioreactor (New Brunswick Scientific Corporation, Edison, N.J.) containing $2 \times SC^{-URA}$ media supplemented with 200 $g \cdot l^{-1}$ raw corn starch and 5 $g \cdot l^{-1}$ glucose as carbohydrate source. A 10% ($v \cdot v^{-1}$) inoculum was used in a total working volume of 1 liter. Fermentations were carried out at 26° C. and 30° C. with stirring at 300 rpm and daily sampling through a designated sampling port. All fermentation experiments were performed in triplicate.

High Performance Liquid Chromatography (HPLC) Analysis

Ethanol, glucose, maltose, glycerol and acetic acid concentrations were quantified with HPLC using a Surveyor Plus liquid chromatograph (Thermo Scientific) consisting of a liquid chromatography pump, autosampler and refractive index (RI) detector. The compounds were separated on a Rezex RHM Monosaccharide 7.8×300 mm column (00H0132-K0, Phenomenex) at 80° C. with 5 mM $H_2SO_4$ as mobile phase at a flow rate of 0.6 $ml \cdot min^{-1}$.

Analytical Methods and Calculations

The theoretical $CO_2$ concentrations were calculated according to Favaro et al. (2015). The glucose equivalent is defined as the mass of glucose resulting from the complete hydrolysis of starch, i.e. 1.11 grams of glucose per gram of starch. The available carbon (mol C in 100% hydrolysed substrate) was calculated based on the available glucose equivalents and the carbon conversion is defined as the percentage starch converted to fermentable products on a mol carbon basis. This carbon conversion was calculated from ethanol, glucose, maltose, glycerol, acetic acid and $CO_2$ concentrations. The ethanol yield (% of the theoretical yield) was calculated as the amount of ethanol produced per gram of consumed glucose. The ethanol rate of productivity was calculated based on ethanol titres produced per hour ($g·l^{-1}·h^{-1}$).

Statistical Analysis

Data was analysed using the Student's t-test.

Results

Functional Expression of Recombinant Amylases

The *S. cerevisiae* Y294 strain was used as host for the heterologous gene expression of recombinant amylases. Recombinant strains were constructed to express either an α-amylase or glucoamylase encoding gene (Table 1) and evaluated for their ability to hydrolyse corn starch using the *S. cerevisiae* Y294[AmyA] and Y294[GlaA] strains, respectively, as benchmarks strains (Viktor et al., 2013). All the recombinant strains evaluated in this study were able to hydrolyse soluble starch (demonstrated by zones of hydrolysis during plate assays—data not shown).

However, several amylase candidates showed significantly lower levels of extracellular activity (nkat·ml$^{-1}$), when compared to the benchmark *S. cerevisiae* Y294 strains expressing the amyA and glaA genes (data no shown). Thus, the following genes were omitted from further evaluation: native glucoamylases from *A. pullulans*, *H. grisea* and *T. lanuginosus*, as well as the codon-optimized α-amylases from *N. fischeri*, *R. pusillus* and codon-optimized glucoamylases from *C. thermophilum* and *T. stipitatus*. The different gene variants for the ateA, apuA, temA, ateG and temG genes contained different DNA sequences, but encoded for the same amino acid sequence (for the mature protein).

α-Amylases

The ateA_Nat gene was efficiently expressed by the *S. cerevisiae* Y294[AteA_Nat] strain, but the extracellular levels of activity were consistently lower than that of the *S. cerevisiae* Y294[AmyA] benchmark strain (FIG. 2a). Replacing the native secretion signal with the native XYNSEC (*S. cerevisiae* Y294[AteA_Nat-XYNSEC]) did not result in significant differences in either extracellular activity or the amount of AteA secreted (FIGS. 2a and 2d). The extracellular protein levels of AmyA and AteA were similar (FIG. 2d).

The *S. cerevisiae* Y294[ApuA_Nat] and Y294[TemA_Nat] strains displayed more extracellular α-amylase activity on soluble starch (FIGS. 2b and 2c) than the *S. cerevisiae* Y294[AmyA] benchmark strain. Codon optimization of the apuA_Nat and temA_Nat genes resulted in less extracellular activity due to a decrease in enzyme concentration (FIGS. 2e and 2f). Changing the secretion signal also resulted in a decrease in extracellular enzyme concentration, with a negative impact on extracellular activity (FIGS. 2c and 2d).

SDS-PAGE analysis of the supernatant indicated that most of these α-amylases are glycosylated. ApuA and AteA protein species (calculated molecular weights of 65.25 kDa and 64.14 kDa, respectfully) (FIGS. 2b and 2d) are the least glycosylated with a putative recombinant size of around 70 kDa, while TemA (calculated molecular weight of 66.29 kDa) had a higher degree of glycosylation (FIG. 2f) and a putative size of around 90 kDa. The large heterogeneous smear between 110 and 150 kDa for the AmyA protein is consistent with that of a previous report (Viktor et al., 2013).

Glucoamylases

The replacement of the ateG_Nat secretion signal with the XYNSEC sequence improved extracellular glucoamylase activity, albeit less than the activity displayed by the *S. cerevisiae* Y294[GlaA] strain (FIG. 3a). The *S. cerevisiae* Y294[AteG_Opt-XYNSEC] and Y294[AteG_Nat-XYNSEC] strains produced similar levels of activity, which exceeded the activity by the strains containing the native ateG secretion signal. The *S. cerevisiae* Y294[AteG_Opt-NatSS] strain secreted no visible protein (FIG. 3c) confirming that the native ateG secretion signal negatively affected protein secretion. Codon optimization did not have a visible effect on the extracellular amount of AteG protein produced, despite the increase in extracellular activity (FIGS. 3a and 3c).

A significant increase in extracellular glucoamylase activity was observed when the temG gene sequence was codon-optimized (FIG. 3b). At 72 hours, extracellular activity for the *S. cerevisiae* Y294[TemG_Opt] strain was >3-fold higher than the *S. cerevisiae* Y294[TemG_Nat] strain and >10-fold higher than the Y294[GlaA] benchmark strain. Changing secretion signals for the expression of the temG indicated that the optimized temG secretion signal contributed to enhanced protein secretion and extracellular activity (FIGS. 3b and 3d), whereas replacement with the XYNSEC secretion signal had a negative impact.

SDS-PAGE analysis of the supernatant indicated that these glucoamylases are glycosylated. The AteG protein species (calculated molecular weight of 65.73 kDa) (FIG. 3c) had a putative size of around 95 kDa, while the TemG protein (calculated molecular weight of 63.57 kDa) is less glycosylated with a putative size of around 85 kDa (FIG. 3d). Moreover, the intensity of the recombinant protein species visualised using SDS-PAGE showed correlation with the extracellular enzyme activity levels for all amylases.

Raw Corn Starch Fermentations

The amylase encoding genes that resulted in the highest levels of extracellular activity when expressed in *S. cerevisiae* Y294 (apuA_Nat, ateA_Nat, temA_Nat, temA_Opt, ateG_Nat-XYNSEC, temG_Nat and temG_Opt), together with the reference (amyA and glaA) genes, were then used to construct amylolytic strains that produced an α-amylase and glucoamylase combination (Table 1). The recombinant yeast strains were evaluated for their ability to hydrolyse raw starch and ferment glucose at a high substrate loading under oxygen-limited conditions.

At 192 hours, the *S. cerevisiae* Y294[TemG_Opt-TemA_Nat] strain produced the highest ethanol concentration (62.2 g·l$^{-1}$), which is 59.7% of the theoretical value (FIG. 4a). After 120 hours, this strain produced 51.7 g·l$^{-1}$ ethanol, which represents a 1.6-fold improvement on the *S. cerevisiae* Y294[AmyA-GlaA] benchmark strain (p=0.0013). Ethanol levels of 38.6 g·l$^{-1}$ and 39.4 g·l$^{-1}$ produced by the *S. cerevisiae* Y294[TemG_Opt-ApuA_Nat] and Y294[TemG_Opt-AteA_Nat] strains, respectively, were also higher than the benchmark strain (at 120 hours). The *S. cerevisiae* Y294[TemG_Opt-TemA_Nat] strain accumulated 46.3 g·l$^{-1}$ residual glucose after 192 hours of fermentation (FIG. 4c).

The *S. cerevisiae* Y294 strains expressing the TemG_Nat-AmyA, TemG_Nat-AteA_Nat, TemG_Nat-ApuA_Nat and AteG_Nat-XYNSEC-AmyA enzyme combinations produced less ethanol compared to the *S. cerevisiae* Y294 [AmyA-GlaA] benchmark strain (FIGS. 4a and 4b), with little to no residual glucose detected (FIG. 4d). Overall, results depicted in FIG. 4c indicated that the S. cerevisiae Y294[TemG_Opt-TemA_Nat] strain was superior to the other strains and this enzyme combination was effective in hydrolyzing raw corn starch. At 192 hours, carbon conversion displayed by the S. cerevisiae Y294[TemG_Opt-TemA_Nat] strain was 57% higher than that displayed by the S. cerevisiae Y294[AmyA-GlaA] benchmark strain, whereas the Y294[TemG_Opt-AteA_Nat] strain produced comparable results to that of the benchmark strain (Table 3).

Amylase genes were heterologously expressed in order to choose the enzymes with the highest extracellular enzyme activity and to investigate the effect of synonymous codon usage on gene expression (Table 1). In this study, several amylase candidates showed significantly low levels of extracellular activity, compared to the benchmark strain (data not shown). Thus, the following genes were omitted from further studies: native glucoamylases from A. pullulans, H. grisea and T. lanuginosus, as well as the optimized α-amy-

TABLE 3

Products formed by S. cerevisiae Y294 strains after 192 hours of fermentation at 30° C. in 2 × SC$^{-URA}$ broth with glucose (5 g · l$^{-1}$) and raw corn starch (200 g · l$^{-1}$)

| S. cerevisiae Y294 Strains | [TemG_Opt-AmyA] | [TemG_Opt-TemA_Nat] | [TemG_Opt-TemA_Opt] | [TemG_Opt-AteA_Nat] | [TemG_Opt-ApuA_Nat] | [GlaA-AmyA] | [GlaA-TemA_Nat] |
|---|---|---|---|---|---|---|---|
| Substrate (g · l$^{-1}$) | | | | | | | |
| Raw starch (dry weight) | 185 | 185 | 185 | 185 | 185 | 185 | 185 |
| Glucose equivalent Products (g · l$^{-1}$) | 208.5 | 208.5 | 208.5 | 208.5 | 208.5 | 208.5 | 208.5 |
| Glucose | 2.72 | 46.30 | 1.67 | 1.94 | 1.21 | 5.30 | 4.12 |
| Glycerol | 4.76 | 6.64 | 2.40 | 3.43 | 2.45 | 2.46 | 2.26 |
| Maltose | 1.09 | 1.03 | 1.07 | 1.14 | 0.95 | 1.02 | 1.17 |
| Acetic acid | 1.91 | 1.66 | 0.60 | 0.85 | 0.61 | 0.61 | 0.56 |
| Ethanol | 47.40 | 62.20 | 48.71 | 53.46 | 43.12 | 52.78 | 46.56 |
| CO$_2$[1] | 45.33 | 59.50 | 46.59 | 51.13 | 41.25 | 50.48 | 44.53 |
| Total | 103.21 | 177.33 | 101.04 | 111.95 | 89.60 | 112.65 | 99.20 |
| Carbon conversion (%) | 49.50 | 85.05 | 48.46 | 53.69 | 42.97 | 54.03 | 47.58 |
| Ethanol[2] (% of theoretical yield) | 45.46 | 59.67 | 46.72 | 51.28 | 41.36 | 50.63 | 44.66 |
| Ethanol rate of productivity[3] | 0.247 | 0.324 | 0.254 | 0.278 | 0.225 | 0.275 | 0.242 |

[1]CO$_2$ concentrations were deduced from the ethanol produced
[2]Ethanol yield (% of the theoretical yield) was calculated as the amount of ethanol produced per gram of consumed sugar (at a specific time point)
[3]Ethanol rate of productivity was calculated based ethanol titres produced per hour (g · l$^{-1}$ · h$^{-1}$)

Figure 4:
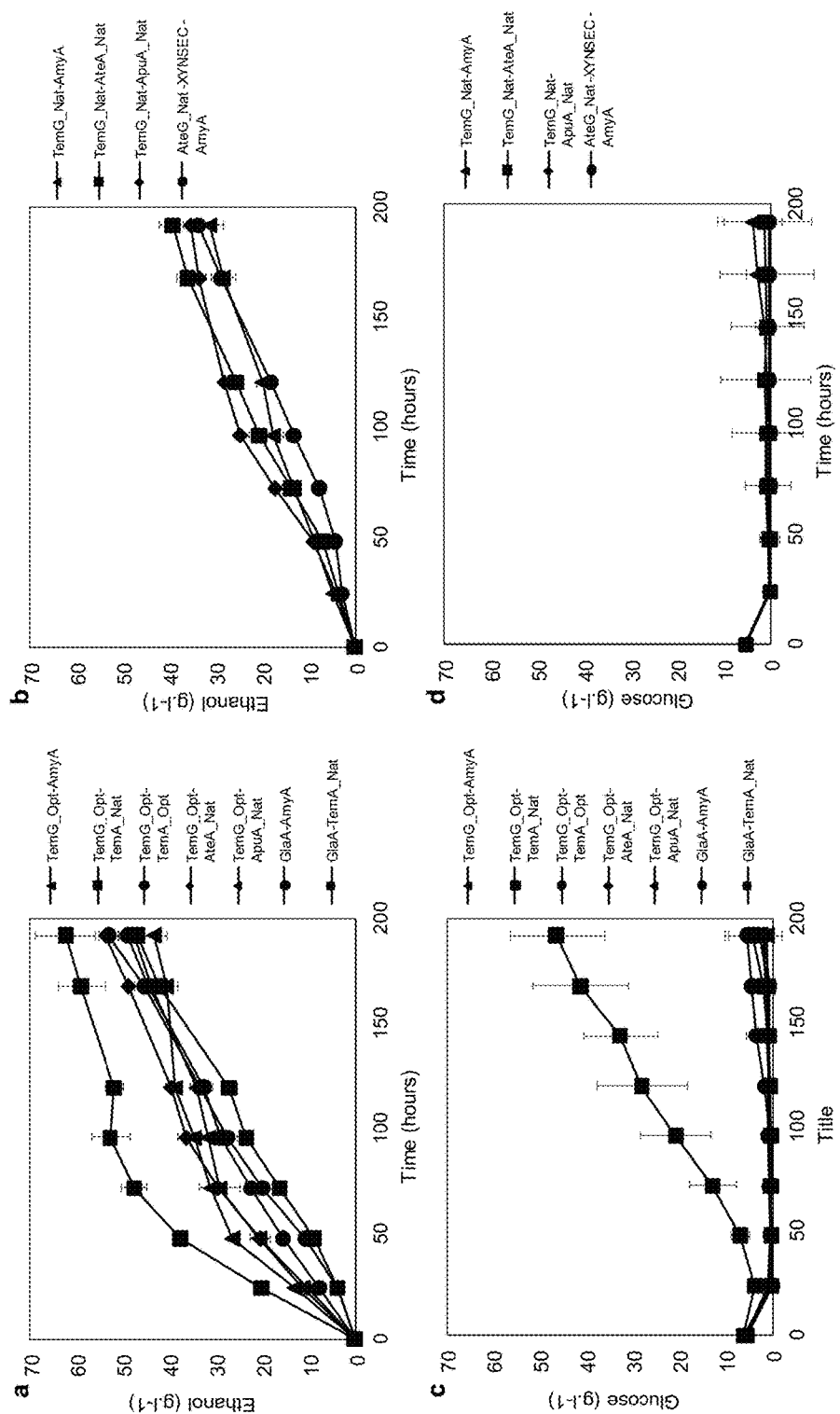
FIG. 4 The amylolytic *S. cerevisiae* Y294 strains were evaluated on 200 g·l$^{-1}$ raw corn starch and 5 g·l$^{-1}$ glucose as sole carbohydrate source. The (a and b) ethanol and (c and d) glucose production was monitored overtime. Results from the best performing strains (left panel) and suboptimal strains (right panel) came from the same fermentation. Values represent the mean of three repeats and error bars represent the standard deviation.
Figure 5:
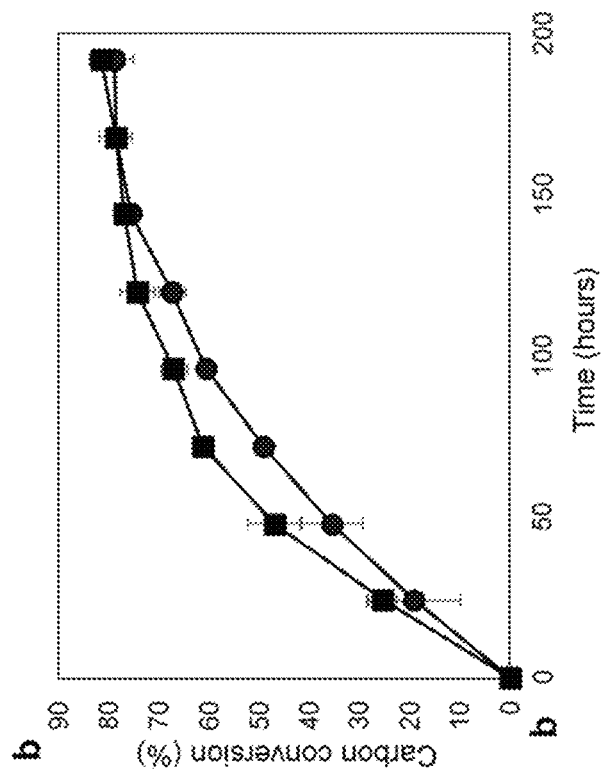
FIG. 5 The performance of *S. cerevisiae* Y294 [TemG_Opt-TemA_Nat] in a 2 liter bioreactor. (a) Ethanol concentrations at 26° C. (-●-) and 30° C. (-■-) and residual glucose concentrations at 26° C. (-○-) and at 30° C. (-□-) and (b) carbon conversion (%) at 26° C. (-●-) and 30° C. (-■-), respectively, with 2×SC$^{-URA}$ broth supplemented with 5 g·l$^{-1}$ glucose and 200 g·l$^{-1}$ raw corn starch. Values represent the mean of triplicate repeats and error bars represent the standard deviation.
Figure 5:
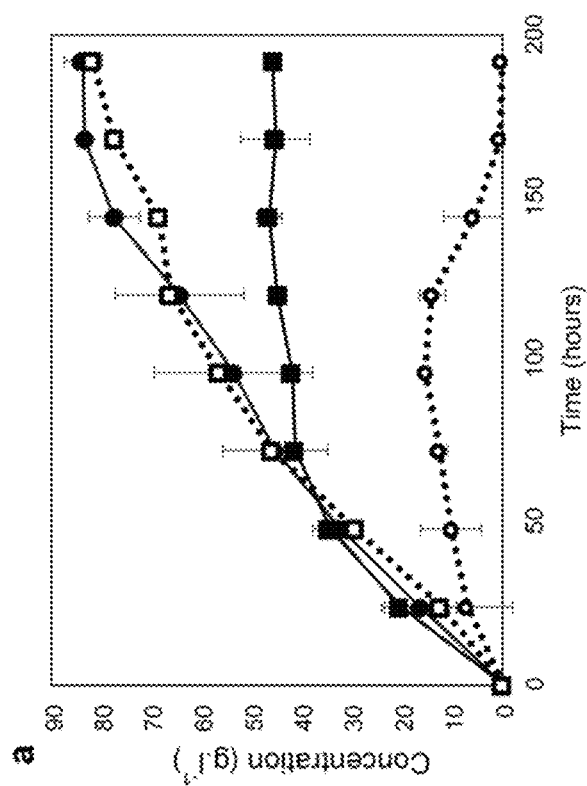

The S. cerevisiae Y294[TemG_Opt-TemA_Nat] strain was evaluated in a 2 liter bioreactor (1 liter working volume) under two fermentation temperatures (26° C. and 30° C.) (FIG. 5). After 192 hours, the final ethanol concentration (83.8 g·l$^{-1}$) was significantly higher at a fermentation temperature of 26° C. (FIG. 4a), however the carbon conversion percentages were similar (79-81%). After 192 hours, a decrease in fermentation temperature resulted in 1.8-fold improvement in the ethanol concentration and no residual glucose was detected at a fermentation temperature of 26° C. (FIG. 4a). The carbon conversion displayed by the S. cerevisiae Y294[TemG_Opt-TemA_Nat] strain (at 30° C.) was similar for both fermentation types (100 ml bottle fermentations and bioreactor), 85% and 81% respectively, after 192 hours (FIGS. 4a and 5b).

Discussion

A selection of amylases from various fungi have been investigated independently by several research groups, with raw starch hydrolyzing enzymes being favoured for starch conversion to ethanol (Robertson et al., 2006; Viktor et al., 2013; Favaro et al., 2015; Celińska et al., 2015). Approximately 10% of all amylases contain a starch binding domain (SBD) (Sun et al., 2010), which is classically associated with the adsorption of these enzymes to raw starch granules, thereby enhancing the amylolytic rate and the subsequent hydrolysis (Santiago et al., 2005; Mitsuiki et al., 2005). Thus, for this study, the presence of a SBD was a prerequisite when selecting amylases for expression in S. cerevisiae.

lases from N. fischeri, R. pusillus and codon-optimized glucoamylases from C. thermophilum and T. stipitatus.

Figure 2:
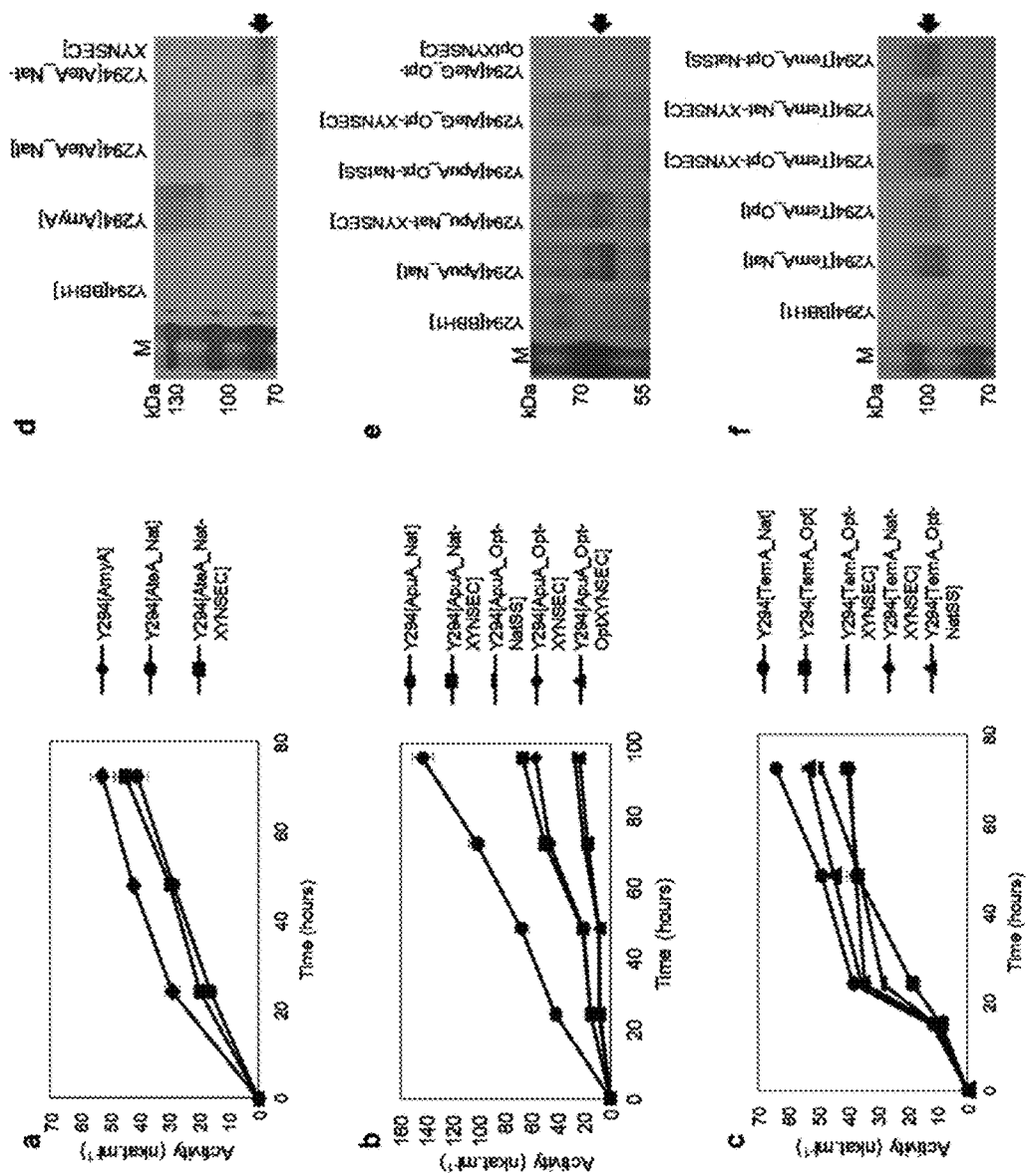
FIG. 2 Extracellular α-amylase activity displayed by the *S. cerevisiae* Y294 strains expressing the (a) ateA, amyA, (b) apuA and (c) temA gene derivatives, respectively. The *S. cerevisiae* Y294[AmyA] strain was used for benchmark α-amylase production. Values represent the mean of three repeats and error bars represent the standard deviation. Supernatant from the *S. cerevisiae* Y294 strains (after 72 hours) was subjected to SDS-PAGE followed by silver staining. The arrows indicate the presence of the recombinant (d) AmyA, AteA, (e) ApuA and (f) TemA protein species, respectively. The *S. cerevisiae* Y294[BBH1] strain was used as the reference strain and the protein size marker (M) is depicted on the left hand side.

High levels of protein expression can be correlated to the codon adaptation index (CAI) (Carbone et al., 2003). A CAI value of 1.0 is considered to be ideal, while GenScript recommends that a CAI of >0.8 is rated as good for expression in the desired expression organism. Analysis of the genes' CAI values using GenScript's OptimumGene™ (www.genscript.com/cgi-bin/tools/rare_codon_analysis) indicated that all CAI values increased when the genes were optimized. GenScript's algorithm for gene optimization aims to improve gene expression and therefore the synthetic amylase genes in this study were codon-optimized for expression in S. cerevisiae. However, results from this study indicated that increased gene expression and protein secretion was not guaranteed by codon optimization (FIGS. 2 and 3).

Figure 3:
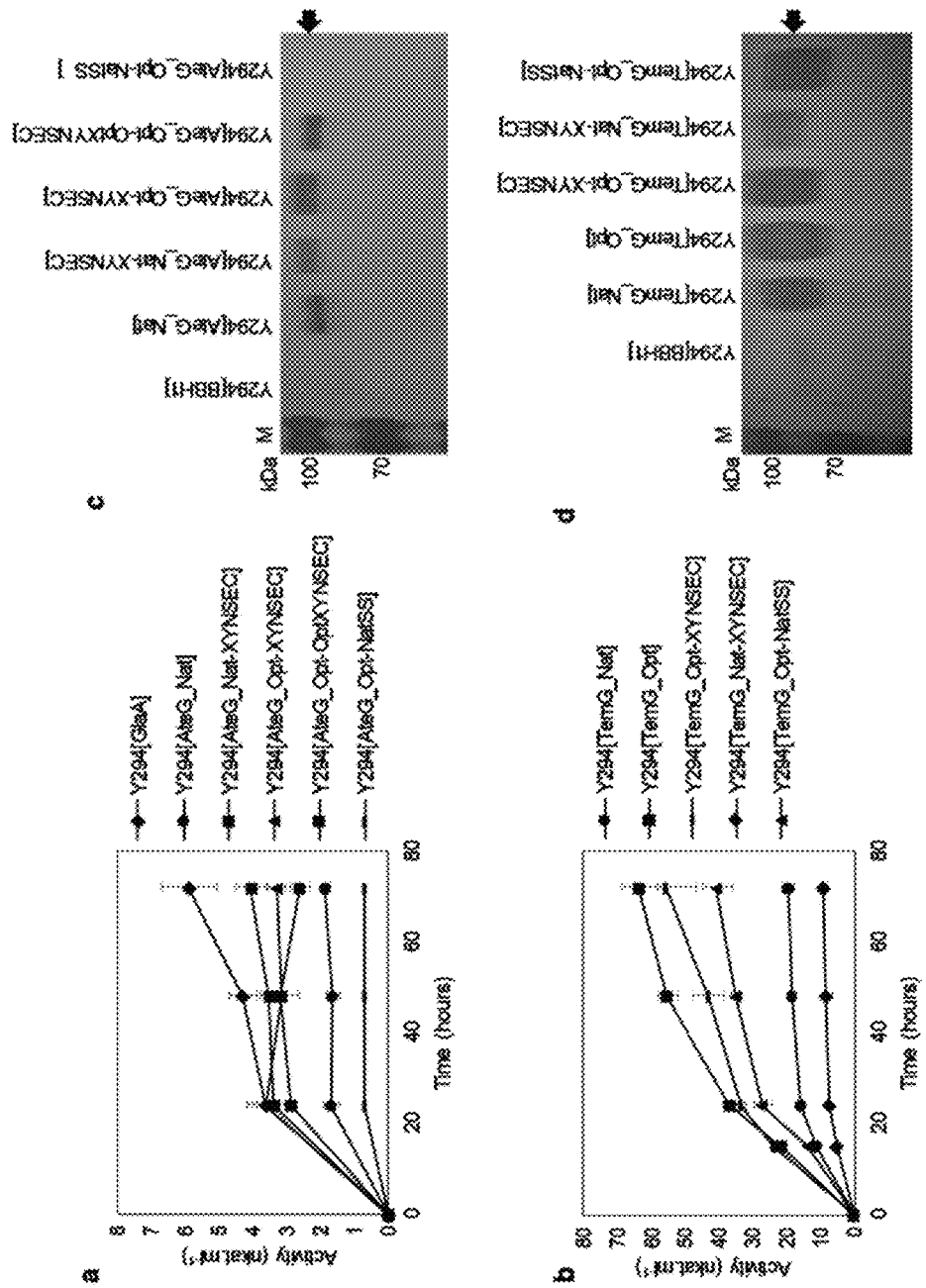
FIG. 3 Extracellular glucoamylase activity displayed by the *S. cerevisiae* Y294 strains expressing the (a) ateG and (b) temG gene derivatives, respectively. The *S. cerevisiae* Y294 [GlaA] strain was used for benchmark glucoamylase production. Values represent the mean of three repeats and error bars represent the standard deviation. Supernatant from the *S. cerevisiae* Y294 strains (after 72 hours) was subjected to SDS-PAGE followed by silver staining. The arrows indicate the presence of the recombinant (c) AteG and (d) TemG protein species, respectively. The *S. cerevisiae* Y294[BBH1] strain was used as the reference strain and the protein size marker (M) is depicted on the left hand side.

The strains expressing the apuA_Nat and temA_Nat genes were superior to the strains expressing the codon-optimized counterparts apuA_Opt-NatSS/apuA_Opt-OptXYNSEC and temA_Opt, respectively (FIGS. 2b and 2c), while optimization of the temG coding sequence resulted in a significant increase in TemG_Opt protein secreted by the S. cerevisiae Y294[TemG_Opt] strain (FIG. 3d). Increased recombinant protein secretion correlated with enhanced levels of extracellular activity, which suggested similar specific activities (FIGS. 2e and 2f) and SDS-PAGE analysis indicated that codon optimization did not affect amylase protein size (FIGS. 2 and 3). Based on the deduced amino acid sequences, the predicted molecular weights of the unglycosylated amylases are around 64-70 kDa, which is in agreement with previous reports on similar amylases (Gupta et al., 2003).

The temA_Nat had a CAI of 0.61 compared to temA_Opt with a CAI of 0.91. Surprisingly, however, the S. cerevisiae Y294[TemA_Nat] strain produced 59% more extracellular α-amylase activity than the S. cerevisiae Y294[TemA_Opt] strain after 72 hours. The temG_Nat gene had a CAI of 0.58 compared to temG_Opt, which had a CAI of 0.91. The extracellular glucoamylase activity for the S. cerevisiae Y294[TemG_Nat] and Y294[TemG_Opt] strains represented a >3-fold and 10-fold fold improvement, respectively, compared to the S. cerevisiae Y294[GlaA] benchmark strain. Therefore, even for genes originating from the same species (in this case T. emersonii), significant differences in protein secretion and extracellular enzyme activities were observed between native and codon-optimized genes. Thus, CAI values alone cannot be relied upon for improving gene expression.

The secretion of recombinant proteins into the culture medium simplifies downstream purification methods (Damasceno et al., 2012). Secretion signals are used to direct the propeptide to the endoplasmic reticulum (ER) and then through the secretory pathway (Futatsumori-Sugai and Tsumoto, 2010). Once in the ER, the mature peptide is folded into its native structure and there are a number of factors that effect this folding process (Tyo et al., 2012). The secretion of recombinant proteins by yeast is a key industrial objective for the biotechnology field, and significant efforts have gone into improving protein secretion. This process is dependent on the target protein, host strain and secretion signal sequence (Hashimoto et al., 1998). Therefore, signal peptides represented an important factor to consider when improving the concentration of secreted protein.

The XYNSEC secretion signal from Trichoderma reesei's β-xylanase 2 gene has been used successfully for the secretion of a number of proteins (van Wyk et al., 2010; van Rensburg et al., 2012; Favaro et al., 2013) and was used in this study for comparative purposes. All the native enzymes selected for this study were successfully secreted using their native secretion peptides, and the replacement of the native ateG signal peptide encoding sequence with the XYNSEC sequence resulted in enhanced extracellular activity (FIG. 3a). However, in general, the XYNSEC secretion signal was less effective than the proteins' native secretion signals.

Following the identification of successful amylase candidates, novel gene combinations were expressed in S. cerevisiae Y294 in order to obtain an amylolytic yeast suitable for raw starch CBP. It was previously reported that starch fermentation by genetically engineered strains is limited by the glucoamylase activity (Inlow et al., 1988), but in a more recent review the limiting factor in raw starch hydrolysis was attributed to α-amylase activity (Görgens et al., 2015). The type of starchy biomass (used as substrate) is likely to affect the ratio of amylases, but if a recombinant amylolytic yeast is able to produce highly active enzymes, an exact ratio should not be a limiting factor.

During cultivation on 200 $g \cdot l^{-1}$ raw corn starch, simultaneous expression of the α-amylase and glucoamylase combinations in S. cerevisiae resulted in varying ethanol yields (FIGS. 4a and b). After 72 hours, the carbon conversion displayed by the S. cerevisiae Y294[TemG_Opt-TemA_Nat] strain was 2.7-fold higher than the S. cerevisiae Y294 [AmyA-GlaA] benchmark strain. The S. cerevisiae Y294 [TemG_Opt-ApuA_Nat] and Y294[TemG_Opt-AteA_Nat] strains also outperformed the S. cerevisiae Y294[AmyA-GlaA] benchmark strain (FIG. 4a) in the early stages of fermentation (>2.4-fold higher ethanol concentrations after 48 hours). Substantially higher ethanol concentrations were obtained, compared to the modified amylolytic yeast strain constructed by Yamakawa et al. (2012), which produced 46.5 $g \cdot l^{-1}$ ethanol from 200 $g \cdot l^{-1}$ of raw corn starch. Furthermore, these results showed considerable improvements when compared to amylolytic CBP systems listed in a recent review by Salehi Jouzani and Taherzadeh, (2015). The carbon conversion displayed by the S. cerevisiae Y294 [TemG_Opt-TemA_Nat] strain on raw corn starch (Table 3) represented the highest reported for amylolytic S. cerevisiae Y294 strains in fermentations with high substrate loading and low inoculums.

Overall, S. cerevisiae recombinant strains with higher levels of glucoamylase, i.e. those expressing the temG_Opt glucoamylase, hydrolysed starch better than the S. cerevisiae Y294 strains with the temG_Nat glucoamylase. However, S. cerevisiae Y294[TemG_Opt-TemA_Nat] displayed a significantly higher carbon conversion (~1.6-2.0 fold) compared any of the other recombinant S. cerevisiae Y294 strains expressing the temG_Opt glucoamylase (Table 3). This suggested that there was a unique synergistic effect between the T. emersonii TemG_Opt and TemA_Nat enzymes that outperformed the other TemG_Opt-α-amylase combinations.

A synergistic effect was also observed for the A. tubingensis enzyme combination. At 192 hours, the carbon conversion displayed by the S. cerevisiae Y294[GlaA-AmyA] strain (54%) was 9% higher than the carbon conversion displayed by the S. cerevisiae Y294[TemG_Opt-AmyA] strain (49%) (Table 3), even though TemG_Opt was superior to GlaA in terms of activity (FIG. 3). This highlighted the importance of comparing different enzyme combinations in the chosen expression host. Even though extracellular amylase activities differed (FIGS. 2 and 3), enzymes originating from the same host may have a superior synergistic hydrolytic effect as a result of their modes of action and affinity for raw starch. Presečki et al. (2013) developed a mathematical model to explain the synergism between a glucoamylase and two α-amylases (in different combinations) and showed that the type and combinations of amylases affected enzyme synergy. Furthermore, whether an α-amylases is classified as "liquefying" or "saccharifying" may also attribute to the synergist relationship (Liakopoulou-Kyriakides et al., 2001).

The AmyA α-amylase displayed a greater extracellular activity on soluble starch, compared to the AteA_Nat enzyme (FIG. 2a). However, during fermentation studies the AteA_Nat α-amylase combinations facilitated a faster rate of raw starch conversion compared to the enzyme combinations with AmyA (FIG. 4). AteA_Nat also contributed to higher ethanol productivity levels (compared to AmyA) when combined with the TemG_Opt and TemG_Nat glucoamylases, respectively (FIG. 4 and Table 3). This suggested that AteA_Nat may have performed better on raw starch compared to the AmyA enzyme, or it had a superior synergistic effect with the TemG glucoamylase.

Dissimilarly, the extracellular activity produced by the S. cerevisiae Y294[ApuA_Nat] strain (expressing the native α-amylase from A. pullulans) was 2.7-fold higher than that of the S. cerevisiae Y294[AmyA] benchmark strain (FIGS. 2a and b), but overall the carbon conversion displayed by the amylolytic S. cerevisiae Y294[TemG_Opt-ApuA_Nat] strain was 13% lower than the S. cerevisiae Y294 [TemG_Opt-AmyA] strain (Table 3). Therefore, AmyA may either have had improved raw starch converting ability, or a better synergistic relationship with TemG_Opt, compared to ApuA_Nat (FIG. 4a). Chi et al. (2009) demonstrated that the glucoamylase from *A. pullulans* hydrolysed potato starch granules (type-B crystallinity) better than raw corn starch granules (type-B crystallinity), although type-B starch structures are usually more resistant to enzyme hydrolysis (Man et al., 2013). Corn starch has a higher amylose content and smaller granule diameter compared to potato starch (Hii et al., 2012) and the combination of these properties are known to influence the rate and extent of starch hydrolysis (Naguleswaran et al., 2013). Results from this study (FIGS. 2 and 4) highlighted a prime example where starch structure affected the action of different amylolytic enzymes.

Figure 6:
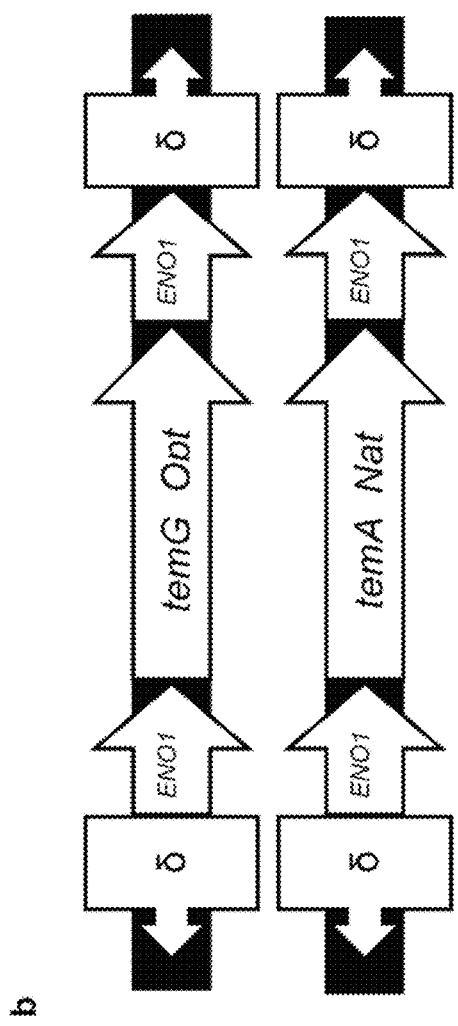
FIG. 6 Schematic representation of the final vector and gene cassettes used in this study. The TEF$_P$-amdSYM-TEF$_T$ cassette (a) was cloned onto yBBH1 to generate the yBBH1-amdSYM expression vector. The ENO1 temA_Nat and temG_Opt gene cassettes (b) were amplified using PCR and contained flanking regions homologous to the δ integration sites.
Figure 6:
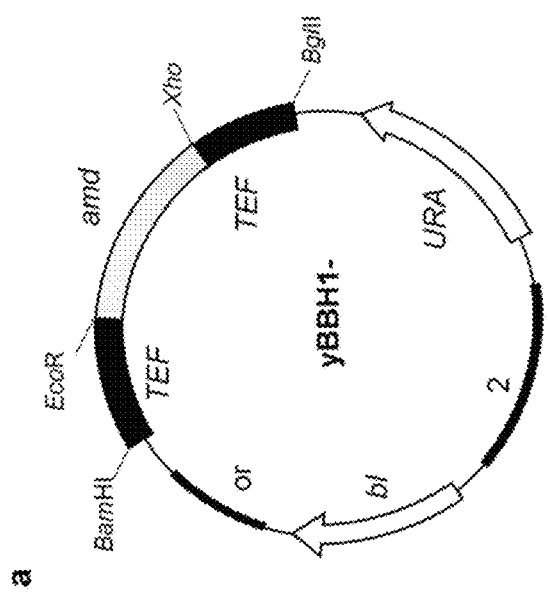

Although *S. cerevisiae* is known for its ethanol tolerance, the Y294 strains were inhibited by fermentation conditions at an incubation temperature of 30° C. and thus ethanol concentrations did not exceed 63 g·l$^{-1}$ (FIGS. 5 and 6). The poor fermentative performance by the *S. cerevisiae* Y294 laboratory strain was not as a result of inadequate recombinant protein secretion or low enzymatic activity, since glucose concentrations increased rapidly throughout the fermentation with the *S. cerevisiae* Y294[TemG_Opt-TemA_Nat] strain (FIG. 4b).

Raw starch fermentation by recombinant *S. cerevisiae* strains is often disadvantaged by long cultivations times required for sufficient enzyme secretion. However, it was clear from the fermentation results for the *S. cerevisiae* Y294[TemG_Opt-TemA_Nat] strain (FIG. 5) that volumetric productivity and starch conversion rates were high. Furthermore, a cultivation temperature of 26° C. relieved physiological stress on the yeast cells, allowing for improved glucose conversion. After 192 hours, the carbon conversion displayed by the *S. cerevisiae* Y294[TemG_Opt-TemA_Nat] strain was the similar (81-85%) for the 100 ml serum bottles and bioreactor fermentations, respectively (Table 4.3 and FIG. 4.5b). Thus suggesting that the lower temperature was the main factor to favour glucose fermentation and that the extracellular enzyme activity was not significantly affected by a lower temperature (since the final carbon conversion remained the same at both fermentation temperatures). Therefore, decreasing the fermentation temperature confirmed that it was possible to increase the conversion of glucose to ethanol and improve the theoretical ethanol yield.

Schmidt et al. (2006) provided several definitions for ethanol tolerance, one of which was the effect of ethanol concentrations on the ability of a cell to metabolise sugar. Biochemical and physiological responses occur when yeast are exposed to accumulating ethanol concentrations (Schmidt et al., 2006) and as a result *S. cerevisiae* Y294 strains were likely to experience compromised membrane structure and protein function. The presence of ethanol changes the composition of the phospholipid bilayer making it permeable to small molecules. Since many cellular functions rely on membrane integrity, high ethanol concentrations can have a number of adverse effects on the yeast cell. In this study, the negative effects of ethanol accumulation could be avoided by lowering the fermentation temperature to 26° C.

Conclusion

Currently, industry lacks the implementation of an amylolytic CBP yeast that simultaneously expresses both an α-amylase and glucoamylase. This study focused on the selection of highly active amylases with the ability to convert raw starch to glucose. This led to the identification and evaluation of novel amylase combinations for the hydrolysis of raw starch. The recombinant *S. cerevisiae* Y294 [TemG_Opt-TemA_Nat] strain was superior in its ability to convert 85% of the available carbon in 200 g·l$^{-1}$ raw corn starch fermentation within 192 hours. Thus, this unique TemG_Opt-TemA_Nat enzyme combination represents a promising candidate for the industrial conversion of uncooked starch.

Example 2: Construction of Amylolytic CBP *S. cerevisiae* Ethanol Red™ and M2n Strains Materials and Methods Media and Cultivation Conditions All chemicals were of analytical grade and were obtained from Merck (Darmstadt, Germany), unless otherwise stated. *Escherichia coli* DH5α (Takara Bio Inc.) was used for vector propagation. The *E. coli* transformants were selected for on Luria Bertani agar (Sigma-Aldrich, Germany), containing 100 µg·ml$^{-1}$ ampicillin and cultivated at 37° C. in Terrific Broth (12 g·l$^{-1}$ tryptone, 24 g·l$^{-1}$ yeast extract, 4 ml·l$^{-1}$ glycerol, 0.1 M potassium phosphate buffer) containing 100 µg·ml$^{-1}$ ampicillin for selective pressure (Sambrook et al., 1989).

The *S. cerevisiae* parental strains were maintained on YPD agar plates (10 g·l$^{-1}$ yeast extract, 20 g·l$^{-1}$ peptone, 20 g·l$^{-1}$ glucose and 20 g·l$^{-1}$ agar). The *S. cerevisiae* Y294 transformants were selected for and maintained on SC$^{-URA}$ agar plates (6.7 g·l$^{-1}$ yeast nitrogen base without amino acids (BD-Diagnostic Systems, Sparks, Md.), 20 g·l$^{-1}$ glucose and 1.5 g·l$^{-1}$ yeast synthetic drop-out medium supplements (Sigma-Aldrich, Germany) and 20 g·l$^{-1}$ agar). *S. cerevisiae* strains were aerobically cultivated on a rotary shaker (200 rpm) at 30° C., in 125 ml Erlenmeyer flasks containing 20 ml double strength SC$^{-URA}$ medium (2×SC$^{-URA}$ containing 13.4 g·l$^{-1}$ yeast nitrogen base without amino acids (BD-Diagnostic Systems, Sparks, Md.), 20 g·l$^{-1}$ glucose and 3 g·l$^{-1}$ yeast synthetic drop-out medium supplements). Fermentation media for *S. cerevisiae* Y294 strains comprised of 2×SC$^{-URA}$ containing 5 g·l$^{-1}$ glucose and 200 g·l$^{-1}$ raw corn starch, whereas the medium for *S. cerevisiae* Ethanol Red™ from Fermentis and M2n strains was YP containing 5 g·l$^{-1}$ glucose and 200 g·l$^{-1}$ raw corn starch. Ampicillin (100 µg·ml$^{-1}$) and streptomycin (50 µg·ml$^{-1}$) were added to inhibit bacterial contamination. All cultures were inoculated to a concentration of 1×10$^6$ cells·ml$^{-1}$, unless otherwise stated.

SC media (yeast synthetic drop-out medium omitted) containing 2% starch was used to maintain industrial transformants. The *S. cerevisiae* Ethanol Red™ and M2n transformants were selected for on SC-Ac plates (SC plates with (NH$_4$)$_2$SO$_4$ replaced by 0.6 g·l$^{-1}$ acetamide and 6.6 g·l$^{-1}$ K$_2$SO$_4$) and transferred to SC-Acr plates (SC-Ac with 0.71 g·l$^{-1}$ acrylamide replacing the acetamide). For plate assays, 2% soluble starch was added to SC-Ac and SC-Acr plates. SC-Fac plates (SC media containing 2.3 g·l$^{-1}$ fluoroacetamide) was used to remove the yBBH1-amdSYM vector from the transformants. The pH in all the media was adjusted to 6.0 with NAOH.

Strains and Plasmids

The genotypes of the bacterial and yeast strains, as well as the plasmids used in this study, are summarised in Table 4.

TABLE 4

Strains and plasmids used in this study

| Strains and plasmids | Genotype | Reference/Source |
|---|---|---|
| E. coli DH5α | supE44 ΔlacU169 (φ80lacZΔM15) hsdR17 recA1 endA1 gyrA96 thi-1 relA1 | Sambrook et al. (1989) |
| *S. cerevisiae* strains | | |
| Y294 | α leu2-3,112 ura3-52 his3 trp1-289 | ATCC 201160 |
| Y294[amdSYM] | URA3 TEF$_P$-amdS-TEF$_T$ | This study |
| Y294[TemG_Opt-TemA_Nat] | URA3 ENO1$_P$-temG_Opt-ENO1$_T$; ENO1$_P$-temA_Opt-ENO1$_T$ | This study |
| Ethanol Red ™[1] | MATa/α prototroph | Fermentis, Lesaffre, France |
| M2n | MATa/α prototroph | Favaro et al. (2015) |
| Ethanol Red ™ T1[2] | δ-integration of ENO1$_P$-temG_Opt-ENO1$_T$; ENO1$_P$-temA_Nat-ENO1$_T$ | This study |
| Ethanol Red ™ T12[2] | δ-integration of ENO1$_P$-temG_Opt-ENO1$_T$; ENO1$_P$-temA_Nat-ENO1$_T$ | This study |
| Ethanol Red ™TemA_Nat | δ-integration of ENO1$_P$-temA_Nat-ENO1$_T$ | This study |
| M2n T1[2] | δ-integration of ENO1$_P$-temG_Opt-ENO1$_T$; ENO1$_P$-temA_Nat-ENO1$_T$ | This study |
| M2n T2[2] | δ-integration of ENO1$_P$-temG_Opt-ENO1$_T$; ENO1$_P$-temA_Nat-ENO1$_T$ | This study |
| M2n[TLG1-SFA1] | TLG1 and SFA1 multiple copy integration | Favaro et al. (2015) |
| Plasmids | | |
| yBBH1 | bla URA3 ENO1$_P$-ENO1$_T$ | Njokweni et al. (2012) |
| yBBH1-TemA_Nat[3] | bla URA3 ENO1$_P$-temA_Nat-ENO1$_T$ | This study |
| yBBH1-TemG_Opt[4] | bla URA3 ENO1$_P$-temG_Opt-ENO1$_T$ | This study |
| yBBH1-TemG_Opt-TemA_Nat | bla URA3 ENO1$_P$-temG_Opt-ENO1$_T$; ENO1$_P$-temA_Nat-ENO1$_T$ | This study |
| pUG-amdSYM[5] | bla TEF$_P$-amdS-TEF$_T$ | Solis-Escalante et al. (2013) |
| yBBH1-amdSYM | bla URA3 TEF$_P$-amdS-TEF$_T$ | This study |

[1]Ethanol Red ™ Version 1, referred to as Ethanol Red ™
[2]Amylolytic transformants (T) contain integrated copies of ENO1$_P$-temA_Nat-ENO1$_T$ and ENO1$_P$-temG_Opt-ENO1$_T$ gene cassettes, the number indicates the transformant number during the screening process
[3]Accession no. XM_013469492 for the native *T. emersonii* α-amylase (temG_Nat)
[4]Accession no. AJ304803 for the native *T. emersonii* glucoamylase (temG_Opt encodes for the codon-optimized gene)
[5]Assession no. P30669 for pUG-amdSYM plasmid DNA Manipulations Standard protocols were followed for all DNA manipulations and *E. coli* transformations (Sambrook et al., 1989). The enzymes used for restriction digests and ligations were purchased from Inqaba Biotec and used as recommended by the supplier. Digested DNA was eluted from 0.8% agarose gels using the Zymoclean™ Gel DNA Recovery Kit (Zymo Research, USA). The temA_Nat and temG_Opt gene cassettes (ENO1 promoter and terminator) (FIG. 1b) were amplified through PCR using Delta-ENO1 primers (Table 5), together with the yBBH1[TemA_Nat] and yBBH1[TemG_Opt] vectors (see Example 1), respectively, as template.

Plasmid Construction

The TEF$_P$-amdSYM-TEF$_T$ gene cassette was amplified from pUG-amdSYM through PCR using amdSYMCas primers (Table 5) and cloned onto yBBH1 using yeast-mediated ligation (YML) yielding plasmid yBBH1-amdSYM (FIG. 6a). The *Ashbya gossypii* TEF promoter regulated the expression of the acetamidase-encoding gene (amdS) for the selection of transformants on SC-Ac plates. The yBBH1-amdSYM plasmid was retrieved from the *S. cerevisiae* Y294[amdSym] strain and transformed into *E. coli* DH5α in order to obtain a high concentration of plasmid DNA. Plasmid DNA was isolated using the High Pure Plasmid Isolation kit (Roche, Germany) and sequence verification was performed by the dideoxy chain termination method, with an ABI PRISM™ 3100 Genetic Analyser (CAF, Stellenbosch University).

TABLE 5

PCR primers designed and used in this study with the relevant restriction sites underlined (EcoRI = gaattc; XhoI = ctcgag, BamHI = ggatcc, BglII = agatct)

| Primer name | Sequence (5'-3') | SEQ ID NO: |
|---|---|---|
| amdSYMCas: L | ccgcgcgttggccgattcattaatcca<u>ggatcc</u>acatggaggcccagaatacccctccttgac | 37 |
| amdSYMCas: R | gggcctcttcgctattacgccagagctt<u>agatct</u>cagtatagcgaccagcattcacatacttaa | 38 |
| Delta- | tggaataaaaatccactatcgtctatcaactaatagttatattatcaatatattatcatatacg | 39 |

TABLE 5 -continued

PCR primers designed and used in this study with the relevant restriction sites
underlined (EcoRI = gaattc; XhoI = ctcgag, BamHI = ggatcc, BglII = agatct)

| Primer name | Sequence (5'-3') | SEQ ID NO: |
|---|---|---|
| ENO1p: L | gtgttaagatgatgacataagttatgagaagctgtcggatcccaattaatgtgagttacctcac | |
| Delta-ENO1t: R | tgagatatatgtgggtaattagataattgttgggattccattgttgataaaggctataatatta<br>ggtatacagaatatactagaagttctcctcgaggatagatctcctatgcggtgtgaaataccgc | 40 |
| TemG_Opt: L | ttatcaacacacaaacactaaatcaaagaattcatggcctccttagtcgcaggtgcctta | 41 |
| TemG_Opt: R | gactagaaggcttaatcaaaagctctcgagtcattgccaagagtcgtccaagattgcggt | 42 |
| TemA_Nat: L | tgcttatcaacacacaaacactaaatcaaagaattcatgacgcctttcgtcctcacggcc | 43 |
| TemA_Nat: R | ggactagaaggcttaatcaaaagctctcgagctatctccatgtgtcgacaatcgtctccg | 44 |

Yeast Transformations

Electro-competent *S. cerevisiae* Y294, Ethanol Red™ and M2n cells were prepared according to Cho et al. (1999) and transformed by means of electroporation using a BioRad system (GenePluserXcell™, Bio-Rad, Hercules, Calif.). For the transformation of industrial strains, amylases (temA_Nat and temG_Opt ENO1 linear DNA cassettes) and the yBBH1-amdSYM vector containing the selection marker (FIG. 6) were simultaneously transformed into the genomes of the yeasts. After electroporation, 1 ml of YPDS was immediately added to the cuvettes. Cells were incubated at 30° C. for 3 hours. Transformants were selected for by plating the transformation mix on to SC-Ac plates containing 2% starch (adapted from Solis-Escalante et al., 2013) and incubated at 30° C. for 4 days. The integration of the linear expression cassette DNA into the yeast genome was confirmed by PCR using gene specific primers (Table 5).

Marker Recycling

Plasmid curing was performed on the industrial recombinant strains as described by Solis-Escalante et al. (2013). The removal of the yBBH1-amdSYM containing the acetamide marker was achieved by growing cells overnight in 5 ml liquid YPD and transferring 20 µl to a 125 ml Erlenmeyer flask containing 10 mL SC-Fac. Marker-free single colonies were obtained by plating 100 µl of culture on SC-Fac solid media containing 2% starch and confirmed by colony PCR. The genomic DNA of the amylolytic strains was isolated using the ZR fungal/bacterial DNA miniprep kit (Zymo Research, USA) and it was then used as a template for real-time PCR.

Quantitative PCR

Oligo primers for real-time PCR were designed using IDT's PrimerQuest Tool (eu.idtdna.com/PrimerQuest/Home/Index). Special attention was given to primer length (18-22 bp), annealing temperature (58-62° C.), base composition, 3'-end stability and amplicon size (75-100 bp). All primers were synthesised by Inqaba Biotech (South Africa) with reverse phase cartridge purification and are listed in Table 6. The performance of all primers was experimentally confirmed by conventional PCR to ensure that there was no formation of primer dimers and confirm the amplification of a single region with the correct amplicon length.

TABLE 6

List of candidate reference genes and target genes including details of primers and amplicons for each gene

| Gene name | Amplicon length (bp) | Primers (5'-3') | SEQ ID NO: |
|---|---|---|---|
| URA3 | 92 | L: cgtggatgatgtggtctctac<br>R: gttcaccctctaccttagcatc | 45<br>46 |
| temA_Nat | 100 | L: gcgatgtcactgagaggatcta<br>R: gaaatccagatggccgtgaa | 47<br>48 |
| temG_Opt | 95 | L: tacaggtggtttgggtgaac<br>R: ctctcaatgctggaccatctc | 49<br>50 |

Real-time PCR was carried out on a StepOne real time Polymerase Chain Reaction (PCR) instrument (Applied Biosystems) using white-walled PCR plates (96 wells). A ×2 KAPA HRM Fast Master Mix (containing a fast proof-reading polymerase, dNTPs, stabilisers and EvaGreen® dye) was used according to the manufacturer's instructions (KAPA Biosystems). Reactions were prepared in a total volume of 20 µl containing, 2.5 mM $MgCl_2$, 0.2 µM of each primer and 1-10 ng DNA. The cycle conditions were set as follows: initial template denaturation at 95° C. for 30 seconds, followed by 45 cycles of denaturation at 95° C. for 5 seconds and combined primer annealing/elongation at 60° C. for 20 seconds and a final denaturation at 95° C. for 1 minute to ensure all amplicons were fully melted. The yBBH1-TemG_Opt-TemA_Nat plasmid DNA was used to set up the standard curves (starting with $1 \times 10^7$ copies and making a 1:10 serial dilution) using primer pairs listed in Table 6. Genomic DNA concentrations were standardised to 10 ng for all samples. The PCR efficiency for each of the primer sets was calculated using StepOne software (Applied Biosystems). The number of copies of the temG_Opt and temA_Nat genes was calculated using the standard curve method using the URA3 gene as reference gene.

Raw Starch Fermentations

The *S. cerevisiae* Y294 precultures were cultured in 100 ml $2 \times SC^{-URA}$ medium in 500 ml Erlenmeyer flasks, and the *S. cerevisiae* Ethanol Red™ and M2n precultures were cultivated similarly in YPD medium. All precultures were incubated at 30° C. with agitation at 200 rpms until stationary phase. *S. cerevisiae* Y294 fermentations were performed in $2 \times SC^{-URA}$ media, whereas *S. cerevisiae* Ethanol Red™ and M2n fermentations were performed in YP media (10 g·l$^{-1}$ yeast extract and 20 g·l$^{-1}$ 1 peptone). All media was supplemented with 200 g·l$^{-1}$ raw corn starch and 5 g·l$^{-1}$ glucose as carbohydrate sources and inoculated with a 10% (v·v$^{-1}$) inoculum from the stationary preculture. Ampicillin (100 μg·ml$^{-1}$) and streptomycin (50 μg·ml$^{-1}$) were added to inhibit bacterial contamination. Agitation and incubation were performed on a magnetic multi-stirrer platform (Velp Scientifica, Italy) at 30° C. and 37° C., with daily sampling through a syringe needle pierced through the rubber stopper.

Exogenous enzymes used in the fermentation processes were STARGEN™ 002 GSHE (now referred to as STARGEN™), obtained from Dupont Industrial Biosciences (Palo Alto, Calif.), with an activity minimum of 570 GAU·gm$^{-1}$ (www.genencor.com) and used according to the manufacturer's instructions. STARGEN™ contained *Aspergillus kawachii* α-amylase expressed in *Trichoderma reesei* and a glucoamylase from *T. reesei* that works synergistically to hydrolyse granular starch to glucose (Huang et al., 2015). Exogenous amyloglucosidase (E.C. 3.2.1.3) from *Aspergillus niger* was purchased from Sigma-Aldrich and used to spike the fermentations with extra glucoamylase enzyme (now referred to as commercial glucoamylase).

For bioreactor experiments with the Ethanol Red™ T12 strain, precultures were cultivated in 400 ml YPD in 2 liter Erlenmeyer flasks at 30° C. Fermentations were performed in a Minifors 2 bioreactor (INFORS HT, Bottmingen, Switzerland) containing YP supplemented with 200 g·l$^{-1}$ raw corn starch and 5 g·l$^{-1}$ glucose as carbohydrate source. A 10% (v·v$^{-1}$) inoculum was used in a total working volume of 3 liters. Ampicillin (100 μg·ml$^{-1}$) and streptomycin (50 μg·ml$^{-1}$) were added to inhibit bacterial contamination. Fermentations were carried out at 30° C., 34° C. and 37° C., with agitation at 300 rpm.

HPLC and Analytical Methods

Ethanol, glucose, maltose, glycerol and acetic acid concentrations were quantified with high performance liquid chromatography (HPLC) using a Surveyor Plus liquid chromatograph (Thermo Scientific) consisting of a liquid chromatography pump, autosampler and refractive index (RI) detector. The compounds were separated on a Rezex RHM Monosaccharide 7.8×300 mm column (00H0132-K0, Phenomenex) at 80° C. with 5 mM $H_2SO_4$ as mobile phase at a flow rate of 0.6 ml·min$^{-1}$.

The theoretical $CO_2$ concentrations were calculated according to Favaro et al. (2015). The available carbon (mol C in 100% hydrolysed substrate) was calculated based on the available glucose equivalents and the carbon conversion is defined as the percentage starch converted to fermentable products on a mol carbon basis. This carbon conversion was calculated from ethanol, glucose, maltose, glycerol, acetic acid and $CO_2$ concentrations. The ethanol yield (% of the theoretical yield) was calculated as the amount of ethanol produced per gram of consumed sugar. The ethanol rate of productivity was calculated based on ethanol titres produced per hour (g·l$^{-1}$·h$^{-1}$).

Statistical Analysis

Data was analysed using the Student's t-test.

Results

The *T. emersonii* temA_Nat and temG_Opt genes encode for valuable amylase enzymes for use in the production of biofuel and are produced and secreted during cultivation on raw corn starch. The linear ENO1$_P$-temA_Nat-ENO1$_T$ and ENO1$_P$-temG_Opt-ENO1$_T$ DNA gene cassettes (FIG. 6b), flanked by the δ sequence, were amplified and integrated into the δ-integration sites in the *S. cerevisiae* Ethanol Red™ and M2n industrial strains' genomes, in order to generate multi-copy integrants (Kim et al., 2011). The amdS gene was present on an episomal vector (FIG. 6a) to enable plasmid curing for easy recycling of the marker.

Industrial Strain Screening

*S. cerevisiae* transformants were screened on SC plates containing 2% corn starch and those producing zones of hydrolysis were selected for further testing. PCR was used to confirm the integration of both ENO1$_P$-temA_Nat-ENO1$_T$ and ENO1$_P$-temG_Opt-ENO1$_T$ gene cassettes. The four strains showing the highest extracellular amylase activity were then evaluated under fermentative conditions (FIGS. 7a and 7b). Significant differences in the carbon conversion displayed by the industrial strains was noted during the early stages of fermentation (FIG. 7b). However, after 192 hours the carbon conversion started to plateau, representing an approximate 80% conversion of corn starch. The *S. cerevisiae* Ethanol Red™ T12 and M2n T1 strains hydrolysed starch and fermented the sugars quicker than the *S. cerevisiae* Ethanol Red™ T1 and M2n T2 strains (FIG. 7b and Table 7). They were therefore selected for further evaluation under different fermentation conditions.

Plasmid curing of the strains was performed by plating cultures onto SC-FAc plates containing 2% soluble corn starch. Quantitative PCR assays were performed using the genomic DNA from the cured amylolytic *S. cerevisiae* transformants, in order to determine the number of integrated copies of both temA_Nat and temG_Opt genes, respectively (FIG. 7d). The *S. cerevisiae* Ethanol Red™ T1, M2n T1 and M2n T2 strains contained single copies of temA_Nat and temG_Opt gene cassettes, whereas the *S. cerevisiae* Ethanol Red™ T12 contained 1 copy of temA_Nat and 2 copies of temG_Opt.

TABLE 7

Product formation by *S. cerevisiae* strains after 144 hours of fermentation at 30° C.

| *S. cerevisiae* | Ethanol Red ™ T1 | Ethanol Red ™ T12 | M2n T1 | M2n T2 |
|---|---|---|---|---|
| Substrate (g · l$^{-1}$) | | | | |
| Raw starch weighed | 200 | 200 | 200 | 200 |
| Glucose weighed | 5 | 5 | 5 | 5 |
| Raw starch (dry weight) | 185 | 185 | 185 | 185 |
| Glucose equivalent | 208.5 | 208.5 | 208.5 | 208.5 |
| Products (g · l$^{-1}$) | | | | |
| Glucose | 0.82 | 0.67 | 0.60 | 0.72 |
| Glycerol | 2.39 | 3.40 | 1.92 | 2.29 |
| Acetic acid | 0.49 | 0.46 | 0.76 | 0.35 |
| Ethanol | 57.76 | 74.19 | 72.19 | 64.68 |
| Maltose | 0.99 | 1.09 | 1.01 | 1.08 |
| $CO_2$[1] | 55.25 | 70.94 | 69.05 | 61.87 |
| Total | 117.68 | 150.76 | 145.53 | 131.00 |
| Carbon conversion (%) | 56.44 | 72.31 | 69.80 | 62.83 |
| Ethanol yield[2] (% of theoretical yield) | 55.41 | 71.17 | 69.25 | 62.05 |
| Ethanol rate of productivity[3] | 0.40 | 0.52 | 0.50 | 0.45 |

[1]$CO_2$ concentrations were deduced from the ethanol produced
[2]Ethanol yield (% of the theoretical yield) was calculated as the amount of ethanol produced per gram of consumed glucose
[3]Ethanol rate of productivity was calculated based ethanol titres produced per hour (g · l$^{-1}$ · h$^{-1}$)

Figure 8:
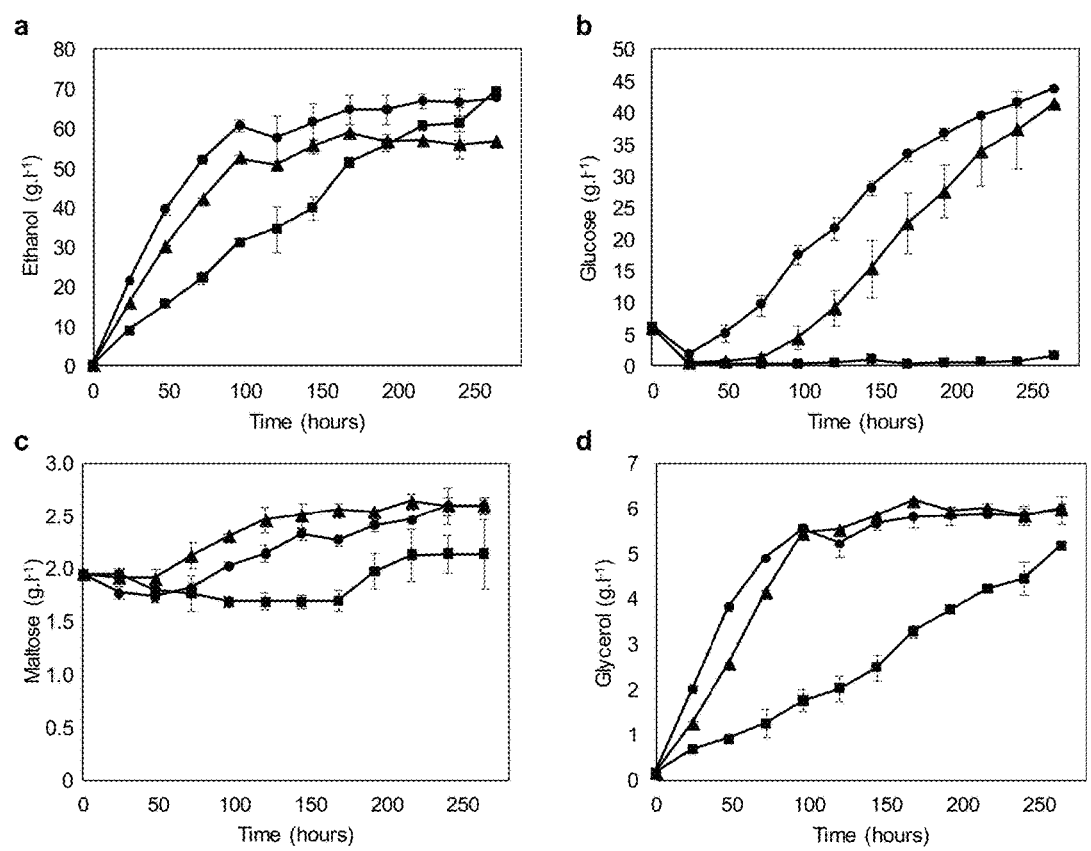
FIG. 8 Comparison between the laboratory S. cerevisiae Y294[TemG_Opt-TemA_Nat] strain (-●-) and the industrial amylolytic S. cerevisiae Ethanol Red™ T12 strain at 30° C. (-■-) and 37° C. (-▲-). The production of ethanol (a), glucose (b), maltose (c) and glycerol (d) were compared using 2×SC$^{-URA}$ fermentation media that contained 5 g·l$^{-1}$ glucose and 200 g·l$^{-1}$ raw corn starch. Data are the mean of 3 repeats showing standard deviation.

The fermentation vigour of the amylolytic *S. cerevisiae* Ethanol Red™ T12 strain at 30° C. and 37° C. was compared to the laboratory *S. cerevisiae* Y294[TemG_Opt-TemA_Nat] strain at 30° C. (FIG. 8). The *S. cerevisiae* Ethanol Red™ T12 strain was able to ferment all the available glucose (FIG. 8b) at a fermentation temperature of 30° C. and produced significantly less glycerol during the fermentation (FIG. 8d). This indicated a more efficient carbon conversion for ethanol (Bideaux et al., 2006). However, at a temperature of 37° C., ethanol levels did not increase significantly after 144 hours (FIG. 8a) and high level of residual glucose were present (>40 g·l$^{-1}$ after 264 hours). Maltose concentrations were similar at both fermentation temperatures (FIG. 8c).

Figure 9:
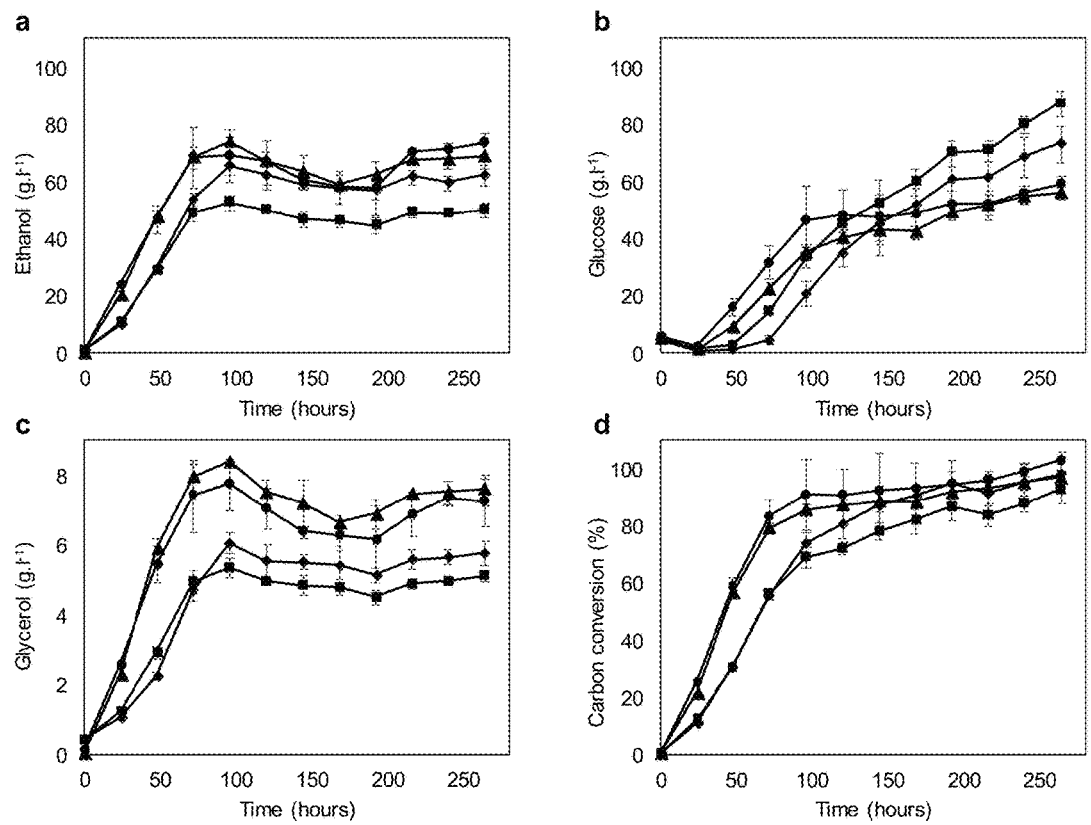
FIG. 9 Different fermentation broth conditions during fermentation at 37° C. on 200 g·l$^{-1}$ raw corn starch. S. cerevisiae Ethanol Red™ T12 in YP (-◆-), YP citrate-acid buffer pH 5 (-■-), SC citrate-acid buffer pH 5 (-●-) and SC citrate-acid buffer pH 5 with 10 g·l$^{-1}$ extra (NH$_4$)$_2$SO$_4$ (-▲-). Ethanol (a), glucose (b), glycerol concentrations (c) and carbon conversion (percentage starch converted on a mol carbon basis) (d) were compared. Data are the mean of 3 repeats showing standard deviation.

The evaluation of different media conditions (FIG. 9) was subsequently undertaken in order to determine whether buffered fermentation media (pH 5), the type of media (YP versus SC) or the addition of extra nitrogen (in the form of $(NH_4)_2SO_4$) could increase the efficiency of glucose fermentation by the *S. cerevisiae* Ethanol Red™ T12 strain at a fermentation temperature of 37° C. YP starch media (unbuffered) had a pH lower than 5 and this was more favourable for ethanol production, compared to the buffered YP broth (pH 5) (FIG. 9a). The addition of extra ammonium sulphate (10 g·l$^{-1}$) to the SC buffered fermentation broth did not increase ethanol concentrations or carbon conversion (FIGS. 9a and 9d), indicating sufficient nitrogen levels in the fermentation broth.

Increased residual glucose concentrations were observed when YP media was used (FIG. 9b), while higher glycerol concentrations were noted when the fermentation was performed in SC media (FIG. 9c). YP is more nutrient rich compared to the SC medium and a decreased formation of NADH formed from biosynthesis, therefore less glycerol. The higher glycerol concentrations contributed to increased carbon conversion values, especially during the first 120 hours of fermentation. Overall, the results in FIG. 9 showed that the media composition (SC vs YP and the pH) affected the ethanol and glycerol production. However, changes in the type of media only affected the percentage carbon conversion during the first 120 hours of fermentation. After 192 hours, the differences in carbon conversion values s was less apparent (between 92-100%).

Fermentations with STARGEN™

The recommended STARGEN™ dosage was calculated as 1.42 µl·g$^{-1}$ starch, according to the manufacturer's specifications. The amylolytic *S. cerevisiae* Ethanol Red™ T12 and M2n T1 strains were compared to a simulated conventional SSF process (parental *S. cerevisiae* Ethanol Red™/M2n strains+STARGEN™) at 200 g·l$^{-1}$ corn starch. Three different enzyme dosages were evaluated based on the percentage of the recommended enzyme loading: 2.8 µl (10%), 5.6 µl (20%) and 14 µl (50%) and compared to the SSF, which had 28 µl STARGEN™ per 100 ml (representing 100% of the recommended dosage). The addition of exogenous enzymes significantly increased ethanol concentrations and enhanced ethanol productivity (ethanol g·l$^{-1}$·h$^{-1}$) during the first 72 hours of fermentation (FIGS. 10 and 11).

At a fermentation temperature of 30° C. the ethanol profiles for the *S. cerevisiae* Ethanol Red™ and M2n parental strains were similar for the respective condition (FIGS. 10a and 11a). By 48 hours, the *S. cerevisiae* Ethanol Red™ T1 strain supplemented with 2.8 ul STARGEN™ produced the same amount of ethanol (52 g·l$^{-1}$) and displayed a similar carbon conversion (50%) to that of the control SSF process with untransformed *S. cerevisiae* Ethanol Red™ supplemented with 28 µl STARGEN™ (Table 8). A similar trend was observed for the *S. cerevisiae* M2n T1 strain supplemented with 2.8 µl STARGEN™ compared to the *S. cerevisiae* M2n parental strain (FIGS. 11a and c).

Figure 10:
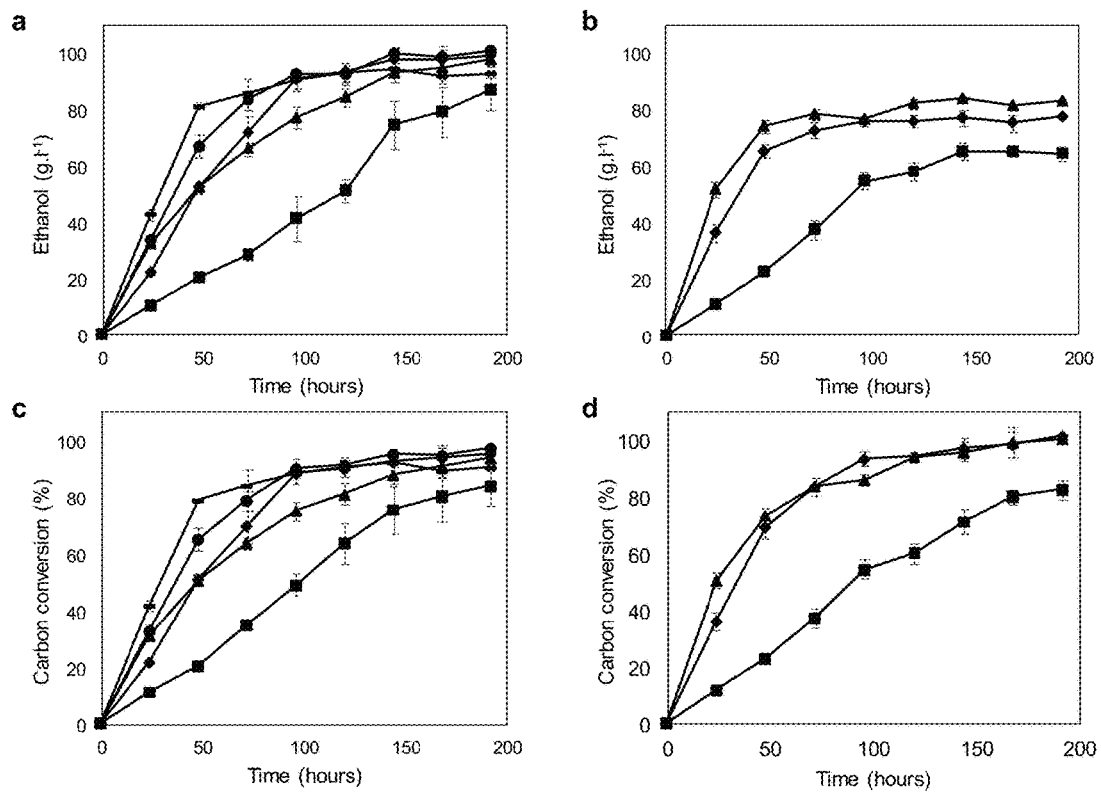
FIG. 10 Ethanol concentrations produced by S. cerevisiae Ethanol Red™ strains during fermentation with 200 g·l$^{-1}$ corn starch at 30° C. (a), at 37° C., (b), carbon conversion (percentage starch converted on a mol carbon basis) at 30° C. (c) and carbon conversion (percentage starch converted on a mol carbon basis) at 37° C. (d). Untransformed Ethanol Red™+28 μl STARGEN™ (-▲-), Ethanol Red™ T12 (-■-), Ethanol Red™ T12+2.8 μl STARGEN™ (-◆-), Ethanol Red™ T12+4.6 μl STARGEN™ (-●-) and Ethanol Red™ T12+14 μl STARGEN™ (--■--). Data are the mean of 3 repeats showing standard deviation.

After 96 hours, ethanol produced by the *S. cerevisiae* Ethanol Red T12 strain supplemented with 2.8 µl STARGEN (90.4 g·l$^{-1}$) was similar to the amount of ethanol produced by the *S. cerevisiae* Ethanol Red T12 strain supplemented with 5.6 µl STARGEN (92.0 g·l$^{-1}$) (FIG. 10). The carbon conversion displayed by these two strains was also similar (between 88-90%), at 96 hours (FIG. 10). This represented a significant increase in ethanol compared to the *S. cerevisiae* Ethanol Red control strain supplement with 28 µl STARGEN, which produced 76.8 g·l$^{-1}$ ethanol and displayed a 75% carbon conversion after 96 hours. Therefore, the addition of 2.8 µl STARGEN (10% of the recommended dosage) was sufficient to produce results that were comparable to an SSF control.

Figure 11:
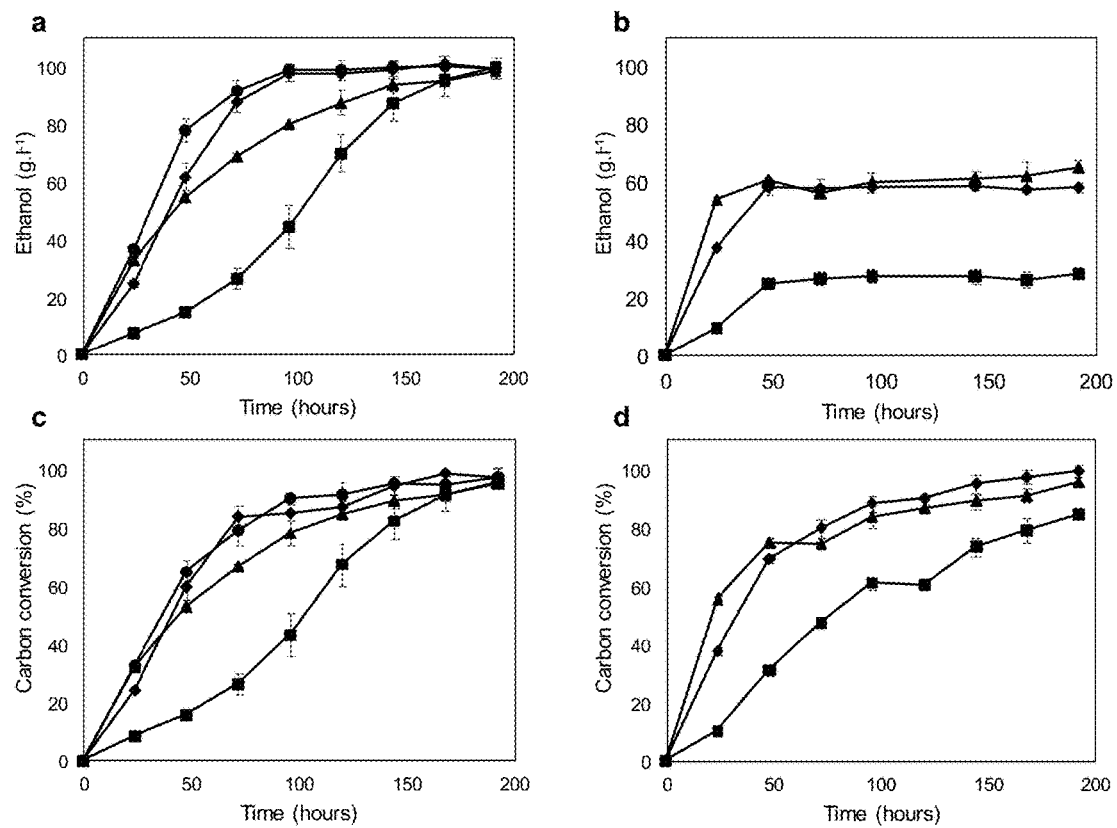
FIG. 11 Ethanol concentrations produced by S. cerevisiae M2n strains during fermentation with 200 g·l$^{-1}$ at 30° C. (a), at 37° C., (b), carbon conversion (percentage starch converted on a mol carbon basis) at 30° C. (c) and carbon conversion (percentage starch converted on a mol carbon basis) at 37° C. (d). The untransformed S. cerevisiae M2n strain+28 μl STARGEN™ (-▲-), M2n T1 (-■-), M2n T1+2.8 μl STARGEN™ (-◆-) and M2n T1+4.6 μl STARGEN™ (-●-). Data are the mean of 3 repeats showing standard deviation.

Similar results and trends were observed for the *S. cerevisiae* M2n strains at a fermentation temperature of 30° C., compared to the *S. cerevisiae* Ethanol Red™ equivalent strains (FIGS. 10 and 11). However, the final ethanol concentration for the *S. cerevisiae* M2n T1 transformant was higher >10 g·l$^{-1}$ after 192 hours (p=0.0392). At 30° C., the low residual levels of glucose and maltose in the fermentation broth (Table 8) indicated a rapid sugar uptake by all the amylolytic strains.

TABLE 8

Product formation by *S. cerevisiae* Ethanol Red ™ and M2n strains after 192 hours of fermentation at 30° C. in YP media, supplemented with different STARGEN ™ dosages

| *S. cerevisiae* strains | Ethanol Red ™ | M2n | Ethanol Red ™ T12 | M2n T1 | Ethanol Red ™ T12 |
|---|---|---|---|---|---|
| STARGEN ™ added (µl) | 28 | 28 | 2.8 | 2.8 | 5.6 |
| Substrate (g · l$^{-1}$) | | | | | |
| Raw starch weighed | 200 | 200 | 200 | 200 | 200 |
| Glucose weighed | 5 | 5 | 5 | 5 | 5 |
| Raw starch (dry weight) | 185 | 185 | 185 | 185 | 185 |
| Glucose equivalent | 208.5 | 208.5 | 208.5 | 208.5 | 208.5 |
| Products (g · l$^{-1}$) | | | | | |
| Glucose | 0.02 | 0.31 | 0.02 | 3.28 | 0.12 |
| Glycerol | 4.07 | 4.30 | 4.76 | 4.59 | 5.22 |
| Acetic acid | 0.00 | 0 | 0.90 | 0.31 | 0.96 |
| Ethanol | 97.23 | 98.49 | 98.37 | 99.08 | 100.32 |
| Maltose | 0.79 | 0.71 | 0.31 | 0.37 | 0.26 |
| $CO_2$[1] | 93.00 | 94.21 | 94.09 | 94.77 | 95.96 |
| Total | 195.11 | 198.02 | 198.44 | 202.40 | 202.85 |
| Carbon conversion (%) | 93.58 | 94.98 | 95.17 | 97.07 | 97.29 |
| Ethanol yield (% of theoretical yield)[2] | 93.26 | 94.48 | 94.36 | 95.04 | 96.23 |
| Ethanol rate of productivity[3] | 0.51 | 0.51 | 0.51 | 0.52 | 0.52 |

[1]$CO_2$ concentrations were deduced from the ethanol produced
[2]Ethanol yield (% of the theoretical yield) was calculated as the amount of ethanol produced per gram of consumed glucose
[3]Ethanol rate of productivity was calculated based ethanol titres produced per hour (g · l$^{-1}$ · h$^{-1}$)

At 37° C., the *S. cerevisiae* Ethanol Red T12 strain had a higher ethanol tolerance and was able to ferment for longer (compared to the *S. cerevisiae* M2n T1 strain) producing a 2.3-fold increase in ethanol concentration at 192 hours (FIGS. 10 and 11). Although the recombinant *S. cerevisiae* M2n T1 strain produced more ethanol at 30° C., it was severely affected at a higher fermentation temperature (FIG. 11). At 37° C., the ethanol concentrations plateaued after 48 hours for all the *S. cerevisiae* M2n fermentations (FIG. 11 b). The extent of carbon conversion displayed by the *S. cerevisiae* Ethanol Red T12 strain was similar (~83%) at the two fermentation temperatures (FIGS. 10c and d), while the carbon conversion displayed by the *S. cerevisiae* M2n T1 strain was 13% higher at 30° C., compared to the carbon conversion at 37° C. (FIGS. 11c and 11d). Both the amylolytic *S. cerevisiae* Ethanol Red T12 and M2n T1 strains had lower ethanol productivity at 37° C., compared to at 30° C. and residual glucose levels were >40 g·l$^{-1}$ at 37° C. (data not shown), which represented a large amount of unfermented glucose. Overall, results showed that temperature tolerance played a major role on the fermentation vigour of industrial *S. cerevisiae* Ethanol Red T12 and M2n T1 strains. The addition of STARGEN in combination with the amylolytic yeast strains reduced the fermentation time and increased the carbon conversion, compared to the control with untransformed strains and the recommended enzyme dosage.

Strain Comparison

Figure 12:
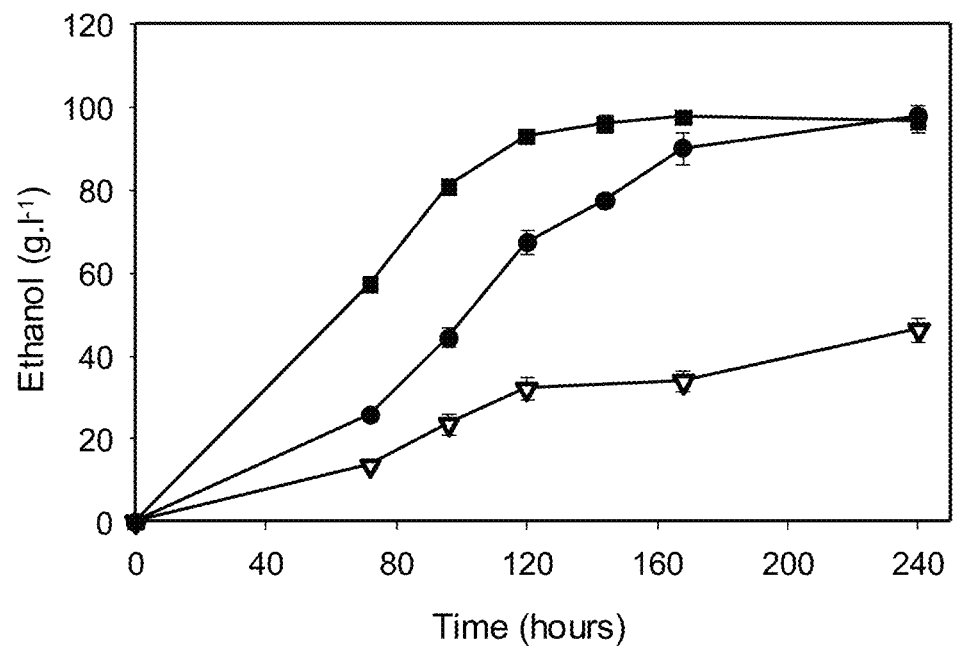
FIG. 12 Ethanol concentrations produced by recombinant industrial S. cerevisiae strains during fermentation in YP media that contained 5 g·l$^{-1}$ glucose and 200 g·l$^{-1}$ raw corn starch at 30° C. Ethanol Red™ T12 (-■-), M2n T1 (-●-) and M2n[TLG1-SFA1] (-▼-).

The *S. cerevisiae* Ethanol Red™ T12 and M2n T1 strains were compared in a small scale fermentation to a previously constructed amylolytic industrial strain M2n[TLG1-SFA1] (Favaro et al., 2015). Both the Ethanol Red™ T12 and M2n T1 strains performed better (FIG. 12), producing 50 g·l$^{-1}$ more ethanol after 240 hours of fermentation, compared to the M2n[TLG1-SFA1] strain, thus demonstrating the superior TemG_Opt and TemA_Nat enzyme combination for raw starch hydrolysis.

Fermentations in 5-Liter Bioreactor

Figure 13:
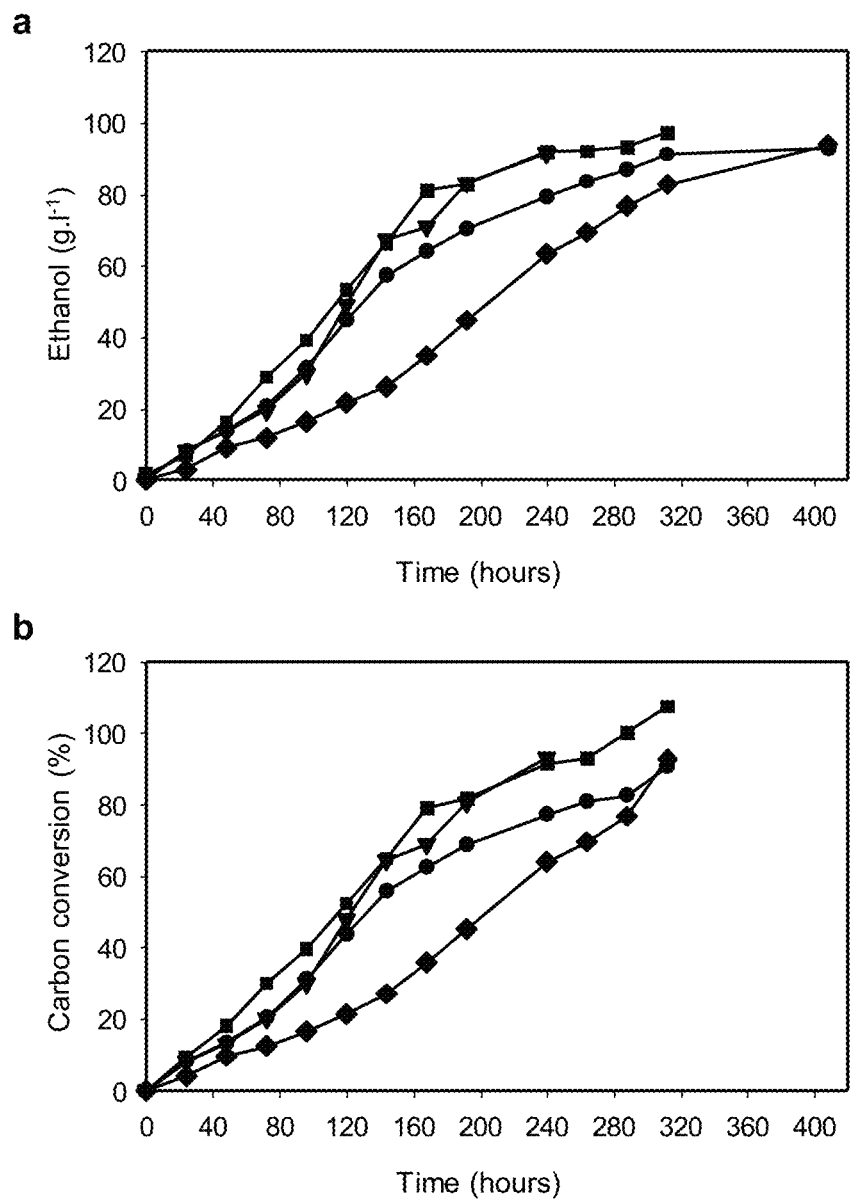
FIG. 13 Performance of the S. cerevisiae Ethanol Red™ T12 strain at different fermentation temperatures in YP media that contained 5 g·l$^{-1}$ glucose and 200 g·l$^{-1}$ raw corn starch. Ethanol produced (a) and carbon conversion (%) (b) at 30° C. (-◆-), 34° C. (-●-), 37° C. (-■-) in a 5 liter bioreactor, and at 30° C. (-▼-) in 100 ml serum bottles.

Overall, small scale fermentations demonstrated that the *S. cerevisiae* Ethanol Red™ T12 strain performed the best at higher fermentation temperatures. This strain also showed the highest activity levels during glucose assays because it had more integrated copies of the temG_Opt gene. Therefore, Ethanol Red™ T12 was evaluated further in bioreactor studies. The main advantage of the 5-liter bioreactor was a controlled internal temperature. Results depicted in FIG. 13 showed the effect on ethanol concentrations and carbon conversion when the fermentation temperature increased. The internal broth temperature can't be controlled during serum bottle fermentations and as a result the internal temperature exceeds that of the incubator's set temperature by ~2° C. After 144 hours, ~67 g·l$^{-1}$ ethanol was produced by the Ethanol Red™ T12 strain both in the bioreactor with an internal temperature of 37° C. and in the parallel fermentation in 100 ml serum bottles at 30° C. The strain's fermentative ability is affected (FIG. 13*a*) and ethanol concentrations do not compare (serum bottles versus bioreactor) because the temperature of the fermentation broth affects the rate of starch hydrolysis and subsequently the glucose available for fermentation to ethanol.

During the 5-liter bioreactor experiments at 37° C., the Ethanol Red™ T12 strain could hydrolyse starch quicker (compared to bioreactor fermentations at 30° C. and 34° C.) and the Ethanol Red™ T12 strain fermented all the available glucose to ethanol. After 168 hours, 81 g·l$^{-1}$ ethanol was produced at 37° C., compared to 64 g·l$^{-1}$ and 35 g·l$^{-1}$ ethanol at 34° C. and 30° C., respectively (FIG. 13*a*). Furthermore, there was at least a 2-fold increase in ethanol concentrations at a fermentation temperature of 37° C. compared to at 30° C. (during the first 7 days of fermentation). Therefore, these results confirmed that the Ethanol Red™ T12 strain was more robust compared to the *S. cerevisiae* Y294 strains (in Example 1) and performed well as a CBP yeast at 37° C.

Ratio Testing

Figure 14:
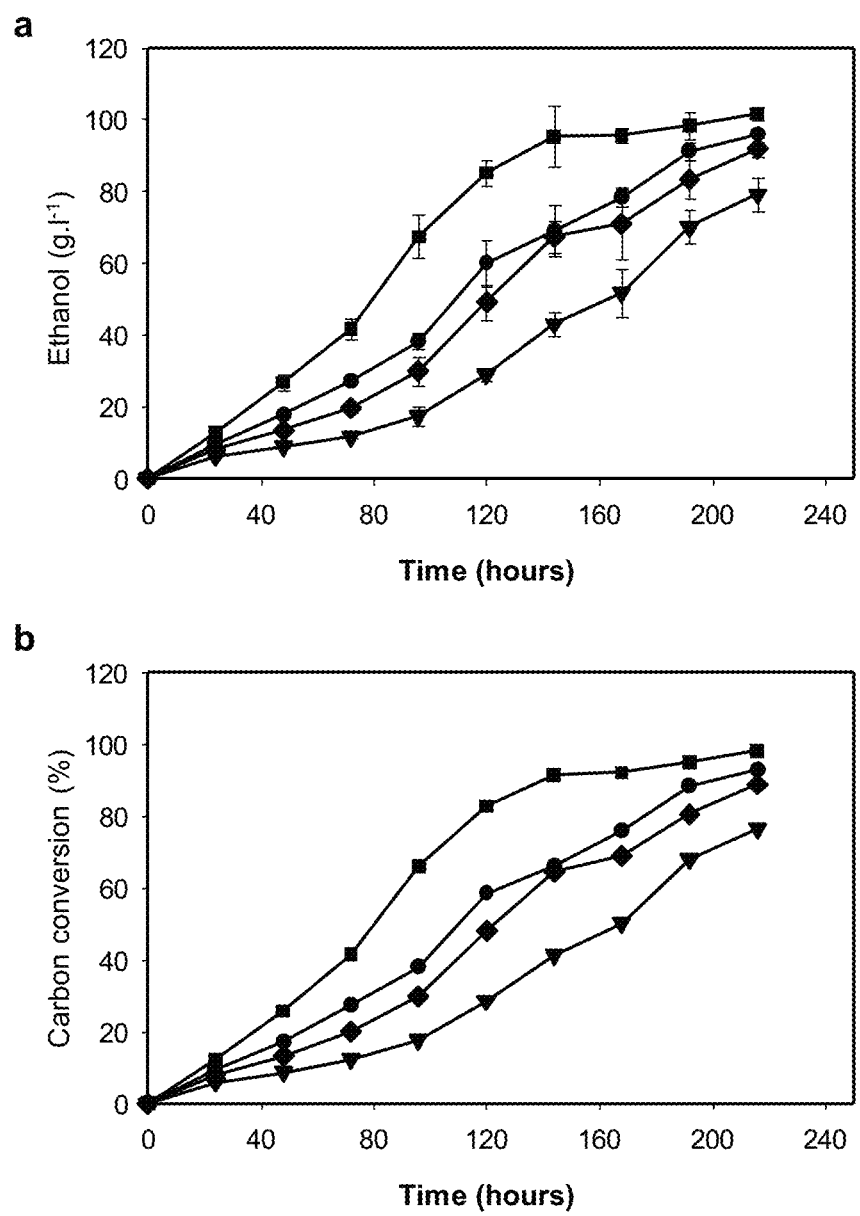
FIG. 14 Performance of the S. cerevisiae Ethanol Red™ T12 strain during fermentation in YP media that contained 5 g·l$^{-1}$ glucose and 200 g·l$^{-1}$ raw corn starch. Ethanol (a) and carbon conversion (%) (b) at 30° C. (total inoculum volume was 10% (v·v$^{-1}$)). 10 ml Ethanol Red™ T12 (-●-), 10 ml Ethanol Red™ T12+5 μl commercial glucoamylase (-■-), 5 ml Ethanol Red™ T12+5 ml untransformed Ethanol Red™ (-▼-), 5 ml Ethanol Red™ T12+5 ml untransformed Ethanol Red™+5 μl commercial glucoamylase (-◆-).

Synergy testing has allowed for an improved use of enzyme combinations for substrate hydrolysis and fermentation. Enzyme synergy refers to the action of two or more enzymes acting together in solution being greater than the sum of their individual actions. Traditionally, when using the conventional conversion of starch to ethanol, a higher dosage of glucoamylase has been used. Therefore, fermentations using the Ethanol Red™ T12 strain were performed with the supplementation of commercial glucoamylase (FIG. 14), in order to establish how different enzyme dosages affect the rate of ethanol production.

Fermentations with the Ethanol Red™ T12 strain supplemented with 10 µl commercial glucoamylase significantly increased the rate of ethanol production. After 144 hours, glucoamylase supplementation resulted in a 29 g·l$^{-1}$ (44%) increase in the ethanol concentration. In addition, if the amount of recombinant enzyme was decreased by a half (5 ml Ethanol Red™ T12+5 ml untransformed Ethanol Red™ as inoculum), the ethanol concentration dropped by 54% at 144 hours (FIG. 14*a*). FIG. 14*b* showed that the trends for carbon conversion were similar to ethanol concentration trends. This is because the strains were able to ferment all the available glucose to ethanol at a fermentation temperature of 30° C.

To further evaluate the optimal enzyme ratio for raw starch hydrolysis, an Ethanol Red™ strain expressing only the temA_Nat α-amylase was constructed. FIG. 15 showed the performance of the Ethanol Red™ TemA_Nat strain in combination with different dosages of commercial glucoamylase during small scale fermentations at 30° C. Results showed that the Ethanol Red™ T12 strain has a suboptimal ratio and ethanol production could be increased by either increasing the number of integrated gene copies or by supplementing the fermentation broth with small dosages of commercial enzyme. These results further demonstrated that industrial ethanol production can be improved by the use of a recombinant amylolytic *S. cerevisiae* strain.

Discussion

Gene Integration

Figure 7:
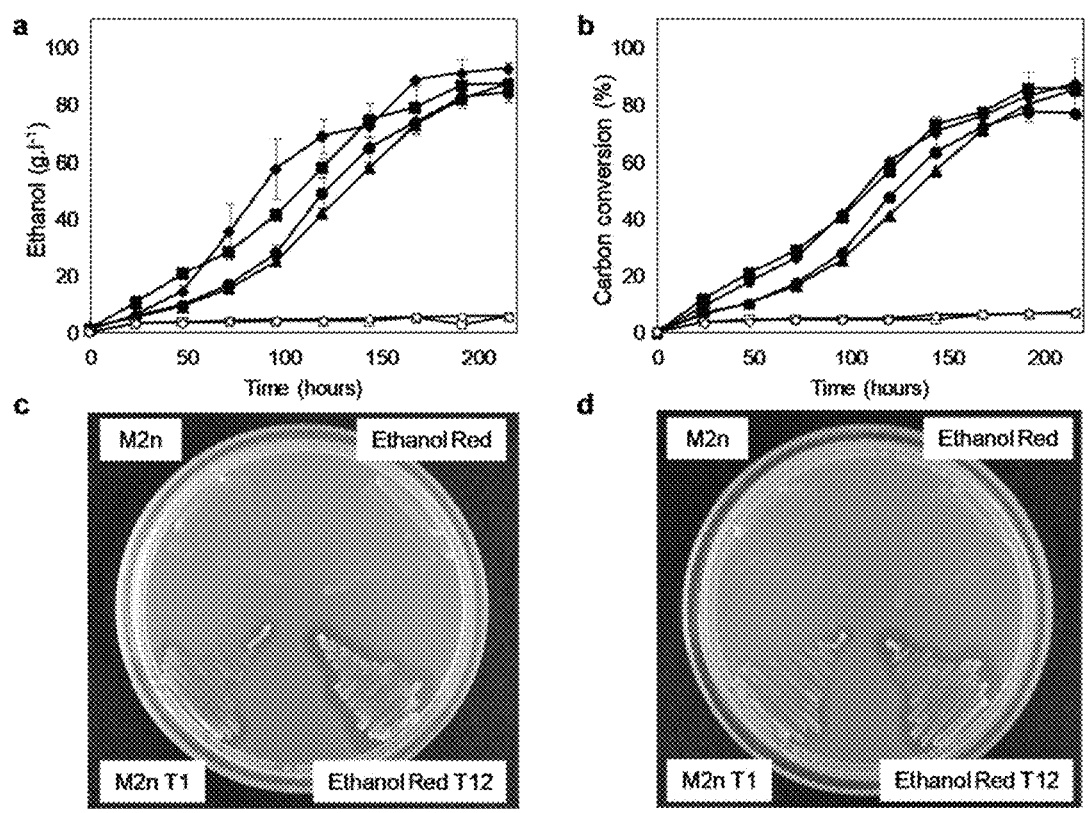
FIG. 7 Comparison of industrial transformants after integration of temA and temG gene cassettes. Ethanol produced (a) and carbon conversion (%) (b) displayed by S. cerevisiae Ethanol Red™ (-□-) and M2n (-◇-) parental strains and S. cerevisiae Ethanol Red™ T1 (-▲-), T12 (-■-), M2n T1 (-◆-) and Mn2 T2 (-●-) amylolytic transformants at a fermentation temperature of 30° C. on 200 g·l$^{-1}$ raw corn starch. SC-Ac (c) and SC-Acr (d) plate assays confirmed the ability of recombinant S. cerevisiae Ethanol Red™ T12 and M2n T1 strains to utilise acetamide and acrylamide, respectively, whereas the parental S. cerevisiae Ethanol Red™ and M2n strains indicated no growth.

After the initial screening process, four recombinant strains expressing the temG_Opt and temA_Nat gene cassettes (the *S. cerevisiae* Ethanol Red™ T1/T12 and *S. cerevisiae* M2n T1/T2 strains) were selected for further evaluation (FIG. 7). The *S. cerevisiae* M2n T1 strain performed better than the *S. cerevisiae* Ethanol Red™ T12 strain at 30° C. and achieved a maximum ethanol titre of 99.4 g·l$^{-1}$, which was 15% higher than the *S. cerevisiae* Ethanol Red™ T12 strain, at 192 hours (FIGS. 10*a* and 11*a*). However, at fermentations in serum bottles at 37° C., it was clear that the *S. cerevisiae* Ethanol Red™ T12 transformant had a greater fermentation vigour and was more ethanol and temperature tolerant (FIGS. 10*b* and 11*b*) compared to the *S. cerevisiae* M2n strain.

Results from this study showed significant improvements in starch hydrolysis and ethanol production when compared to the industrial *S. cerevisiae* M2n[TLG1-SFA1] (FIG. 12) and MEL2[TLG1-SFA1] amylolytic strains (Favaro et al., 2015) that produced 64 g·l$^{-1}$ ethanol from 200 g·l$^{-1}$ raw corn starch, corresponding to 55% of the maximum theoretical ethanol yield, as well as the *S. cerevisiae* Mnuα1[AmyA-GlaA] strain (Viktor et al., 2013) that produced 65.83 g·l$^{-1}$ ethanol (after 10 days) representing 57% of the maximum theoretical ethanol yield. Theoretical ethanol yields obtained from the recombinant industrial strains in this study were >90% and thus represented a significant improvement on previously constructed amylolytic strains.

Ethanol concentrations were also higher than those reported for the amylolytic yeast strain, which produced 46.5 g·l$^{-1}$ of ethanol from 200 g·l$^{-1}$ of raw corn starch after 120 hours of fermentation (Yamakawa et al., 2012). The amylolytic yeast strains expressing the temG_Opt and temA_Nat gene cassettes in this study were superior in their ethanol production, producing >50 g·l$^{-1}$ and >60 g·l$^{-1}$ ethanol for the *S. cerevisiae* Ethanol Red™ T12 and M2n T1 strains, respectively, after 120 hours (FIGS. 10*a* and 11*a*).

Furthermore, since the amylases were secreted into the fermentation broth they had increased physical contact with the starch granules, compared to recombinant yeast that displayed amylases on the cell's surface (Yamakawa et al., 2012). This eliminated potential bottlenecks and facilitated improved starch hydrolysis because the raw starch TemA_Nat and TemG_Opt amylases were able to penetrate starch granules and create pores more quickly.

STARGEN™ Addition

During fermentation with the amylolytic *S. cerevisiae* Ethanol Red™ and M2n strains, there was an initial lag phase in carbon conversion, up until 48 hours (FIGS. 10c and 11c). This was expected, since the strains first had to adjust to the fermentation conditions and produce amylases de novo. On the other hand, during the SSF process with STARGEN™ (FIGS. 10a and 11a), the enzymes were in abundance at the start of the fermentation and rapidly produced glucose upon addition. Therefore, although *S. cerevisiae* Ethanol Red™ T12 and M2n T1 strains were able to achieve high percentages of carbon conversion (FIG. 7b), supplementation with STARGEN™ (FIGS. 10, 11 and 14) increased ethanol productivity at the start of the fermentation.

In the industrial cold hydrolysis set-up for bioethanol production, commercial amylase enzymes are only added at the beginning of the process and therefore their overall efficiency will decrease over time. However, the amylolytic CBP yeasts of the present invention were able to continually replenish the recombinant enzymes in the fermentation broth and thus facilitated increased overall carbon conversion when the fermentation was supplemented with STARGEN™ (FIGS. 10c,10d, 11c and 11d). The cost of commercial enzyme addition was estimated at 4.8 US cents per gallon, representing 8.3% of the total possessing costs in ethanol production from corn (Wong et al., 2010). The recombinant amylolytic *S. cerevisiae* Ethanol Red™ T12 and M2n T1 strains described herein thus represent a novel alternative for lowering the enzyme dosage required for raw starch hydrolysis, as well as being able to provide continuous amylolytic activity for a continuous cold fermentations process. Furthermore, the use of amylolytic yeasts of the present invention would allow for a simplified fermentation design, since pretreatment steps and costs can be bypassed (Salehi Jouzani and Taherzadeh, 2015).

Fermentation Temperature

There are a number of other factors that are commonly associated with a stuck fermentation, including the yeast strain, nitrogen availability and glucose concentration (Henderson and Block, 2014). However, fermentation temperature is considered as one of the main bottlenecks with regards to ethanol production by SSF and CBP strategies. FIG. 9 showed the performance of the *S. cerevisiae* Ethanol Red™ T12 strain in different fermentation media and results confirmed that extra nitrogen (in the form of $(NH_4)_2SO_4$)) did not increase the fermentation of glucose to ethanol at a temperature of 37° C. Furthermore, increasing the pH of the conventional YP fermentation medium (to pH 5) did not improve fermentation conditions. Therefore, a lower pH was more favourable for starch conversion when using the TemG_Opt and TemA_Nat enzymes from *T. emersonii*, which have a pH optimum around 4-4.5 (Nielsen et al., 2002).

Strain robustness at higher temperatures and ethanol tolerance are two of the main characteristics that are desired by the biofuel industry. The demand for higher temperature fermentations began in the 1980s (Abdel-Banat et al., 2010). High-temperature fermentations may assist in making the simultaneous fermentation and ethanol extraction process more suitable for fuel ethanol production. Operational costs can be decreased (especially in regions with hot climates where cooling of fermentation vessels is required) and hydrolysis conditions improved (FIG. 13b). Ethanol production at high temperatures has several advantages, namely reduced risk of contamination, increased ethanol recovery, as well as decreased volumes of cooling waste-water effluent (Banat et al., 1998).

Currently, the fermentation temperatures used in industry are between 30-34° C. (Mukhtar et al., 2010). However, the effect of high temperature is also intensified by ethanol concentrations that exceed 3% (w·v$^{-1}$) and this affects the yeast cell's membrane causing protein denaturation. Therefore, robust yeasts that can ferment at temperatures above 37° C. are highly sought after. The internal temperature of a fermentation vessel typically exceeds incubation/exterior temperatures due to exogenic metabolic activities, as well as environmental temperatures in higher-temperature regions. This subsequently lowers the efficiency of ethanol production. Therefore, it is important to have a robust yeast that is cable of fermentation when the temperatures exceed 34° C. (FIG. 13a).

To demonstrate the importance of temperature control and investigate strain thermostability, fermentations using the Ethanol Red™ T12 strain were performed in parallel, both in serum bottles (incubated in a walk-in incubator set at 30° C.) and in a temperature controlled bioreactor (at 30° C., 34° C. and 37° C.) (FIG. 13). When fermentations at 30° C. were compared (bottles versus bioreactor), a 2-fold increase in ethanol concentrations was noted between 96 and 168 hours of incubation in serum bottle fermentations (FIG. 13a). This demonstrated the effect of internal temperature control on ethanol production from raw corn starch by a CBP yeast. Although there was unfermented glucose when fermentations were performed at 37° C. in serum bottles, thus resulting in ethanol levels that plateaued out around 75-80 g·l$^{-1}$ (FIG. 10b), the Ethanol Red™ T12 strain could ferment all the glucose at a controlled temperature of 37° C. (FIG. 13a).

The effect of temperature on fermentation products has been described by a number of different research groups (Favaro et al., 2013b; Woo et al. 2014). Although *S. cerevisiae* is known for its high ethanol tolerance and relatively high ethanol concentrations, it still lacks the ability to ferment at higher than normal temperatures (FIG. 10b). Moreover, ethanol concentrations of approximately 10% (w·v$^{-1}$) will reduce the fermentative activity of yeast by approximately 50% (Henderson and Block, 2014) and inhibit cell growth and viability. This leads to lower productivity and lower ethanol yields (Stanley et al., 2010). In order to improve ethanol tolerance of yeasts, the understanding of the cellular impact of ethanol toxicity needs to be explored.

Results for the comparison of ethanol production by recombinant *S. cerevisiae* Y294 and Ethanol Red™ T12 strains were in agreement with a study by Favaro et al. (2013b). They showed that at 30° C. the laboratory *S. cerevisiae* Y294 strain had lower fermentation vigour compared to the industrial strain at 30° C. The decreased ability to consume glucose could be explained by the *S. cerevisiae* Y294 strain displaying an optimum cultivation temperature around 25° C. and not 30° C. Similarly, the amylolytic *S. cerevisiae* Ethanol Red™ T12 strain had reduced fermentation vigour at 37° C. compared to 30° C. (FIG. 10b), when the internal temperature of the broth was not controlled.

Glycerol

Reduced glycerol concentrations were observed when lower fermentation temperatures were used, indicating that better carbon conversion to ethanol occurred at a fermentation temperature of 30° C. compared to 37° C. (FIG. 8*d*). Carbon source utilisation was important for the optimization of ethanol production (Navarrete et al., 2014) and results showed that the fermentation media influenced glycerol production (FIG. 8). The commercially available Trans-Ferm™ Yield+ yeast (Mascoma and Lallemand Biofuels and Distilled Spirits) was engineered to produce significantly less glycerol during fermentations so that more carbon can be utilised for ethanol production. In this study, the accumulating glycerol concentrations were below the conventional concentration (10 g·l$^{-1}$) (Huang et al., 2015) and therefore would not have had a significant effect on the yeast cells.

REFERENCES

Abdel-Banat B M A, Hoshida H, Ano A, Nonklang S, Akada R (2010) High-temperature fermentation: how can processes for ethanol production at high temperatures become superior to the traditional process using mesophilic yeast? Appl Microbiol Biotechnol 85:861-867. doi: 10.1007/s00253-009-2248-5

Allison D S, Rey M W, Berka R M, Armstrong G, Dunn-Coleman N S (1992) Transformation of the thermophilic fungus *Humicola grisea* var. *thermoidea* and over-production of *Humicola* glucoamylase. Curr Genet 21:225-229. doi: 10.1007/BF00336845

Amore A, Faraco V (2012) Potential of fungi as category I Consolidated BioProcessing organisms for cellulosic ethanol production. Renew Sust Energ Rev 16:3286-3301. doi.10.1016/j.rser.2012.02.050

Bai F W, Anderson W A, Moo-Young, M (2008) Ethanol fermentation technologies from sugar and starch feedstocks. Biotechnol Adv 26:89-105. Doi.10.1016/j.biotechadv.2007.09.002

Balcerek M, Pielech-Przybylska K (2013) Effect of simultaneous saccharification and fermentation conditions of native triticale starch on the dynamics and efficiency of process and composition of the distillates obtained. J Chem Technol Biotechnol 88:615-622. doi: 10.1002/jctb.3873

Banat I M, Nigam P, Singh D, Marchant R, McHale A P (1998) Ethanol production at elevated temperatures and alcohol concentrations: Part I—Yeasts in general. World J Microbiol Biotechnol 14:809-821. doi: 10.1023/A:1008802704374

Bideaux C, Alfenore S, Cameleyre X, Molina-Jouve C, Uribelarrea J L, Guillouet S E (2006) Minimization of glycerol production during the high-performance fed-batch ethanolic fermentation process in *Saccharomyces cerevisiae*, using a metabolic model as a prediction tool. Appl Environ Microbiol 72:2134-2140. doi: 10.1128/AEM.72.3.2134-2140.2006

Bothast R J, Schlicher M A (2005) Biotechnological processes for conversion of corn into ethanol. Appl Microbiol Biotechnol 67:19-25. doi:10.1007/s00253-004-1819-8

Brehmer B, Bals B, Sanders J, Dale B (2008) Improving the corn-ethanol industry: Studying protein separation techniques to obtain higher value-added product options for distillers grains. Biotechnol Bioeng 101:49-61. doi: 10.1002/bit.21881

Carbone A, Zinovyev A, Képès F (2003) Codon adaptation index as a measure of dominating codon bias. Bioinformatics 19:2005-2015. doi: 10.1093/bioinformatics/btg272

Celińska E, Białas W, Borkowska M, Grajek W (2015) Cloning, expression, and purification of insect (*Sitophilus oryzae*) alpha-amylase, able to digest granular starch, in *Yarrowia lipolytica* host. Appl Microbiol Biotechnol 99:2727-2739. doi: 10.1007/s00253-014-6314-2

Chen J, Zhang Y, Zhao C, Li A, Zhou Q, Li D (2007) Cloning of a gene encoding thermostable glucoamylase from *Chaetomium thermophilum* and its expression in *Pichia pastoris*. J Appl Microbiol 103:2277-2284. doi: 10.1111/j.1365-2672.2007.03475.x Chi Z, Wang F, Chi Z, Yue L, Liu G, Zhang T (2009) Bioproducts from *Aureobasidium pullulans*, a biotechnologically important yeast. Appl Microbiol Biotechnol 82:793-804. doi: 10.1007/s00253-009-1882-2

Cho K M, Yoo Y J, Kang H S (1999) δ-Integration of endo/exoglucanase and β-glucosidase genes into the yeast chromosomes for direct conversion of cellulose to ethanol. Enzyme Microb Technol 25:23-30. doi: 10.1016/50141-0229(99)00011-3

Damasceno L M, Huang C J, Batt C A (2012) Protein secretion in *Pichia pastoris* and advances in protein production. Appl Microbiol Biotechnol 93:31-39. doi: 10.1007/s00253-011-3654-z Demeke M M, Dumortier F, Li Y, Broeckx T, Foulquié-Moreno M R, Thevelein J M (2013) Combining inhibitor tolerance and D-xylose fermentation in industrial *Saccharomyces cerevisiae* for efficient lignocellulose-based bioethanol production. Biotechnol Biofuels 6:120. doi: 10.1186/1754-6834-6-120

Demeke M M, Dietz H, Li Y, Foulquié-Moreno M R, Mutturi S, Deprez S, Den Abt T, Bonini B M, Liden G, Dumortier F, Verplaetse A, Boles E, Thevelein J M (2013b) Development of a D-xylose fermenting and inhibitor tolerant industrial *Saccharomyces cerevisiae* strain with high performance in lignocellulose hydrolysates using metabolic and evolutionary engineering. Biotechnol Biofuels 6:89. doi: 10.1186/1754-6834-6-89

Den Haan R, Rose S H, Lynd L R, van Zyl W H (2007) Hydrolysis and fermentation of amorphous cellulose by recombinant *Saccharomyces cerevisiae*. Metab Eng 9:87-94. doi: 10.1016/j.ymben.2006.08.005 den Haan R, Kroukamp H, Mert M, Bloom M, Görgens J F, van Zyl W H (2013) Engineering *Saccharomyces cerevisiae* for next generation ethanol production. J Chem Technol Biotechnol 88:983-991. doi: 10.1002/jctb.4068 den Haan R, van Rensburg E, Rose S H, Görgens J, van Zyl W H (2015) Progress and challenges in the engineering of non-cellulolytic microorganisms for consolidated bioprocessing. Curr Opin Biotechnol 33:32-38. doi: 10.1016/j.copbio.2014.10.003

Eksteen J M, van Rensburg P, Cordero Otero R R, Pretorius I S (2003) Starch fermentation by recombinant *Saccharomyces cerevisiae* strains expressing the α-amylase and glucoamylase genes from *Lipomyces kononenkoae* and *Saccharomycopsis fibuligera*. Biotechnol Bioeng 84:639-646. doi: 10.1002/bit.10797

Favaro L, Jooste T, Basaglia M, Rose S H, Saayman M, Görgens J F, Casella S, van Zyl W H (2013) Designing industrial yeasts for consolidated bioprocessing of starchy biomass to ethanol. Bioengineered 4:97-102. doi: 10.4161/bioe.22268

Favaro L, Basaglia M, Trento A, van Rensburg E, García-Aparicio M, van Zyl W H, Casella S (2013b) Exploring grape marc as trove for new thermotolerant and inhibitor-tolerant *Saccharomyces cerevisiae* strains for second-generation bioethanol production. Biotechnol Biofuels 6:168. doi: 10.1186/1754-6834-6-168

Favaro L, Viktor M, Rose S H, Viljoen-Bloom M, van Zyl W H, Basaglia M, Cagnin L, Casella S (2015) Consolidated bioprocessing of starchy substrates into ethanol by industrial *Saccharomyces cerevisiae* strains secreting fungal amylases. Biotechnol Bioeng 112:1751-1760. doi: 10.1002/bit.25591

Futatsumori-Sugai M, Tsumoto K (2010) Signal peptide design for improving recombinant protein secretion in the baculovirus expression vector system. Biochem Biophys Res Commun 391:931-935. doi: 10.1016/j.bbrc.2009.11.167

Görgens J F, Bressler D C, van Rensburg E (2015) Engineering *Saccharomyces cerevisiae* for direct conversion of raw, uncooked or granular starch to ethanol. Crit Rev Biotechnol 35:369-391. doi: 10.3109/07388551.2014.888048

Gupta R, Gigras P, Mohapatra H, Goswami V K, Chauhan B (2003) Microbial α-amylases: a biotechnological perspective. Process Biochem 38:1599-1616. doi: 10.1016/S0032-9592(03)00053-0

Hashimoto Y, Koyabu N, Imoto T (1998) Effects of signal sequences on the secretion of hen lysozyme by yeast: construction of four secretion cassette vectors. Protein Eng 11:75-77. doi: 10.1093/protein/11.2.75

Henderson C M, Block D E (2014) Examining the role of membrane lipid composition in determining the ethanol tolerance of *Saccharomyces cerevisiae*. Appl Environ Microbiol 80:2966-2972. doi: 10.1128/AEM.04151-13

Hii S L, Tan J S, Ling T C, Ariff A B (2012) Pullulanase: role in starch hydrolysis and potential industrial applications. Enzyme Res 2012:921362. doi: 10.1155/2012/921362

Houbraken J, Spierenburg H, Frisvad J C (2012) *Rasamsonia*, a new genus comprising thermotolerant and thermophilic *Talaromyces* and *Geosmithia* species. Antonie Van Leeuwenhoek 101: 403-421. doi: 10.1007/s10482-011-9647-1

Huang H, Qureshi N, Chen M H, Liu W, Singh V (2015) Ethanol production from food waste at high solids content with vacuum recovery technology. J Agric Food Chem 63:2760-2766. doi: 10.1021/jf5054029

Inlow D, McRae J, Ben-Bassat A (1988) Fermentation of corn starch to ethanol with genetically engineered yeast. Biotechnol Bioeng 32:227-234. doi: 10.1002/bit.260320213

Kim H R, Im Y K, Ko H M, Chin, J E, Kim I C, Lee H B, Bai S (2011) Raw starch fermentation to ethanol by an industrial distiller's yeast strain of *Saccharomyces cerevisiae* expressing glucoamylase and α-amylase genes. Biotechnol Lett 33:1643-1648. doi: 10.1007/s10529-011-0613-9

Knox A M, Du Preez J C, Kilian S G (2004) Starch fermentation characteristics of *Saccharomyces cerevisiae* strains transformed with amylase genes from *Lipomyces kononenkoae* and *Saccharomycopsis fibuligera*. Enzyme Microb Technol 34:453-460.

Liakopoulou-Kyriakides M, Karakatsanis A, Stamatoudis M, Psomas S (2001) Synergistic hydrolysis of crude corn starch by α-amylases and glucoamylases of various origins. Cereal Chem 78:603-607. doi: 10.1094/CCHEM.2001.78.5.603

Machovic M, Janecek S (2006) Starch-binding domains in the post-genome era. Cell Mol Life Sci 63:2710-2724

Mamo G, Gessesse A (1999) Purification and characterization of two raw-starch-digesting thermostable α-amylases from a thermophilic *Bacillus*. Enzyme Microb Technol 25:433-438. doi: 10.1016/S0141-0229(99)00068-X Man J, Yang Y, Huang J, Zhang C, Zhang F, Wang Y, Gu M, Liu Q, Wei C (2013) Morphology and structural properties of high-amylose rice starch residues hydrolysed by amyloglucosidase. Food Chem 138:2089-2098. doi: 10.1016/j.foodchem.2012.12.009

Miller G L (1959) Use of dinitrosalicyclic acid reagent for determination of reducing sugars. Anal Chem 31:426-428. doi: 10.1021/ac60147a030

Mitsuiki S, Mukae K, Sakai M, Goto M, Hayashida S, Furukawa K (2005) Comparative characterization of raw starch hydrolyzing α-amylases from various *Bacillus* strains. Enzyme Microb Technol 37:410-416. doi: 10.1016/j.enzmictec.2005.02.022

Mukhtar K, Asgher M, Afghan S, Hussain K, Zia-Ul-Hussnain S (2010) Comparative study on two commercial strains of *Saccharomyces cerevisiae* for optimum ethanol production on industrial scale. J Biomed Biotechnol 210:419586. doi: 10.1155/2010/419586

Naguleswaran S, Vasanthan T, Hoover R, Bressler D (2013) The susceptibility of large and small granules of waxy, normal and high-amylose genotypes of barley and corn starches toward amylolysis at sub-gelatinization temperatures. Food Res Int 51:771-782. doi: 10.1016/j.foodres.2013.01.057

Navarrete C, Nielsen J, Siewers V (2014) Enhanced ethanol production and reduced glycerol formation in fps1Δ mutants of *Saccharomyces cerevisiae* engineered for improved redox balancing. AMB Express 4:86. doi: 10.1186/s13568-014-0086-z Nielsen B R, Lehmbeck J, Frandsen T P (2002) Cloning, heterologous expression, and enzymatic characterization of a thermostable glucoamylase from *Talaromyces emersonii*. Protein Expr Purif 26:1-8. doi: 10.1016/S1046-5928(02)00505-3

Njokweni A, Rose S H, van Zyl W H (2012) Fungal β-glucosidase expression in *Saccharomyces cerevisiae*. J Mol Microbiol Biotechnol 39:1445-1452. doi: 10.1007/s10295-012-1150-9

Nkomba E Y, van Rensburg E, Chimphango A F, Görgens J F (2016) The influence of sorghum grain decortication on bioethanol production and quality of the distillers' dried grains with solubles using cold and conventional warm starch processing. Bioresour Technol 203:181-189. doi: 10.1016/j.biortech.2015.12.045

O'Connell K, Stults J T (1997) Identification of mouse liver proteins on two-dimensional electrophoresis gels by matrix-assisted laser desorption/ionization mass spectrometry of in situ enzymatic digests. Electrophoresis 18:349-359. doi: 10.1186/1754-6834-6-167

Presečki A V, Blažević Z F, Vasić-Rački D (2013) Complete starch hydrolysis by the synergistic action of amylase and glucoamylase: impact of calcium ions. Bioprocess Biosyst Eng 36:1555-1562. doi: 10.1007/s00449-013-0926-2

Robertson G H, Wong D W, Lee C C, Wagschal K, Smith M R, Orts W J (2006) Native or raw starch digestion: a key step in energy efficient biorefining of grain. J Agric Food Chem 54:353-365. doi: 10.1021/jf051883m Salehi Jouzani G, Taherzadeh M J (2015) Advances in consolidated bioprocessing systems for bioethanol and butanol production from biomass: a comprehensive review. Biofuel Res J 2:152-195. doi: 10.18331/BRJ2015.2.1.4

Sambrook J, Fritsch E F, Maniatis T (1989) Molecular cloning: a laboratory manual. Cold Spring Harbor, N.Y.: Cold Spring Harbor Laboratory Press Santiago M, Linares L, Sánchez S, Rodríguez-Sanoja R. (2005) Functional characteristics of the starch-binding domain of *Lactobacillus amylovorus* α-amylase. Biologia (Bratislava) 60:111-114.

Schmidt S A, Tran T, Chambers P J, Herderich M J, Pretorius I S (2006) Developing indicators of wine yeast performance: an overview of the impact of ethanol stress. Austral New Zealand Wine Industry J 21:24-30.

Solis-Escalante D, Kuijpers N G A, Bongaerts N, Bolat I, Bosman L, Pronk J T, Daran J M, Daran-Lapujade P (2013) amdSYM, a new dominant recyclable marker cassette for *Saccharomyces cerevisiae*. FEMS Yeast Res 13: 126-139. doi: 10.1111/1567-1364.12024

Stanley D, Bandara A, Fraser S, Chambers P J, Stanley G A (2010) The ethanol stress response and ethanol tolerance of *Saccharomyces cerevisiae*. J Appl Microbiol 109:13-24. doi: 10.1111/j.1365-2672.2009.04657.x Stovicek V, Borodina I, Forster J (2015) CRISPR-Cas system enables fast and simple genome editing of industrial *Saccharomyces cerevisiae* strains. Metab Eng Commun 2:13-22. doi: 10.1016/j.meteno.2015.03.00

Stovicek V, Borja G M, Forster J, Borodina I (2015b) EasyClone 2.0: expanded toolkit of integrative vectors for stable gene expression in industrial *Saccharomyces cerevisiae* strains. J Ind Microbiol Biotechnol 42:1519-1531. doi: 10.1007/s10295-015-1684-8

Sun H, Zhao P, Ge X, Xia Y, Hao Z, Liu J, Peng M (2010) Recent advances in microbial raw starch degrading enzymes. Appl Biochem and Biotechnol 160:988-1003. doi: 10.1007/s12010-009-8579-y Szymanowska-Powalowska D, Lewandowicz G, Kubiak P, Blaszczak W (2014) Stability of the process of simultaneous saccharification and fermentation of corn flour. The effect of structural changes of starch by stillage recycling and scaling up of the process. Fuel 119:328-334. doi.org/10.1016/j.fuel.2013.11.034

Thorsen T S, Johnsen A H, Josefsen K, Jensen B (2006) Identification and characterization of glucoamylase from the fungus *Thermomyces lanuginosus*. Biochim Biophys Acta 1764:671-676. doi: 10.1016/j.bbapap.2006.01.009

Tyo K E J, Liu Z, Petranovic D, Nielsen J (2012) Imbalance of heterologous protein folding and disulfide bond formation rates yields runaway oxidative stress. BMC Biol 10:16. doi: 10.1186/1741-7007-10-16

Uthumporn U, Zaidul I S M, Karim A A (2010) Hydrolysis of granular starch at sub-gelatinization temperature using a mixture of amylolytic enzymes. Food and Bioprod Process 88:47-54. doi: 10.1016/j.fbp.2009.10.001 van Rensburg E, den Haan R, Smith J, van Zyl W H, Görgens J F (2012) The metabolic burden of cellulase expression by recombinant *Saccharomyces cerevisiae* Y294 in aerobic batch culture. Appl Microbiol and Biotechnol 96:197-209. doi: 10.1007/s00253-012-4037-9 van Wyk N, den Haan R, van Zyl W H (2010) Heterologous production of NpCel6A from *Neocallimastix patriciarum* in *Saccharomyces cerevisiae*. Enzyme Microb Technol 46:378-383. doi: 10.1016/j.enzmictec.2009.11.005 van Zyl W H, Bloom M, Viktor M J (2012) Engineering yeasts for raw starch conversion. Appl Microbiol Biotechnol 95:1377-1388. doi: 10.1007/s00253-012-4248-0

Viktor M J, Rose S H, van Zyl W H, Viljoen-Bloom M (2013) Raw starch conversion by *Saccharomyces cerevisiae* expressing *Aspergillus tubingensis* amylases. Biotechnol Biofuels 6:167. doi: 10.1186/1754-6834-6-167

Wallace-Salinas V, Gorwa-Grauslund M F (2013) Adaptive evolution of an industrial strain of *Saccharomyces cerevisiae* for combined tolerance to inhibitors and temperature. Biotechnol Biofuels 6:151. doi: 10.1186/1754-6834-6-151

Wang K, Luo H, Shi P, Huang H, Bai Y, Yao B (2014) A highly-active endo-1,3-1,4-beta-glucanase from thermophilic *Talaromyces emersonii* CBS394.64 with application potential in the brewing and feed Wong D, Batt Throne S B, Robertson G H, Lee C C, Wagschal K C (2010) Chromosomal integration of both an alpha-amylase and a glucoamylase gene in *Saccharomyces cerevisiae* for starch conversion. Ind Biotechnol 6:112-119. doi: 10.1089/ind.2010.0010.

Woo J M, Yang K M, Kim S U, Blank L M, Park J B (2014) High temperature stimulates acetic acid accumulation and enhances the growth inhibition and ethanol production by *Saccharomyces cerevisiae* under fermenting conditions. Appl Microbiol Biotechnol 98:6085-6094. doi: 10.1007/s00253-014-5691-x Yamakawa S, Yamada R, Tanaka T, Ogino C, Kondo A (2012) Repeated fermentation from raw starch using *Saccharomyces cerevisiae* displaying both glucoamylase and α-amylase. Enzyme Microb Technol 50:343-347. doi: 10.1016/j.enzmictec.2012.03.005

Yang S, Jia N, Li M, Wang J (2011) Heterologous expression and efficient ethanol production of a *Rhizopus* glucoamylase gene in *Saccharomyces cerevisiae*. Mol Biol Rep 38:59-64. doi: 10.1007/s11033-010-0077-3

The invention claimed is:

1. A recombinant yeast which has been transformed with:
   a) a first heterologous gene which encodes an α-amylase from *Rasamsonia emersonii* having α-amylase activity, the first heterologous gene consisting of an amino acid sequence which is at least 90% identical to SEQ ID NO: 1 and which has a starch-binding domain, wherein the nucleic acid sequence of the first gene is not codon-optimized; and
   b) a second heterologous gene which encodes a glucoamylase from *Rasamsonia emersonii* having glucoamylase activity, the second heterologous gene consisting of an amino acid sequence which is at least 90% identical to SEQ ID NO: 2 and which has a starch-binding domain, wherein the nucleic acid sequence of the second gene is optionally codon-optimized;
   the recombinant yeast being capable of converting raw and cooked starch to ethanol in a single step without the addition of exogenous starch hydrolysing enzymes.

2. The recombinant yeast according to claim 1, wherein the amino acid sequence of the α-amylase is SEQ ID NO: 1.

3. The recombinant yeast according to claim 1, wherein the amino acid sequence of the glucoamylase is SEQ ID NO: 2.

4. The recombinant yeast according to claim 1, wherein the nucleic acid sequence of the first gene is at least 85% identical to SEQ ID NO: 3.

5. The recombinant yeast according to claim 1, wherein the nucleic acid sequence of the second gene is:
   (a) codon-optimized and is at least 85% identical to SEQ ID NO: 4; or
   (b) not codon-optimized and is at least 85% identical to SEQ ID NO: 5.

6. The recombinant yeast according to claim 1, wherein the yeast is a *Saccharomyces* species.

7. The recombinant yeast according to claim 6, wherein the yeast is a *Saccharomyces cerevisiae* species.

8. A process for producing an alcohol from starch or sugars, the process comprising the steps of:
   a) adding the recombinant yeast according to claim 1 to a composition comprising starch or sugars;
   b) causing the recombinant yeast to express and secrete (i) an α-amylase from *Rasamsonia emersonii* consisting of an amino acid sequence which is at least 90% identical to SEQ ID NO: 1 and (ii) a glucoamylase from *Rasamsonia emersonii* consisting of an amino acid sequence which is at least 90% identical to SEQ ID NO: 2;
   c) causing saccharification and/or fermentation to occur so that the starch or sugars are converted to an alcohol in a single step.

9. The process according to claim 8, wherein the starch is grain starch.

10. The process according to claim 8, wherein the starch is raw starch.

11. The process according to claim 10, wherein the raw starch is hydrolysed by the recombinant yeast without requiring cooking of the starch.

12. The process according to claim 11, wherein the raw starch is hydrolysed by the recombinant yeast at a temperature of no more than 40° C.

13. The process according to claim 8, wherein the sugars comprise glucose.

14. The process according to claim 8, wherein the alcohol is selected from the group consisting of ethanol and butanol.

15. The process according to claim 14, wherein the alcohol is ethanol.

16. The A process according to claim 8, wherein enzymes exogenous to the recombinant yeast are also added to the composition.

17. The process according to claim 16, wherein the exogenous enzymes are added in an amount which is at least 50% less than the amount of enzymes added to cold hydrolysis processes which do not use the recombinant yeast of claim 1.

18. The recombinant yeast of claim 1, which is further capable of attaining a carbon conversion of greater than 70% when the starch is corn starch.

19. The process of claim 8, which attains a carbon conversion of greater than 70%.

* * * * *